United States Patent [19]
Thompson

[11] Patent Number: 5,997,554
[45] Date of Patent: Dec. 7, 1999

[54] SURGICAL TEMPLATE AND SURGICAL METHOD EMPLOYING SAME

[75] Inventor: Ronald J. Thompson, Ft. Thomas, Ky.

[73] Assignee: Medworks Corporation, Louisville, Ky.

[21] Appl. No.: 08/818,391

[22] Filed: Mar. 14, 1997

Related U.S. Application Data

[63] Continuation-in-part of application No. 08/490,281, Jun. 14, 1995, Pat. No. 5,697,931.

[51] Int. Cl.$^6$ .................................................... A61B 17/04
[52] U.S. Cl. ............................................................. 606/148
[58] Field of Search ..................... 606/103, 96, 148–150; 600/29; 604/174, 175; 128/DIG. 26

[56] References Cited

U.S. PATENT DOCUMENTS

| | | |
|---|---|---|
| 1,571,956 | 2/1926 | Molinelli . |
| 3,176,690 | 4/1965 | H'Doubler ...................... 128/DIG. 26 |
| 3,357,422 | 12/1967 | Creelman . |
| 3,901,226 | 8/1975 | Scardenzan ...................... 128/DIG. 26 |
| 4,072,144 | 2/1978 | Pelosi et al. . |
| 4,612,939 | 9/1986 | Robertson . |
| 4,742,929 | 5/1988 | Law et al. . |
| 4,938,760 | 7/1990 | Burton et al. . |
| 4,985,038 | 1/1991 | Lyell . |
| 4,986,628 | 1/1991 | Lozhenko et al. . |
| 5,007,894 | 4/1991 | Enhorning . |
| 5,013,292 | 5/1991 | Lemay . |
| 5,019,032 | 5/1991 | Robertson . |
| 5,030,199 | 7/1991 | Barwock et al. . |
| 5,032,124 | 7/1991 | Menton . |
| 5,084,004 | 1/1992 | Ranoux . |
| 5,112,344 | 5/1992 | Petros . |
| 5,209,754 | 5/1993 | Ahluwalia . |
| 5,217,466 | 6/1993 | Hasson . |
| 5,342,353 | 8/1994 | Allen . |
| 5,342,374 | 8/1994 | Wan et al. . |
| 5,368,598 | 11/1994 | Hasson . |
| 5,437,603 | 8/1995 | Cerny et al. . |
| 5,439,467 | 8/1995 | Benderev et al. . |
| 5,478,339 | 12/1995 | Tadir et al. . |
| 5,496,345 | 3/1996 | Kieturakis et al. . |
| 5,507,796 | 4/1996 | Hasson . |
| 5,514,091 | 5/1996 | Yoon . |
| 5,540,711 | 7/1996 | Kieturakis et al. . |
| 5,544,664 | 8/1996 | Benderev et al. . |
| 5,549,617 | 8/1996 | Green et al. . |
| 5,582,188 | 12/1996 | Benderev et al. . |
| 5,591,163 | 1/1997 | Thompson . |
| 5,611,515 | 3/1997 | Benderev et al. . |
| 5,620,012 | 4/1997 | Benderev et al. . |
| 5,643,288 | 7/1997 | Thompson . |
| 5,647,836 | 7/1997 | Blake, III et al. . |

FOREIGN PATENT DOCUMENTS

| | | |
|---|---|---|
| 2697989 | 5/1994 | France . |
| 1093329 | 5/1984 | U.S.S.R. . |
| 638892 | 6/1950 | United Kingdom . |
| 2268690A | 1/1994 | United Kingdom . |
| 9310715 | 6/1993 | WIPO . |

OTHER PUBLICATIONS

T.V. Benderev, *Anchor Fixation and Other Modifications of Endoscopic Bladder Neck Suspension*, Urology, Nov. 1992, vol. 40, No. 5, pp. 409–418.

(List continued on next page.)

*Primary Examiner*—Michael Buiz
*Assistant Examiner*—William Lewis
*Attorney, Agent, or Firm*—Dinsmore & Shohl LLP

[57] ABSTRACT

A template for guiding the placement of a fixation device during a surgical procedure. The template comprises:

(a) a body portion; and (b) at least one guide disposed in a predetermined spacial relationship to the body portion;

wherein the template is configured such that at least a portion of the template may be aligned within the vagina of a patient such that the guide may be employed to direct the placement of a fixation device or other medical instrument through at least a portion of the tissue adjacent the vagina. A surgical method employing this template is also provided, along with an urethral sling used in conjunction with one embodiment of the template.

81 Claims, 39 Drawing Sheets

OTHER PUBLICATIONS

Mitek Surgical Products, Inc., *Bladder Neck Suspension For Needle Suspension Techniques,* Aug. 1993.

G.E. Leach, *Bone Fixation Technique For Transvaginal Needle Suspension,* Urology, May 1988, vol. XXXI, No. 5, pp. 388–390.

C.A. Olsson, *Extraperitoneal Endoscopic Vesicourethral Suspension (EEVUS),* Current Surgical Techniques in Urology, 1993, vol. 6, Issue 5.

M.A. Pelosi III, M.A. Pelosi, *Laparoscopic–Assisted Pubovaginal Sling Procedure for the Treatment of Stress Urinary Incontinence,* The Journal of the American Association of Gynecologic Laparoscopists, Aug. 1996, vol. 3, No. 4, pp. 593–600.

M.A. Pelosi, M.A. Pelosi III *Laparoscopic Hysterectomy with Bilateral Salpingo–oophorectomy Using a Single Umbilical Puncture,* New Jersey Medicine, Oct. 1991, vol. 88, No. 10, pp. 721–726.

D.Y. Liu, *Laparoscopic Retropubic Colposuspension(Burch Procedure),* pp. 1–12 (Mar. 1993).

C.H. Nezhat, Farr Nezhat, Camran R. Nezhat, Howard Rottenberg; *Laparoscopic Retropubic Cystourethropexy,* Aug. 1994, vol. 1 No. 4, Part 1, The Journal of the American Association of Gynecologic Laparoscopists, pp. 339–349.

K.E. Krantz, D. Litt, *The Marshall–Marchetti–Krantz Surgical Technique for Urinary Stress Incontinence,* brochure (Aug. 1994).

Imagyn Medical, Inc. *The MicroSpan Hysteroscope,* 1996, various pgs.

T.V. Benderev, *A Modified Percutaneous Outpatient Bladder Neck Suspension System,* The Journal of Urology, Dec. 1994, vol. 152, pp. 2316–2320.

The Cincinnati Enquirer—Tempo Section, *New Help for an Old Problem,* Mar. 15, 1995.

Mitek Surgical Products, Inc., *Retropubic Bladder Neck Suspension System,* 1994.

V.C. Mascio, *Retropubic periurethral bladder neck suspension using Mitek anchors,* Contemporary OB/GYN, Jul. 1996, pp. 1–6.

Spacemaker Surgical Balloon Dissector, product brochure, 1994.

R.L. Salerno, Using the laparoscope for SUI, Contemporary OB/GYN, Dec. 1994, pp. 35–40.

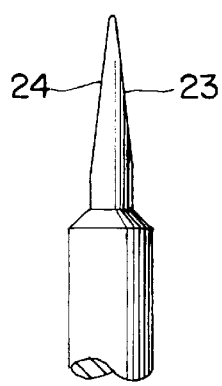
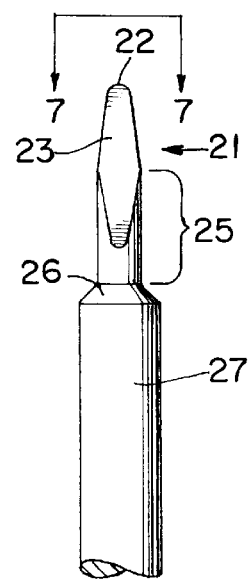
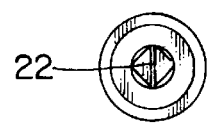
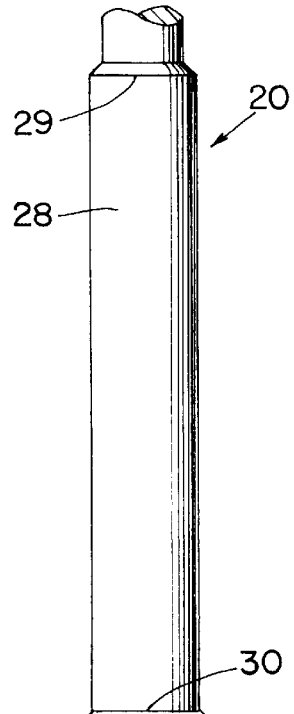
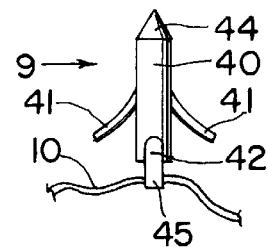
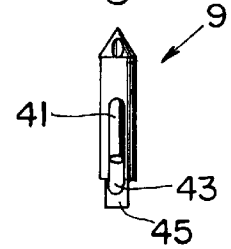
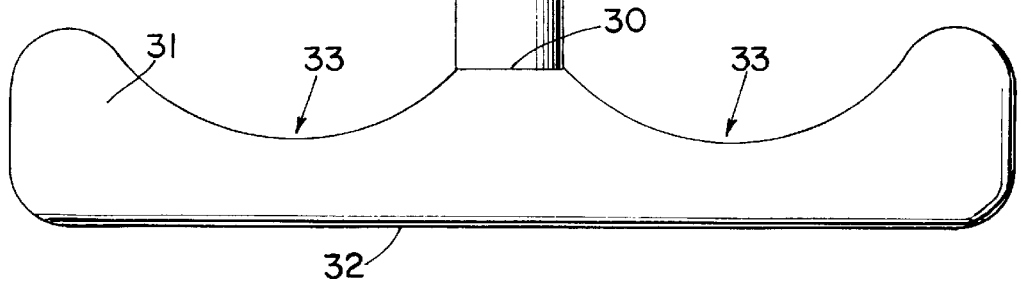

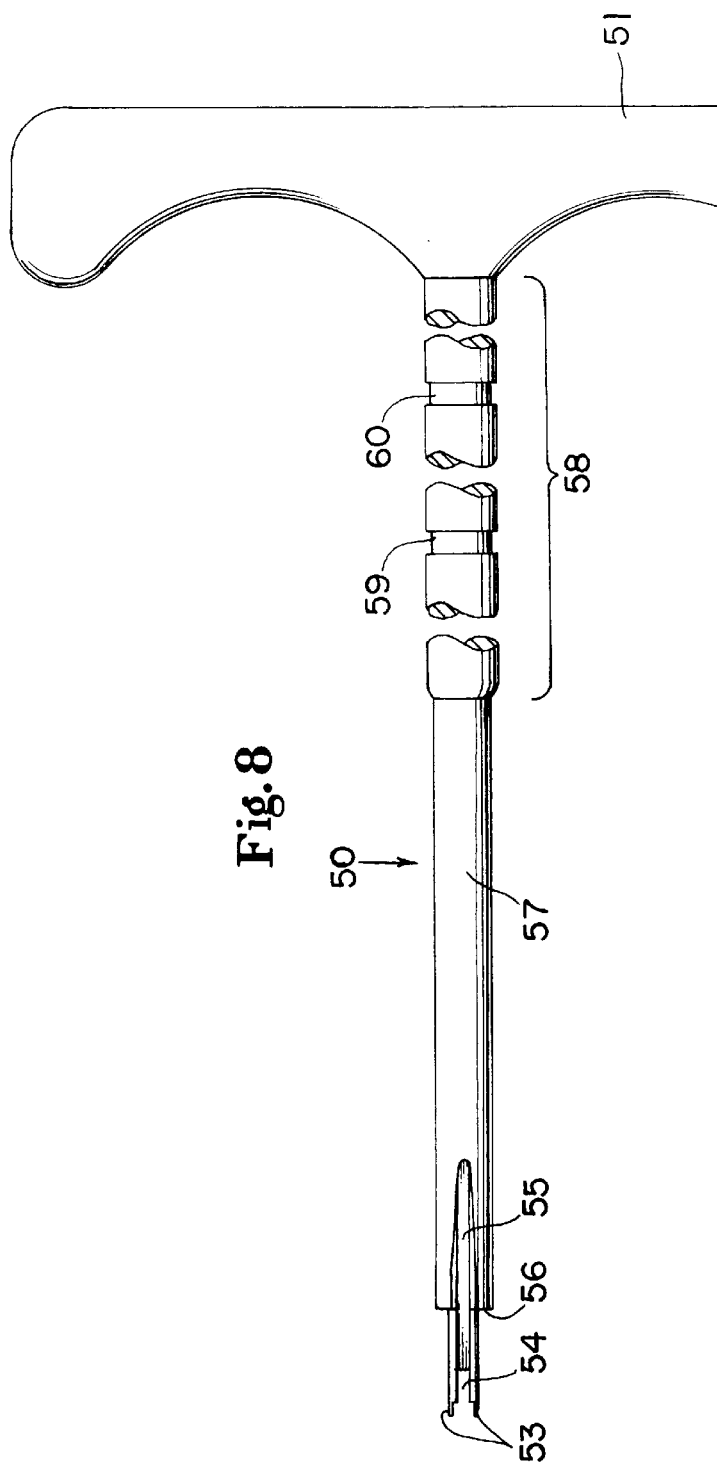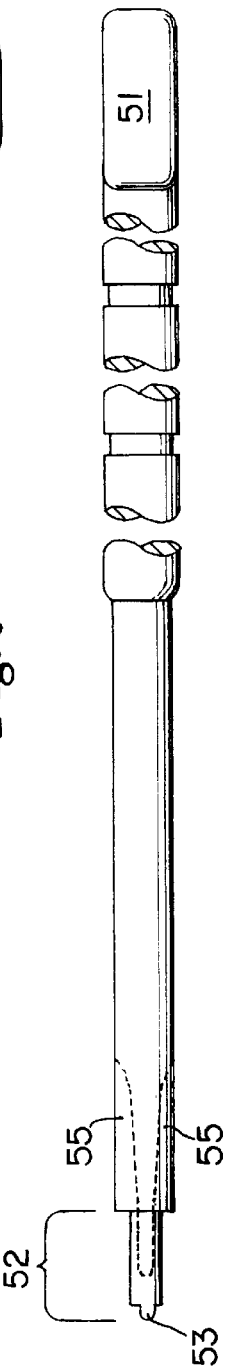

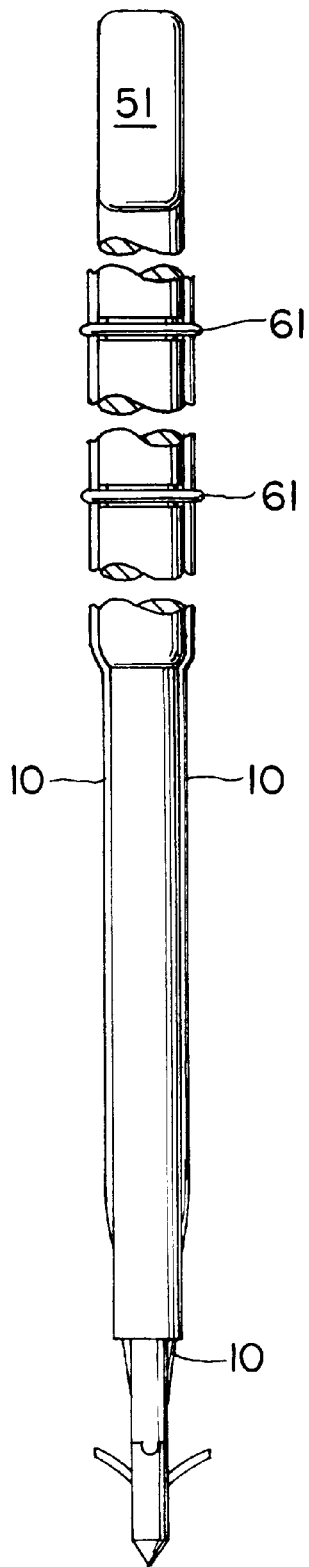
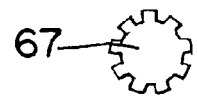
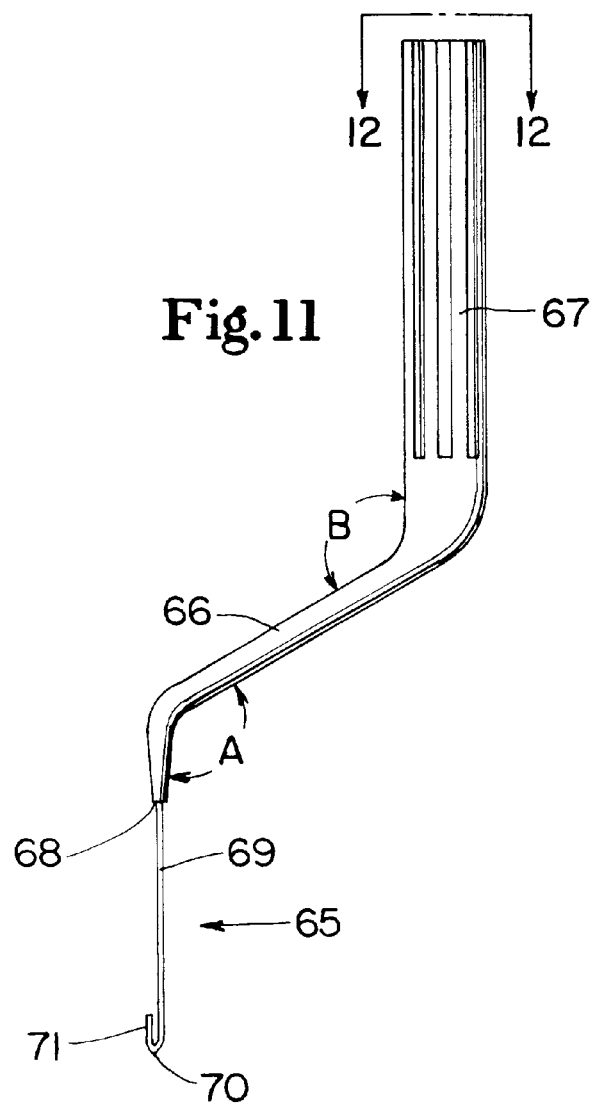

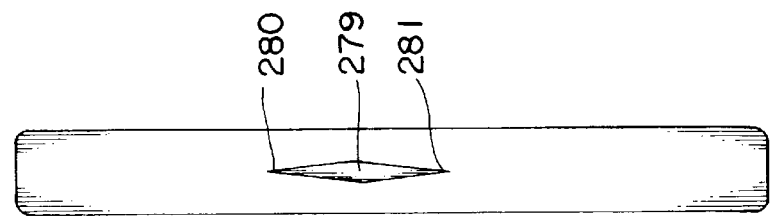
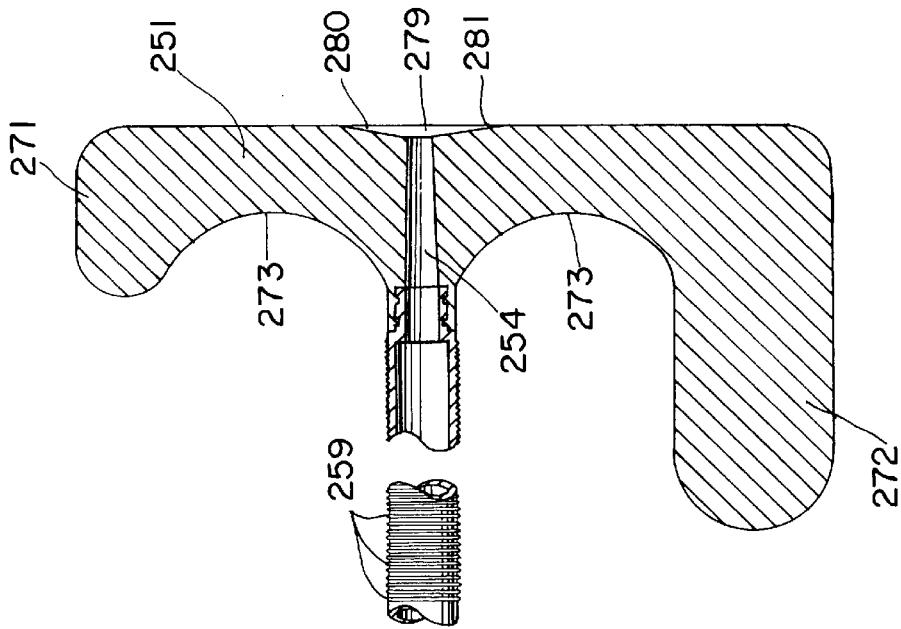
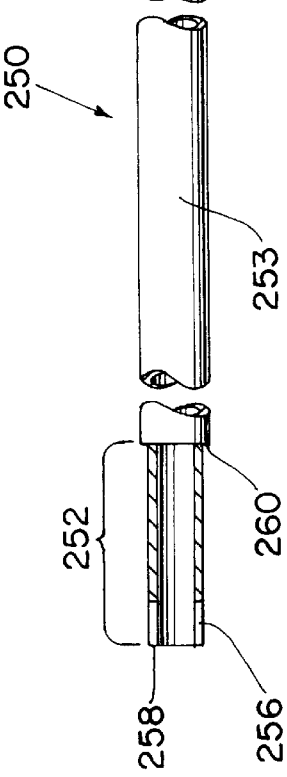

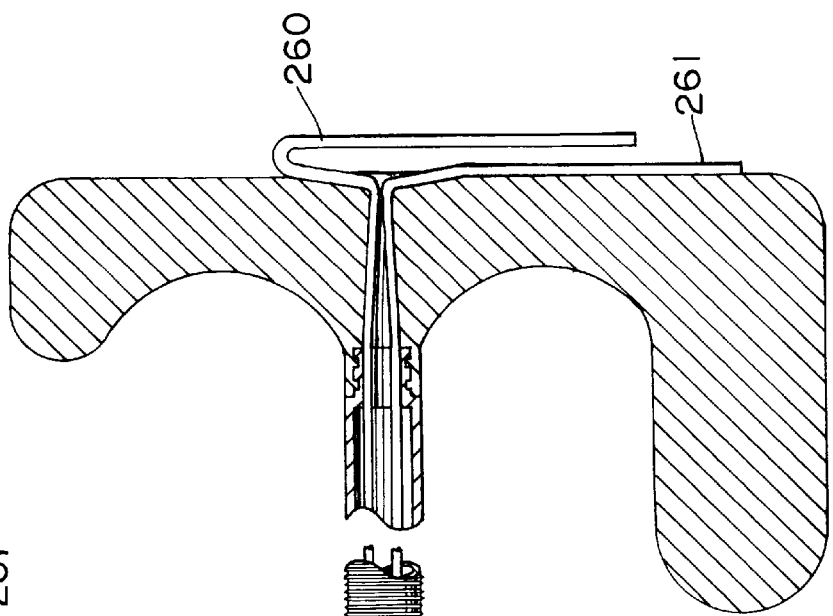
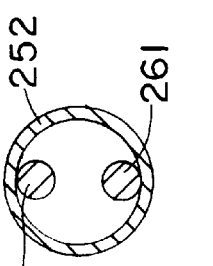
Fig. 35
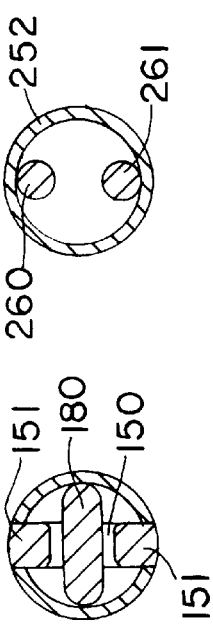
Fig. 34
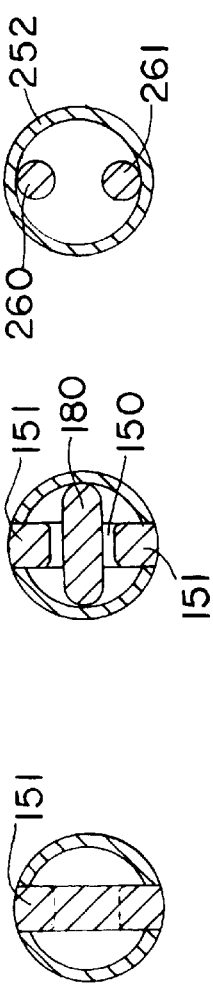
Fig. 33
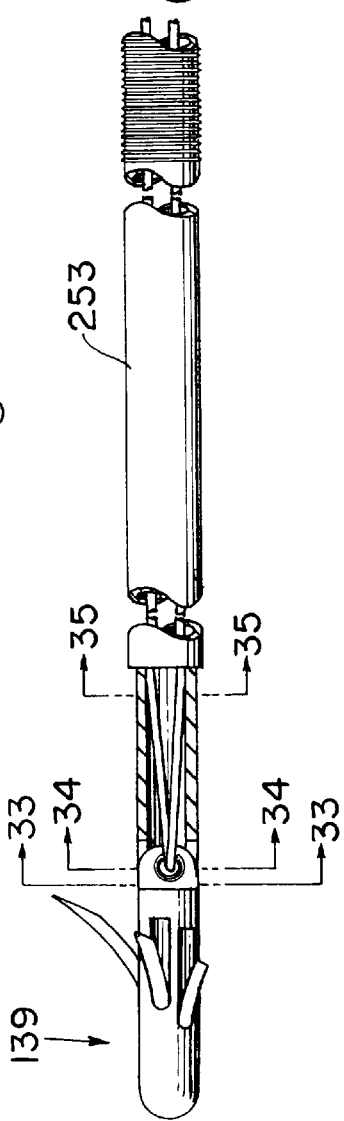
Fig. 32

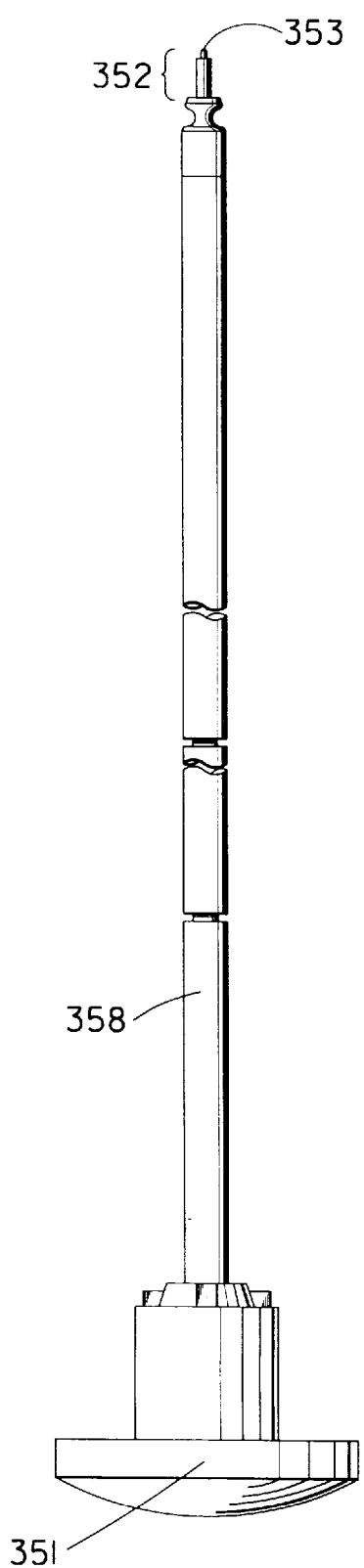
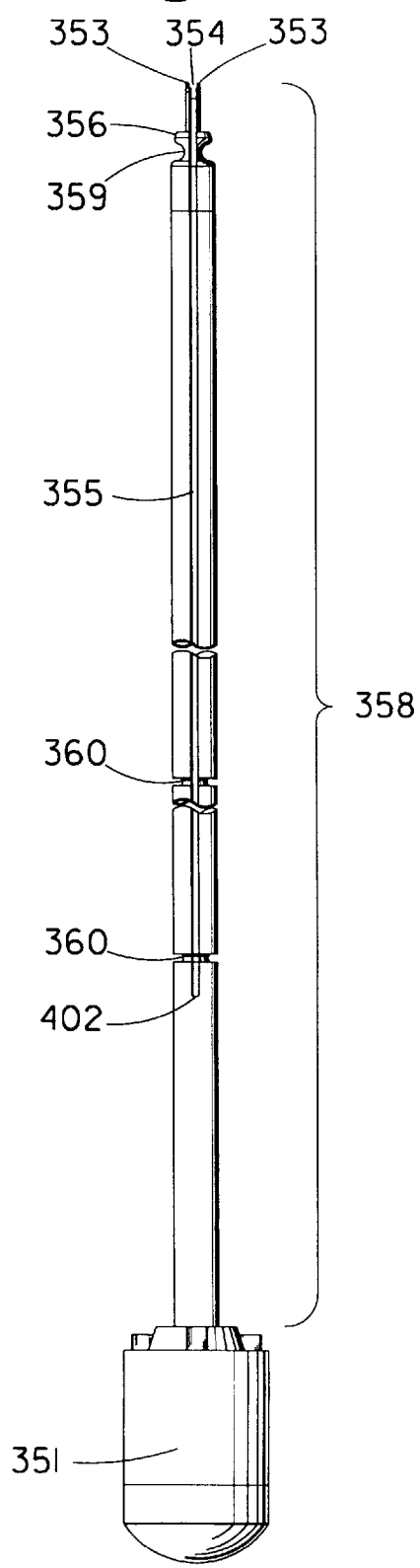

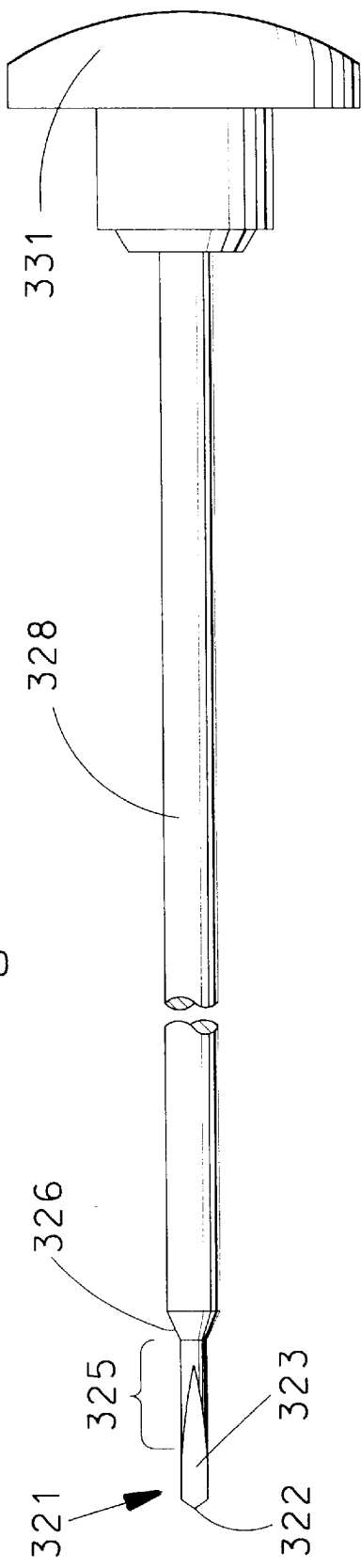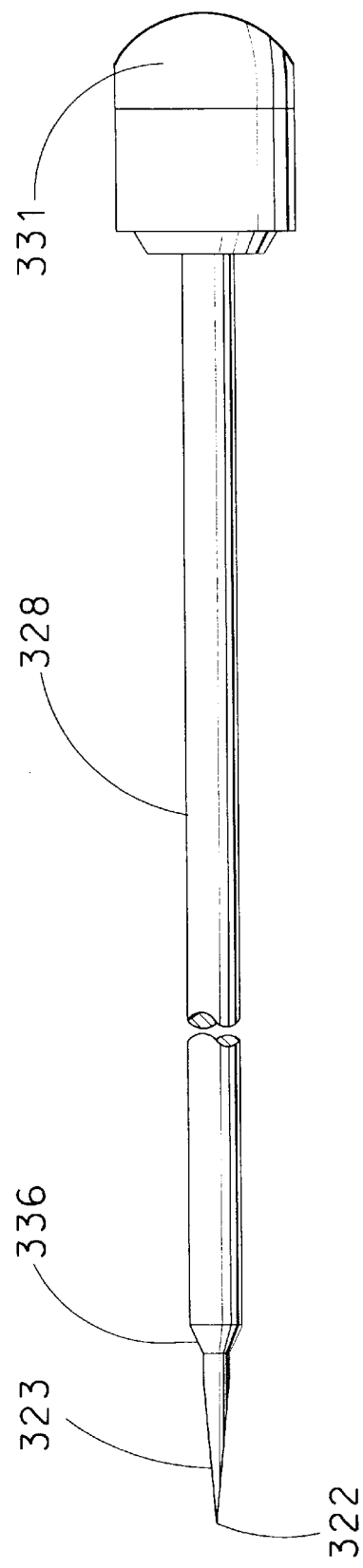

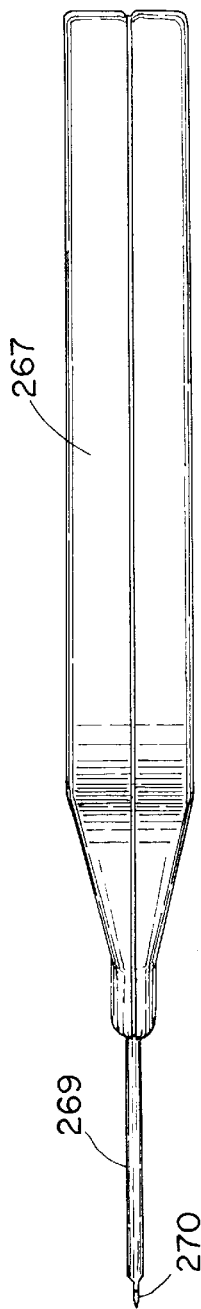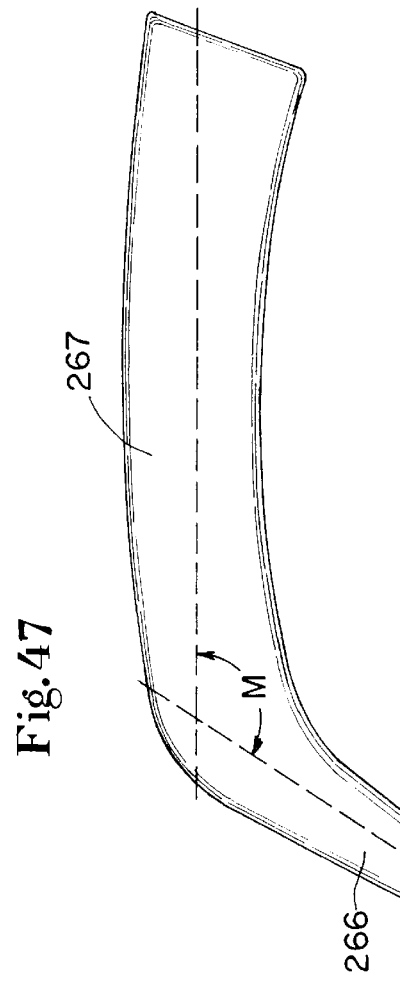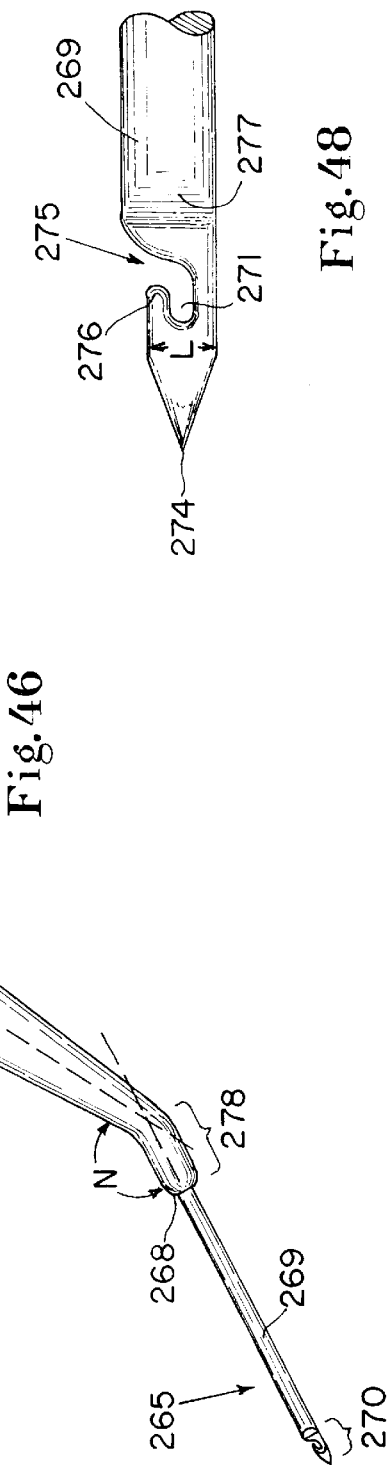
Fig. 47
Fig. 46
Fig. 48

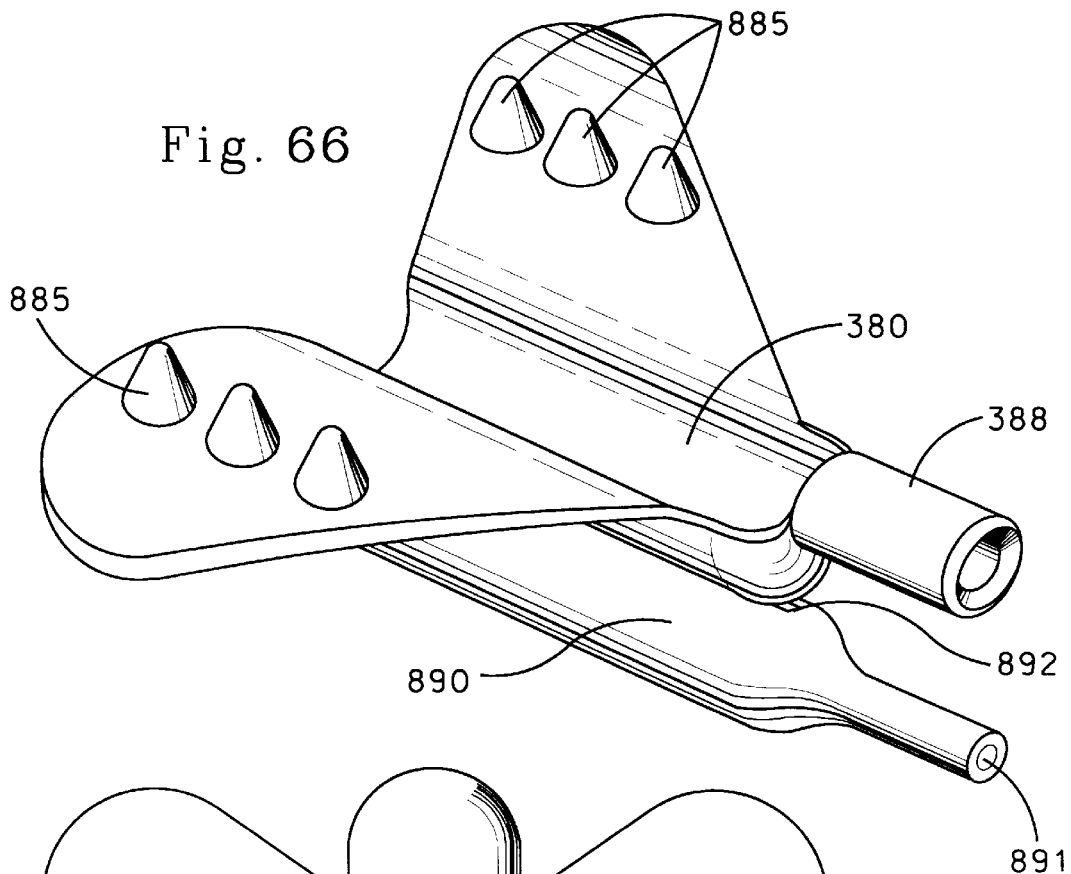
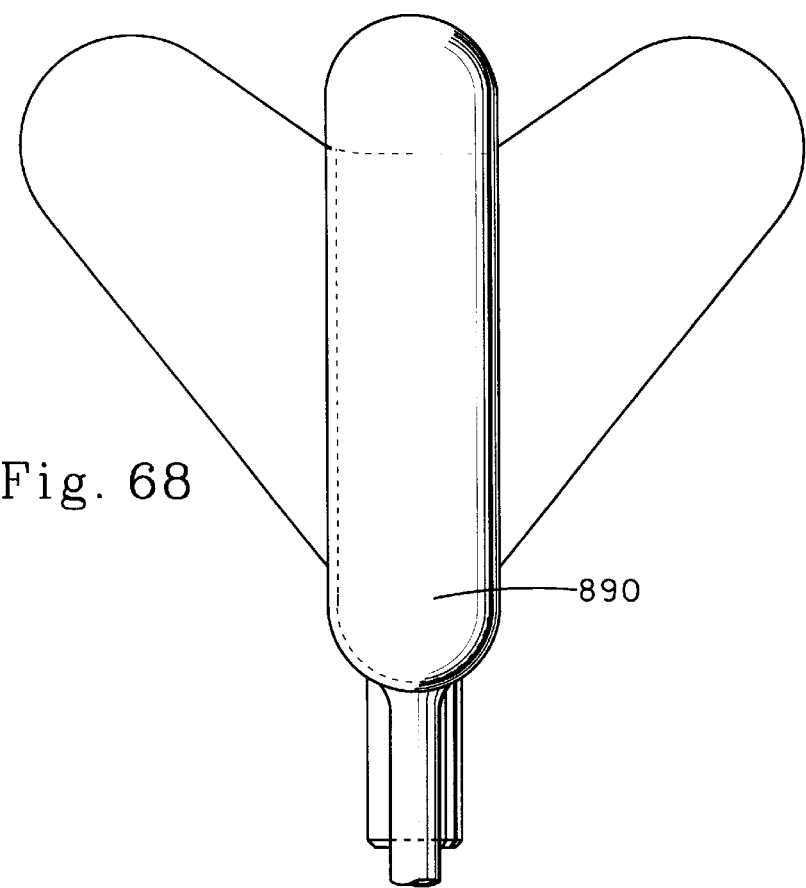

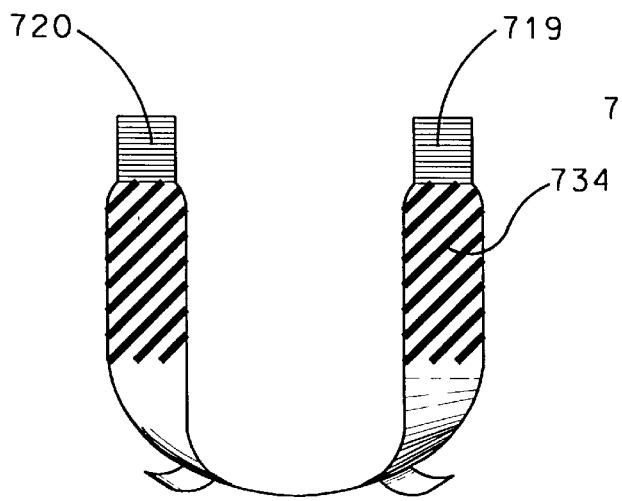
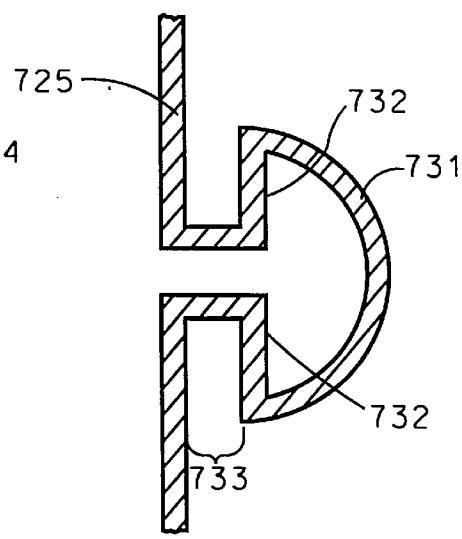
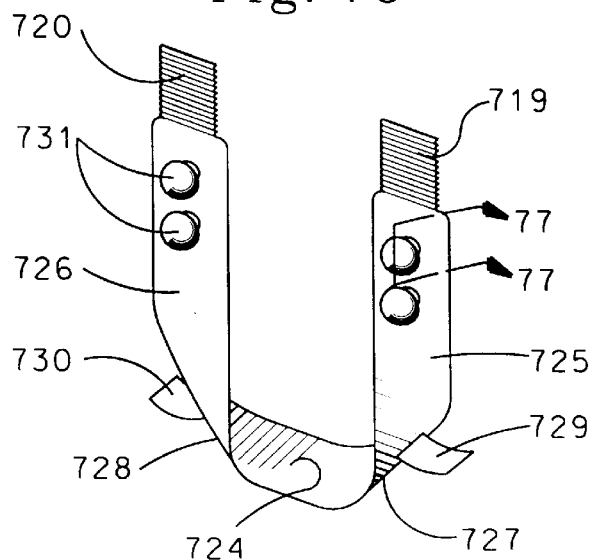
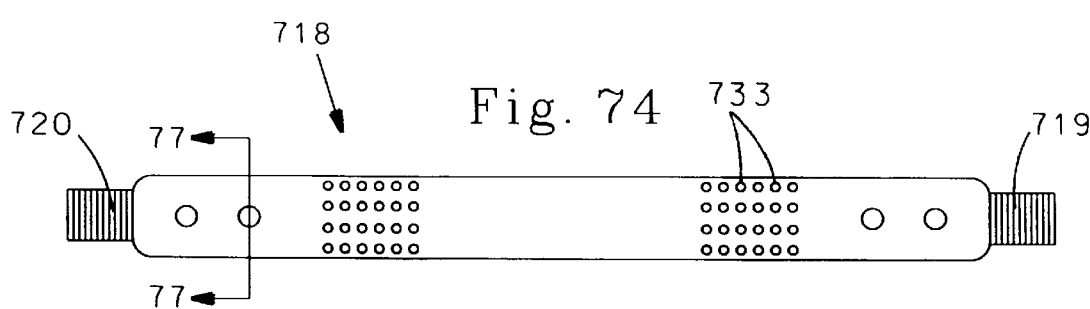

SURGICAL TEMPLATE AND SURGICAL METHOD EMPLOYING SAME

CROSS-REFERENCES TO RELATED APPLICATIONS

This application is a continuation-in-part of application Ser. No. 08/490,281, which was filed on Jun. 14, 1995, now U.S. Pat. No. 5,697,931.

BACKGROUND OF THE INVENTION

1. Field of the Invention

The present invention is directed towards a surgical template for use in gynecological procedures, as well as surgical methods employing this template. More particularly, the present invention provides apparatus and methods for ensuring proper placement of a fixation device during gynecological procedures, such as procedures for the correction of female stress urinary incontinence. An urethral sling which may be used in conjunction with the template is also provided.

2. Description of Related Art

Female stress urinary incontinence (SUI), defined as the unintentional loss of urine, can be a socially unacceptable problem for many women. Most often, the incontinence occurs during coughing, sneezing, or physical activity in women afflicted with this problem. While effective surgical treatment for this condition has existed for nearly 50 years, the procedures typically involve major abdominal surgery with accompanying post-operative limitations lasting six to eight weeks. Because of the nature of these surgical procedures, many women simply resort to diaper-like incontinence pads, or simply avoid any activities which result in the unintentional loss of urine.

In the normal resting state, the external pressure exerted on the collapsible urethra by the surrounding musculature is greater than the pressure exerted on the bladder, and therefore continence is maintained. During moments of coughing, sneezing, or physical activities, greater pressure will be exerted on the dome of a filled bladder. In women not afflicted with stress incontinence, a corresponding increase in the external pressure on the urethra acts to prevent the unwanted loss of urine from the bladder. Sufferers of SUI, however, aren't so fortunate.

Stress urinary incontinence is generally caused by two anatomic etiologies: intrinsic sphincter deficiency ("ISD"); and a loss of support of the periurethral tissue at the urethra-vesicular junction ("UVJ"—the region where the urethra enters the bladder). The latter situation (also known as hypermobile bladder neck) often occurs after childbirth, and is caused by a separation of the connective tissue which secures the periurethral tissue to the underside of the pubic bone. When this occurs, the UVJ will sag into the vagina, thereby reducing the pressure which can be exerted on the urethra during moments of stress. Diagnosis of any sagging of the UVJ can be easily determined by inserting the tip of a cotton swab into the urethra until it reaches the UVJ. The patient is then asked to bear down as if urinating, and loss of the UVJ support is readily identified by the upward movement of the wooden end of the cotton swab. In this test, the external urethral meatus acts as a fulcrum for the tip of the swab, and the elevation of the opposite end indicates the downward descent of the UVJ. U.S. Pat. No. 4,072,144 provides an alternative device which may be utilized to readily measure the angle of the UVJ in a similar manner.

ISD, on the other hand, is a functional problem in that the detrusor muscle (also known as the urethral sphincter) does not respond to sudden increases in intra-abdominal pressure. ISD can be caused by muscular withering with age, arteriosclerosis, diabetes, or prior incontinence surgery, all of which are related to a compromised blood supply to the detrusor muscle surrounding the urethra.

It is estimated that 10% of all incontinence is attributable to ISD, and the incidence of ISD is likely to increase as the population ages. For both types of stress urinary incontinence, however, various types of surgical procedures have been developed which often provide relief.

Various "urethropexy" procedures (often referred to as retropubic bladder neck suspension) fix or secure a portion of the tissue adjacent the patient's urethra (also referred to as the periurethral tissue) relative to a structure within the patient's body by means of a fixation device. The first urethropexy procedure for eliminating SUI caused by a sagging urethra was developed in 1948 by Drs. Marshall, Marchetti, and Krantz, and generally involves the fixation of the periurethral tissue at the UVJ on either side of the urethra (MMK procedure). Fixation in the MMK procedure, also known as abdominal culposuspension, is accomplished by suturing the periurethral fascia at the UVJ on either side of the urethra to the periosteum of the pubic bone. The procedure essentially alters the angular relationship between the urethra and bladder by elevating the UVJ, and therefore preventing the sagging of the UVJ when downward pressure is applied to the region by various stresses. The MMK procedure has been perfected by others over the years, however the essential principles have remained the same. Unfortunately, prior to Applicant's work, MMK procedures could only be performed via a large abdominal incision (referred to as an "open" procedure).

In 1955 Burch developed the urethropexy procedure of affixing the periurethral fascia bilaterally to Cooper's ligament, rather than the periosteum of the pubic bone, thereby resulting in a technically easier procedure because of the previous difficulties in passing a needle through the periosteum of the pubic bone. Although the Burch procedure has been performed laparoscopically, the five-year failure rate for the open Burch procedure is approximately 80%. A laparoscopic Burch procedure can be even more problematic since it is extremely difficult and time-consuming to tie sutures laparoscopically. Both the MMK and Burch procedures are referred to as retropubic suspensions.

Alternatively, needle suspension procedures such as those of Pereyra (West. J. Surg., 67: 223, 1959), Stamey (*Surg., Gynec. & Obst.*, 136: 547, 1973), Raz (*Urology*, 17: 82, 1981), Gittes (*J Urol.*, 138: 568, 1987) and Benderev (*J. UroL*, 152: 2316, 1994) have been developed for the correction of hypermobile bladder neck. In most of these procedures, a long needle having a suture attached thereto is passed into the abdominal cavity, through the space of Retzius, and through a portion of the periurethral tissue. Several bites of periurethral tissue are usually taken, and anterior fixation of the suture is accomplished by either securing the suture to the rectus fascia or by securing the suture to a bone anchor in the anterior pubis (as in the Benderev procedure). The needle and accompanying suture may or may not enter the vagina, depending upon the procedure and type of needle employed. Multiple passes of the needle through the periurethral tissue are usually employed, and the suture is usually weaved through the periurethral tissue in a helical pattern (or any of a variety of other patterns).

Although needle suspension procedures are often much quicker and simpler than the retropubic MMK and Burch procedures, the long-term failure rate is significantly higher.

The gynecological procedures of MMK, Burch and others have proven to be the most effective. This is reputedly due to the lack of retropubic dissection in the needle suspension procedures and the subsequently absent post-operative fixative scarring in the space of Retzius. Scarring of the urethra and periurethral fascia to the undercarriage of the pubic bone also aid in fixation of all of the involved tissues during the MMK and Burch procedures, thereby assisting in the prevention of incontinence. Although these problems could perhaps be rectified by dissection of the space or Retzius during needle suspension procedures in order to promote the growth of fixative scar tissue in this region, such dissection is not always practical when one is attempting to minimize the invasiveness of the procedure by performing a needle suspension.

Failure also occurs because of suture pull-out, which is often caused by the surgeon's failure to take a sufficient bite of periurethral tissue when passing the needle therethrough. Needle suspensions are usually blind procedures which require the passing of long needles through the rectus fascia to the periurethral fascia utilizing a cystoscope or by using the underside of the pubic bone as a guide for the needle. A finger pressed against the vaginal wall may also be used to guide the passing of the needle into the vagina. Although these urological procedures avoid the 10-centimeter midline or Pfannenstiel incision and its' required three-day or longer hospital stay in the open procedures, it is often difficult for the surgeon to locate the proper location in the periurethral tissue through which the sutures should be passed. More significantly, the long needle may inadvertently pass into the bladder or the ureters despite transurethral endoscopic vision. Thus, the inappropriate or nonspecific placement of periurethral sutures contributes to the long-term failure rate of needle suspensions, and can also be directly responsible for interoperative and post-operative complications.

Recently, a modified version of the MMK procedure has been developed which utilizes bone anchors secured directly to the pubic bone on either side of the symphysis for fixation of the UVJ. The apparatus for performing this modified MMK procedure are sold by Mitek Surgical Products, Inc. of Norwood, Mass., and a number of U.S. patents concern these products (see, e.g., U.S. Pat. Nos. 5,207,679, 5,217,486 and 4,899,743). In the Mitek-MMK procedure, a Pfannenstiel incision must be made in the abdomen in order to provide access to the space of Retzius. The space of Retzius is in actuality a "potential" space in that it contains various connective tissues and fats which must be dissected in order to provide sufficient access to this region. In fact, this connective tissue, particularly the areolar adventitial tissue, generally breaks down after vaginal delivery of a child, and this breaking down of the connective tissue often contributes to the onset of SUI in many women.

Once the space of Retzius has been dissected in the Mitek-MMK procedure, small anchors are secured in the pubic bone on either side of the pubic symphysis. Each of the bone anchors has a suture attached thereto, and these sutures are threaded through the periurethral tissue on either side of the urethra. The sutures are then tied off in the abdomen so that the periurethral tissue is pulled upward, which in turn restores the angle of the urethra at the UVJ, thereby restoring the urethra to its proper location. While the Mitek-MMK procedure is highly effective, it is a lengthy and complicated procedure which can generally only be performed by highly-skilled surgeons.

More recent advances in needle suspension procedures include those developed by Theodore Benderev and marketed by Vesica Medical, Inc. of San Clemente, Calif. This procedure is discussed in U.S. Pat. Nos. 5,544,664 and 5,582,188, all of which are incorporated herein by reference. The Benderev procedure differs from most other needle suspensions in that, like the Mitek-MMK procedure, a bone anchor may be used to attach the fixation device (in this case a suture) to the pubic bone. Unlike the Mitek-MMK, however, the bone anchors are secured to the anterior pubis (the topside of the pubic bone), thereby providing a minimally-invasive procedure. In the Benderev procedure, however, the suture extending from the anchor is once again passed blindly from the abdominal cavity into the vagina, thereby complicating proper suture placement.

In all of the above procedures, the fixation device (i.e., the suture) remains permanently within the patient. Scar tissue, however, will form about the fixation device, thereby reattaching a portion of the periurethral tissue directly to the supporting structure (e.g., the pubic bone). When the incontinence is caused by ISD or when the support tissues in the bladder neck area are irreparably damaged, however, the above-described procedures are not the recommended treatment. In these circumstances, a urethral sling procedure (also known as a pubovaginal or suburethral sling procedure) may be employed. In the "sling procedure", a urethral sling comprising a strip of flexible material acts as the fixation device. One end of the sling is typically sutured to the anterior rectus fascia, and the other end is then slung beneath the urethra and likewise sutured to the anterior rectus fascia. In this manner, incontinence is corrected due to the elevation of the UVJ and the compression of the urethra against the symphysis pubis. Similarly to the bladder neck suspension procedures, proper placement of the sling through the periurethral tissue is critical to the success of this procedure, and therefore the incisions in the periurethral tissue through which the sling passes must be precisely located.

The present invention provides a surgical template which may be employed to direct proper placement of a fixation device during a gynecological procedure. The template of the present invention may be employed, with slight modifications to its configuration, in any gynecological procedure wherein a fixation device is connected to a portion of the tissue adjacent the vagina (preferably the periurethral tissue), including bladder neck suspensions (both retropubic and needle suspensions), as well as vaginal sling procedures. In addition, the template of the present invention may be employed in both traditional open procedures as well as recently-developed laparoscopic procedures. By way of example, the template of the present invention may be employed in the MMK, Burch, needle suspension (including Benderev) and sling procedures described above.

BRIEF DESCRIPTION OF THE DRAWINGS

While the specification concludes with claims particularly pointing out and distinctly claiming the present invention, it is believed that the same will be better understood from the following description taken in conjunction with the accompanying drawings in which:

FIG. 3 is a top plan view of a bone anchor used in the method of the present invention;

FIG. 4 is a side plan view of the bone anchor of FIG. 3;

FIG. 5 is a top plan view of a drill tamper tool of the present invention wherein a portion of the tool has been broken-away;

FIG. 6 is a side plan view of the tamper tool of FIG. 5;

FIG. 7 is an end plan view of the tamper tool of FIG. 5, taken along line 7—7 thereof;

FIG. 8 is a top plan view of a bone anchor insertion tool of the present invention, wherein a portion of the tool has been broken-away;

FIG. 9 is a side plan view of the insertion tool of FIG. 8;

FIG. 10 is a side plan view of the insertion tool of FIG. 8 with the bone anchor of FIG. 3 loaded thereon;

FIG. 11 is a side plan view of a suture retriever of the present invention;

FIG. 12 is an end plan view of the suture retriever of FIG. 11, taken along the line 12—12 thereof;

FIG. 31 is a side plan view of an anchor-insertion tool of the present invention, wherein a portion of the tool has been cut-away for clarity;

FIG. 32 is a side plan view of the anchor-insertion tool of FIG. 31 with an anchor loaded thereon, said anchor having a suture extending therefrom, wherein a portion of the tool has been cut-away or cross-sectioned for clarity;

FIG. 33 is a cross-sectional view of the loaded anchor-insertion tool of FIG. 32 taken along line 33—33;

FIG. 34 is a cross-sectional view of the loaded anchor-insertion tool of FIG. 32 taken along line 34—34;

FIG. 35 is a cross-sectional view of the loaded anchor-insertion tool of FIG. 32 taken along line 35—35;

FIG. 36 is an end plan view of the handle of the anchor-insertion tool of FIG. 31.

FIG. 37 is a top plan view of yet another embodiment of the anchor-insertion tool of the present invention, wherein a portion of the shaft has been broken away;

FIG. 38 is a side plan view of the anchor-insertion tool of FIG. 37;

FIG. 44 is a top plan view of another embodiment of the drill tamper tool of the present invention, wherein a portion of the shaft has been broken away;

FIG. 45 is a side plan view of the drill tamper tool of FIG. 44;

FIG. 46 is a side plan view of another embodiment of the suture retriever of the present invention;

FIG. 47 a top plan view of the suture retriever of FIG. 46;

FIG. 48 is a side plan view of the retrieving end of the suture retriever of FIG. 46;

FIG. 66 is a perspective view of another template embodiment according to the present invention;

FIG. 68 is a bottom plan view of the template of FIG. 66;

FIG. 74 is a top plan view of the sling of the present invention, wherein the molded twists have been removed for clarity;

FIG. 75 is a side plan view of the sling of FIG. 74;

FIG. 76 is a perspective view of the sling of FIG. 74;

FIG. 77 is a cut-away side view of a portion of the sling of FIG. 74; and

SUMMARY OF THE PREFERRED EMBODIMENTS

Figure 1:
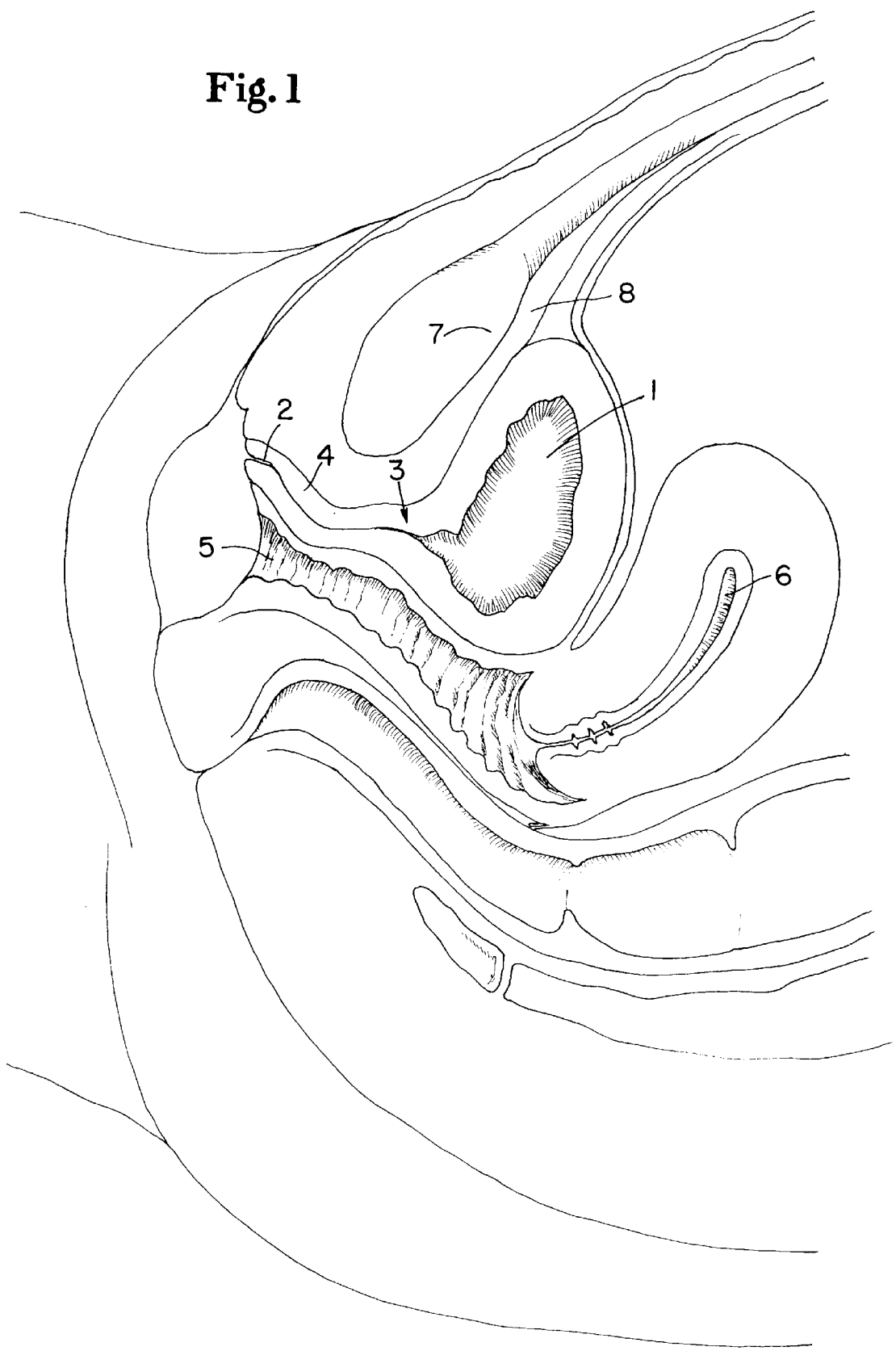
FIG. 1 is a cross-sectional view taken through the midline of a patient who has lost support of the periurethral tissue at the UVJ, and is thereby suffering from stress urinary incontinence (SUI)

It is an object of the present invention to provide a surgical template for use in directing placement of a fixation device.

It is another object of the present invention to provide a surgical method for connecting at least a portion of the tissue adjacent a patient's vagina relative to a structure within the patient's body employing a template to guide placement of a fixation device.

It is yet another object of the present invention to provide such a template, wherein the alignment of the template within the vagina of a patient is directed by an anatomical structure within the patient's vagina, thereby ensuring proper placement of a fixation device.

It is still another object of the present invention to provide an urethral sling.

The forgoing object can be accomplished, in accordance with one aspect of the present invention, by providing a template for guiding the placement of a fixation device during a surgical procedure, the template comprising:

(a) a body portion; and (b) at least one guide disposed in a predetermined spacial relationship to the body portion;

wherein the template is configured such that at least a portion of the template may be aligned within the vagina of a patient such that the guide may be employed to direct the placement of a fixation device or other medical instrument through at least a portion of the tissue adjacent the vagina. The template is preferably configured such that when the template is aligned within the vagina, the at least one guide may be employed to direct placement of a fixation device or other medical instrument through at least a portion of the tissue adjacent the vagina in a predetermined relationship to a landmark (such as the urethra or more particularly the UVJ) within the patient's body. In essence, the template is configured such that a portion of the anatomical structure of a patient's vaginal region (such as the urethra, and/or the periurethral tissue beneath the urethra, and/or the UVJ), directs alignment of the template. The template is configured such that alignment of the template at least partially within a vagina of a patient is directed by a portion of the anatomical structure of the patient's vaginal region (such as the urethra).

In a preferred embodiment, the body portion of the template comprises an arcuate trough and an alignment member. The template may also comprise one or more wing members, wherein the guides are provided thereon. The template may also comprise an elongate member which may be inserted into a patient's urethra for alignment purposes. This elongate member may comprise, for example, a Foley catheter which is attached to the template body by means of an alignment member. Other types of elongate members may be employed, however, including other types of catheters. The body of the template may further comprise a trough of arcuate cross-section, such that the urethra and periurethral tissue beneath the urethra can nest within this trough to provide proper alignment of the template. The axis of the alignment and elongate members are preferably parallel and above the axis of the trough. When two wing members are employed they preferably extend away from opposite sides of the trough such that they will be positioned against the upper vaginal wall (i.e., the vaginal mucosa) adjacent the urethra (i.e., the periurethral tissue).

The at least one guide may be chosen from the group consisting of: an aperture, a slot, a notch, a protrusion and a visible indicia (such as a light source or markings). For example, a beam of light may be projected from the light source through a predetermined region of the periurethral tissue, thereby transilluminating the predetermined region of the periurethral tissue for placement of the fixation device. The light source may even be provided on a protrusion, and can comprise a translucent region through which a beam of light is projected. The at least one guide can also comprise a protrusion, wherein the template is configured to be alignable within the vagina of a patient such that the protrusion will displace a predetermined region of the periurethral tissue of the patient which can be visualized from within the abdominal cavity of the patient. Preferably, multiple protrusions extend away from the topside of a pair of wing members.

The at least one guide may alternatively comprise a slot sized so as to permit a cutting tool to be inserted therethrough in order to create an incision in the periurethral tissue of a patient during a continence procedure. The slot is preferably positioned on a wing member such that the template may be aligned within the vagina of a patient with the slot extending substantially parallel to the patient's urethra. The at least one guide member may also comprise an aperture through which a fixation device may be passed during a urethropexy procedure.

Preferably, at least two of the apertures are provided, and they are connected to one another by a slit. A removable support strut may also be positioned on the wing member so as to block communication between the adjacent apertures.

A portion of the template may also be expandable such that at least the expandable portion of the template may be inserted into a patient's vagina in an at least partially unexpanded condition, and thereafter expanded so as to urge the expandable portion against the interior wall of the vagina and to urge the at least one guide against a predetermined region of the periurethral tissue. This expandable portion may comprise an inflatable balloon attached to the underside of the trough, and may be inflated to urge the protrusions against the upper vaginal wall.

A surgical method of connecting at least a portion of the tissue adjacent a patient's vagina relative to a structure within the patient's body is also provided. This method comprises:

(a) providing a vaginal template, the template having at least one guide for ensuring proper positioning of a fixation device;

(b) aligning at least a portion of the template within the vagina of a patient; and (c) connecting a portion of the tissue adjacent a patient's vagina relative to a structure within the patient's body with a fixation device by:
   connecting one portion of the fixation device relative to the structure within the patient's body; and
   passing another portion of the fixation device through at least a portion of the tissue adjacent the patient's vagina, using the guide to direct placement of the fixation device through the tissue.

The fixation device may comprise a filamentatious member (such as suture, thread or wire), or an urethral sling. The structure within the patient's body is chosen from the group consisting of: the pubic bone, the periosteum of the pubic bone, the pubic symphysis, Cooper's ligament, and the rectus fascia. The fixation device may be sutured directly to the structure, or secured relative thereto by another device such a bone anchor or rivet. Preferably, the template is used to guide placement of the fixation device through at least a portion of the periurethral tissue, and may or may not pass into the vagina.

Finally, an urethral sling for use in a surgical procedure to correct incontinence is provided, the sling comprising a strip of flexible material having a central portion, and a pair of side portions extending away from either side of the central portion, each of the side portions positioned in twisted relationship to the central portion such that each of the side portions extends perpendicularly away from the surface of the central portion.

DETAILED DESCRIPTION OF THE INVENTION

The first portion of this Application describes a laparoscopic urethropexy procedure developed by Applicant. A surgical template employed in this procedure is also described. This template, however, may be readily employed in a variety of gynecological procedures, particularly where a fixation device is to be passed through at least a portion of the tissue adjacent the vagina. The phrase "tissue adjacent the vagina" is intended to include any portion of the vaginal wall as well as the tissue adjacent thereto. In particular, the template of the present invention may be used in procedures wherein a fixation device is passed through at least a portion of the periurethral tissue (i.e., the tissue adjacent the urethra), including the periurethral fascia. As will be understood, while the configuration of the template can be modified to provide for proper placement of the fixation device during a variety of procedures, the underlying principles remain the same. The last portion of this application will describe these variations in template configuration an scope, all of which are within the scope of the present invention.

Referring now to the drawings in detail, wherein like numerals indicate identical elements throughout the views, FIG. 1 is a cross-sectional view taken along the midline of a patient suffering from stress urinary incontinence (SUI) of the hypermobile bladder neck type. For reference, FIG. 1 depicts bladder 1, urethra 2, urethra-vesicular junction (UVJ) 3, periurethral tissue 4, vagina 5, uterus 6, pubic symphysis 7, and space of Retzius 8. In this patient, urethra 2 and the associated periurethral tissue 4 have sagged into vagina 5. During periods of stress such as coughing or sneezing, pressure will be exerted on bladder 1. Due to the collapse of urethra 2, the surrounding musculature will be unable to provide sufficient counteractive pressure on urethra 2 to prevent loss of urine during these periods of stress. As known from the methods of the prior art, particularly the MMK procedure, fixation of periurethral tissue 4 at UVJ 3 on either side of urethra 2 will act to support the urethra and prevent the sagging of urethra 2 into vagina 5. This in turn will enable the surrounding musculature to provide sufficient pressure on urethra 2 to prevent loss of urine during moments of stress.

Figure 2:
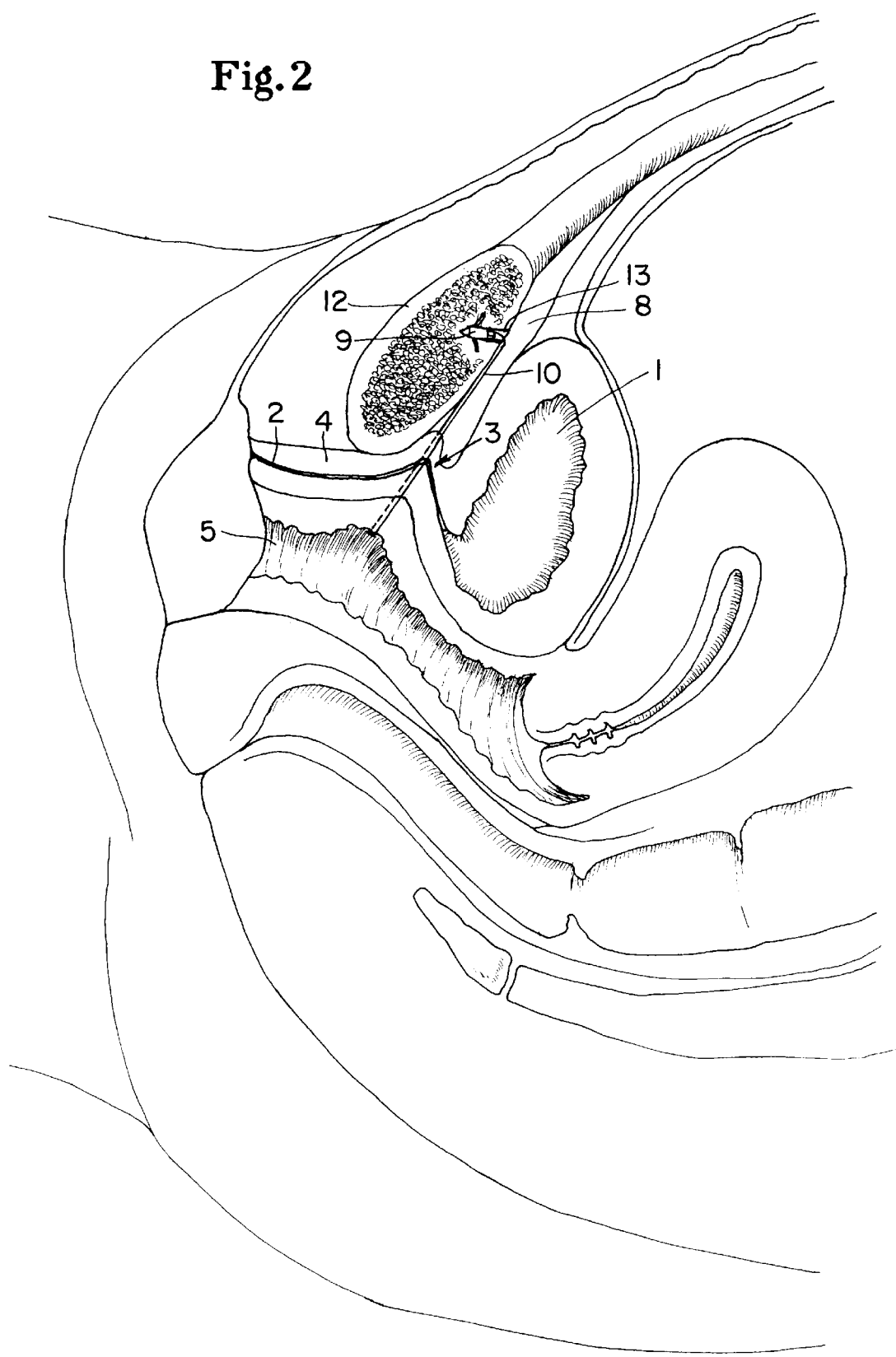
FIG. 2 is the same view as FIG. 1, however the structural defect has been corrected using the methods and apparatus of the present invention.

FIG. 2 depicts the resulting support of urethra 2 at UVJ 3 by means of a retropubic bladder neck suspension procedure using the template of the present invention. It should first be noted that pubic bone 12 is shown in FIG. 2, and is that portion of the pubic bone lying immediately to the right of the pubic symphysis 7. As will be more fully understood later, the anchors of the present invention are secured in the pubic bone on either side of the pubic symphysis. A bore 13 has been produced in pubic bone 12, and anchor 9 has been secured within bore 13 It should be noted that bore 13 and anchor 9 have been enlarged for purposes of clarity. A suture 10 is secured to anchor 9, and the two tails of suture 10 extend downwardly through the space of Retzius 8 into vagina 5. The tails of suture 10 extend into the vagina immediately to the right of urethra 2 through periurethral tissue 4 at UVJ 3. In the vagina, the two tails of suture 10 are tied to one another such that suture 10 provides an upward force on periurethral tissue 4 on the right side of urethra 2 adjacent UVJ 3. An identical anchor and suture combination is secured to the pubic bone on the left side of the pubic symphysis, and the suture enters the vagina in a similar fashion as before in order to provide an upper force on periurethral tissue 4 on the left side of urethra 2. In this fashion, the sutures on either side of the urethra act to restore the angle of the urethra at the UVJ.

It should be noted that although sutures are the preferred fixation device for Applicant's laparoscopic urethropexy procedure, other fixation devices may be employed with the template of the present invention and will be described in more detail below. In all of these procedures, however, the fixation device connects a portion of the tissue adjacent the vagina relative to a structure within the patient's body. The fixation device may be attached directly to the structure (such as by threading the suture through Cooper's ligament or the periosteum of the pubic bone), or it may be attached to another device which is in turn secured to a structure within the body (e.g., a suture attached to a bone anchor which is secured to the pubic bone). Thus, connecting the tissue "relative to a structure within the patient's body" simply means that the tissue adjacent the vagina (such as the vaginal wall or periurethral tissue, including the periurethral fascia) is connected in a fixed relationship to this structure. This can include a simple suture extending between the tissue and the structure of the body (such as Cooper's ligament, the rectal fascia, the periosteum of the pubic bone, or even the pubic symphysis), regardless of whether or not the suture has the ability to move relative to the tissue or the fixative structure. Alternatively, the suture or other fixation device may be secured to the structure within the body using one or more anchoring devices (such as a bone anchor). In these cases, the fixation device is secured to an anchoring device which is in turn secured to the structure within the body; hence, the phrase "relative to a structure within the patient's body."

As will be described in further detail below, in Applicant's laparoscopic urethropexy procedure, the securing of the anchors to pubic bone 12 can be accomplished laparoscopically. Suture 10 may then be pulled into vagina 5 through periurethral tissue 4 immediately adjacent to urethra 2. The two tails of suture 10 are then tied to one another within vagina 5 by hand. It has been found that the portion of suture 10 positioned within vagina 5 will be epithelialized within a few days after the procedure. In this fashion, suture 10 will not cause any discomfort or irritation to the patient since suture 10 will quickly be covered by the epithelium of vagina 5. In place of suture 10, other filamentatious fixation devices may be used, including threads or wires.

Surgical Technique for Laparoscopic Urethropexy

It should be noted that although this first section describes apparatus and methods for performing a laparoscopic urethropexy procedure, the apparatus and methods are not so limited. For example, the novel bone anchor design described herein may be used in any of a variety of procedures.

A. Preparatory Procedures

Identification of patients suitable for the techniques of the present invention may be made by any of the known techniques for identifying patients amenable to SUI correction by MMK or similar retropubic urethropexy procedures. For example, as discussed previously a cotton swab may be inserted into the urethra until the end of the swab reaches the UVJ. The patient is then asked to bear down and the movement of the portion of the swab outside of the urethra is monitored. The external urethral meatus will act as a fulcrum for the cotton swab, and a loss of urethral support at the UVJ can be readily identified by the upward movement of the external end of the cotton swab. This indicates a downward descent of the urethra at the UVJ, which in turn provides an indication of the structural cause of the patient's SUI. Other means known in the art, however may be employed to confirm the diagnosis and/or to rule out other possible causes.

The preoperative preparation of the patient follows standard procedures for laparoscopic and gynecological surgeries, however no enema is needed. The patient is placed in the dorsal lithotomy position, and standard parenteral antibiotics are applied. Preferably, the patient is also placed under general anesthesia in order to minimize discomfort.

Figure 17:
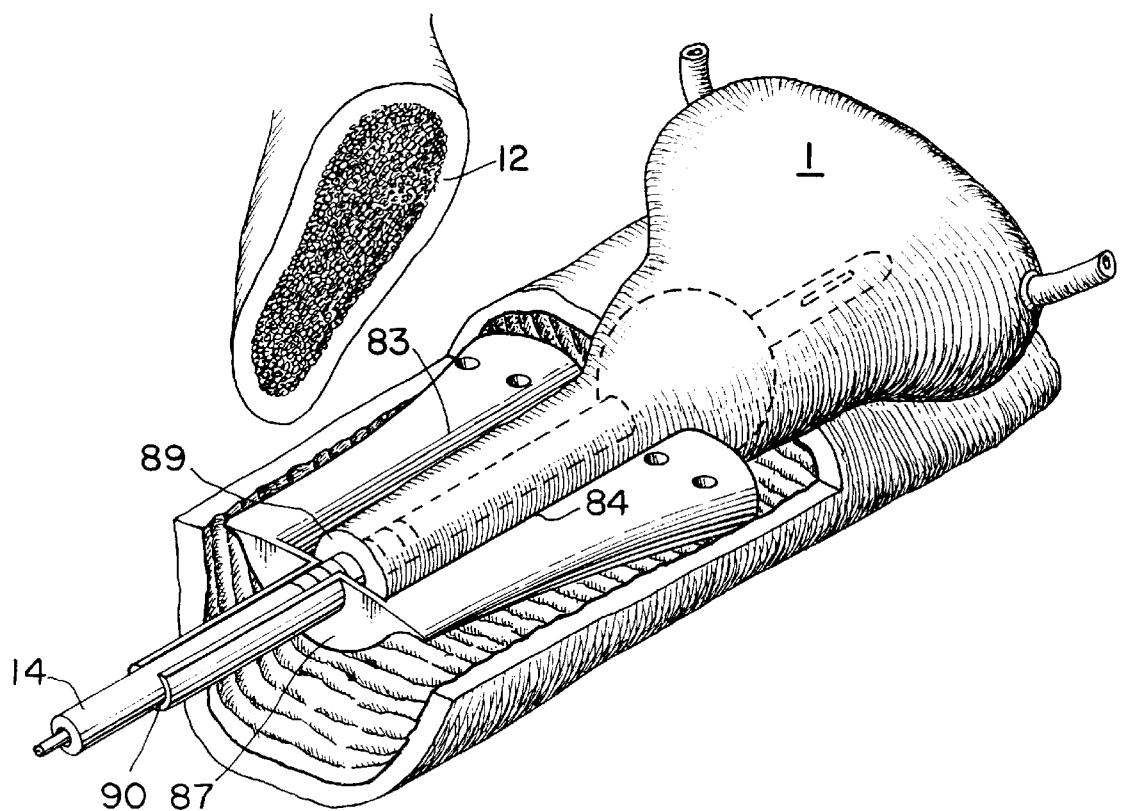
FIG. 17 is a perspective view of the template of FIG. 13 in use during a surgical procedure with portions of the patient's anatomy cut-away for clarity.

A Foley catheter (16 French with 10 cc balloon) is then inserted into the urethra. The balloon of the Foley catheter is inflated, and the catheter is gently pulled outwardly to ensure proper placement of the balloon at the juncture of the bladder and the urethra. Proper placement of Foley catheter 14 is shown in FIG. 17 wherein a portion of vagina 5 has been cut-away for purposes of clarity. Bladder 1 is thereafter drained in the usual fashion using the catheter so that the bladder will become deflated. As will be understood below, maintaining the bladder in a deflated state greatly simplifies the procedure of the present invention. In addition, when the template of the present invention is employed, it is preferable that Foley catheter 14 be positioned in the manner shown in FIG. 17 for reasons which will be described further herein.

It is also desirable to measure the length of the patient's urethra in order to ensure proper placement of the supporting sutures, particularly when the template of the present invention is employed. If the sutures are placed too close to the bladder, there is a considerable risk that the suture retrieving tool will puncture the bladder. Likewise, if the sutures are placed too far from the UVJ, then proper support of the urethra will not be accomplished. The length of urethra 2 may be readily measured by means of any suitable apparatus which may be inserted into the urethra, as long as the surgeon can be certain that one end of the device is positioned at the juncture of the bladder and the urethra (i.e., the UVJ). The simplest means of obtaining this measurement is to provide graduations along at least a portion of the length of Foley catheter 14, as shown in FIG. 17. In this fashion, when the balloon of the Foley is properly inflated within the bladder and the catheter pulled outwardly to ensure proper seating of the balloon at the juncture of the bladder and the urethra, the length of the urethra can be determined using the graduations which will be readily visible immediately adjacent the end of urethra 2. While the average urethra is 3 cm in length, this can often vary between about 2.7 and about 3.3 cm. As will be more fully understood below, the surgical template employed in the method of the present invention can thus be manufactured in different sizes to accommodate the differing urethra lengths. A minimum of two sizes for the template may be provided, and more preferably at least three different sizes. Alternatively, the graduations on the Foley catheter may be employed to facilitate proper placement of a single-sized template.

After the placement of Foley catheter 14 and drainage of bladder 1, an infra umbilical incision is made in the patient in order to provide access to the pre-peritoneal region (the area between the abdominal wall and the peritoneum), and more particularly space of Retzius 8. Surgical dissection of space of Retzius 8 is necessary in order to provide visual access to the pubic bone for placement of the bone anchors. Thus, dissection is performed below the fascia, thereby eliminating the adventitial or supportive connective tissue in space of Retzius 8. Although dissection of the connective tissue in space of Retzius 8 can be accomplished in the typical fashion through a laparoscope, Applicant has found that a balloon dissection procedure is simpler and more effective.

Balloon dissection can be accomplished using the SPACEMAKER surgical balloon dissector manufactured by General Surgical Innovations of Portola Valley Calif. and described in U.S. Pat. No. 5,496,345, which is herein incorporated by reference. Preferably, a balloon specific to dissection of the space of Retzius is employed, such as that described in my copending application having Ser. No. 08/754,494 (filed Nov. 20, 1996), which is incorporated herein by reference. Other equivalent devices can also be employed for this purpose. The SPACEMAKER device has a guide rod to which a small balloon is attached. The guide rod is inserted into the infraumbilical incision until the tip of the rod reaches the pubic symphysis in the space of Retzius (i.e., between the symphysis and the bladder). The balloon is then inflated in space of Retzius 8 by filling the balloon with approximately 300 cc of saline solution or other suitable fluid, thereby further deflating bladder 1 and separating the surrounding connective tissue in order to provide sufficient room in space of Retzius 8 for the fixation procedure of the present invention. The balloon is then aspirated and removed from the pre-peritoneal region.

Although the SPACEMAKER device has an integral trocar sleeve which may normally be left in the infraumbilical incision for placement of the laparoscope, the only size currently available is too small for the procedure of the present invention. Obviously a properly sized integral trocar sleeve could remain in the patient after removal of the deflated balloon. Alternatively, and as presently preferred, the SPACEMAKER device is removed in its entirety, and a larger 12 mm trocar is inserted into the infraumbilical incision. A 12 mm WOLF operating/laser laparoscope (preferably with a WOLF 50/50 beamsplitter camera) is inserted into the trocar sleeve. The pre-peritoneal region is then insufflated, preferably with $CO_2$ at a pressure between about 10 and about 30 mm Hg, thereby further expanding the space of Retzius and providing excellent laparoscopic vision in this region.

Although the balloon dissection procedure is highly effective, further dissection of the space of Retzius is typically necessary in order to provide the necessary access to the pubic bone and the periurethral tissue, and also to ensure adequate formation of postoperative scar tissue. Although this may be accomplished by means of a $CO_2$ laser or a electrocautery device through the laparoscope already inserted, it is presently preferred that an additional 5 mm trocar be inserted in the midline suprapubically. An irrigation/suction/bovie device (such as that manufactured by U.S. Surgical) is then inserted into the space of Retzius through the smaller trocar sleeve. It should be noted that the trocar sleeve, like the operative channel of the laparoscope, is cannula through which surgical instruments may be inserted. The irrigation/suction/bovie device will not only assist in further dissection of the space of Retzius, but will also provide the necessary irrigation and suction while the other instruments necessary for performing the present procedure are employed through the infraumbilical trocar sleeve. The result of further dissection is that vision far superior to the standard MMK or Burch procedures employing a full abdominal incision will be provided, since it is difficult in these procedures for the surgeon to see the underside of the pubic bone where the anchors must be placed without the surgeon placing his or her head on the stomach of the patient. In this fashion, unobstructed laparoscopic access to the pubic bone and the periurethral tissue necessary for performing the procedure of the present invention is provided.

B. Creation of Bore in Pubic Bone

It should initially be noted that the procedure of the present invention may be employed with any of a variety of bone anchors, provided that the anchor can be readily secured to the pubic bone and a suture or other fixation device can be attached thereto. It is presently preferred, however, that the MITEK bone anchors disclosed in U.S. Pat. No. 5,207,679 (herein incorporated by reference) be employed for this purpose. As discussed more fully herein, these anchors are secured in place by pressing them into properly-sized bores created in the pubic bone. Additional types of anchors include those disclosed in U.S. Pat. Nos. 5,522,845, 5,520,696, 5,192,303 and 5,527,342 (all of which are herein incorporated by reference). The Acufex Microsurgical, Inc., subsidiary of the American Cyanamid Co., of Stamford, Conn. also manufactures yet another type of anchor which may be employed in the surgical procedure of the present invention. Known as TAG anchors, the Acufex anchors are disclosed in U.S. Pat. Nos. 5,258,016, 5,100,417 and 5,224,946, which are also incorporated herein by reference. Yet another suitable bone anchor is that sold by Li Medical of Boston, Mass.

All of the above anchors are secured to bone by insertion into a bore previously created in the bone. Thus, the MITEK-MMK and related procedures require the use of either a mechanical drill or hand-operated awl in order to provide the bore for insertion of a bone anchor (such as those manufactured by Mitek Surgical Products, Inc.) into the pubic bone. While these devices may be readily employed with large abdominal incisions, they cannot be used through a laparoscope for a number of reasons. Most importantly, these tools must be sufficiently sharp to enable the surgeon to penetrate the hard outer layers of the pubic bone (periosteum and cortical bone). Since the field of vision through a laparoscope may be limited at times, however, it is very risky to employ such sharp implements as there is a tremendous risk of puncturing the bladder or other soft tissue in the operative area. In addition, as best show in FIG. 12, pubic bone 12 falls away from the laparoscope at an angle of approximately 45°. The angularity of pubic bone 12 therefore provides vision and operative difficulties which are overcome by the apparatus and methods of the present invention. Simply drilling into pubic bone 12 using prior art apparatus through the laparoscope is not advisable because the drill or awl tip will tend to slide downwardly during the drilling operation because of the manner in which pubic bone 12 angles downwardly away from the laparoscope. While the drill tip may eventually penetrate the hard outer periosteum of the bone, the drill may enter at an improper location or angle due to downward slippage of the drill tip. Ideally one would like to produce a bore in pubic bone 12 which is at an angle of approximately 45-degrees to the surface of the bone into which the bore is produced. This angle may, however, be between about 20 and about 60-degrees, to thereby provide sufficient support for the bone anchor to be placed in the bore thus produced.

Applicant has developed a novel method and apparatus for creating the required bores in the pubic bone through a laparoscope. The method and apparatus avoid the use of any sharp tips, while still enabling the surgeon to properly place the bores in the pubic bone without a risk of misalignment during the bore creation process. In order to produce the bore without a need for a sharp instrument, a laser is first employed to produce a cone-shaped crater in the pubic bone at the desired bore location. The crater is produced in the periosteum and cortical bone, thereby providing access to the soft cancellous, or tribecular, bone. In this fashion, a drill tamper tool (to be described further herein) may then be employed to create the properly-sized bore.

Figure 21:
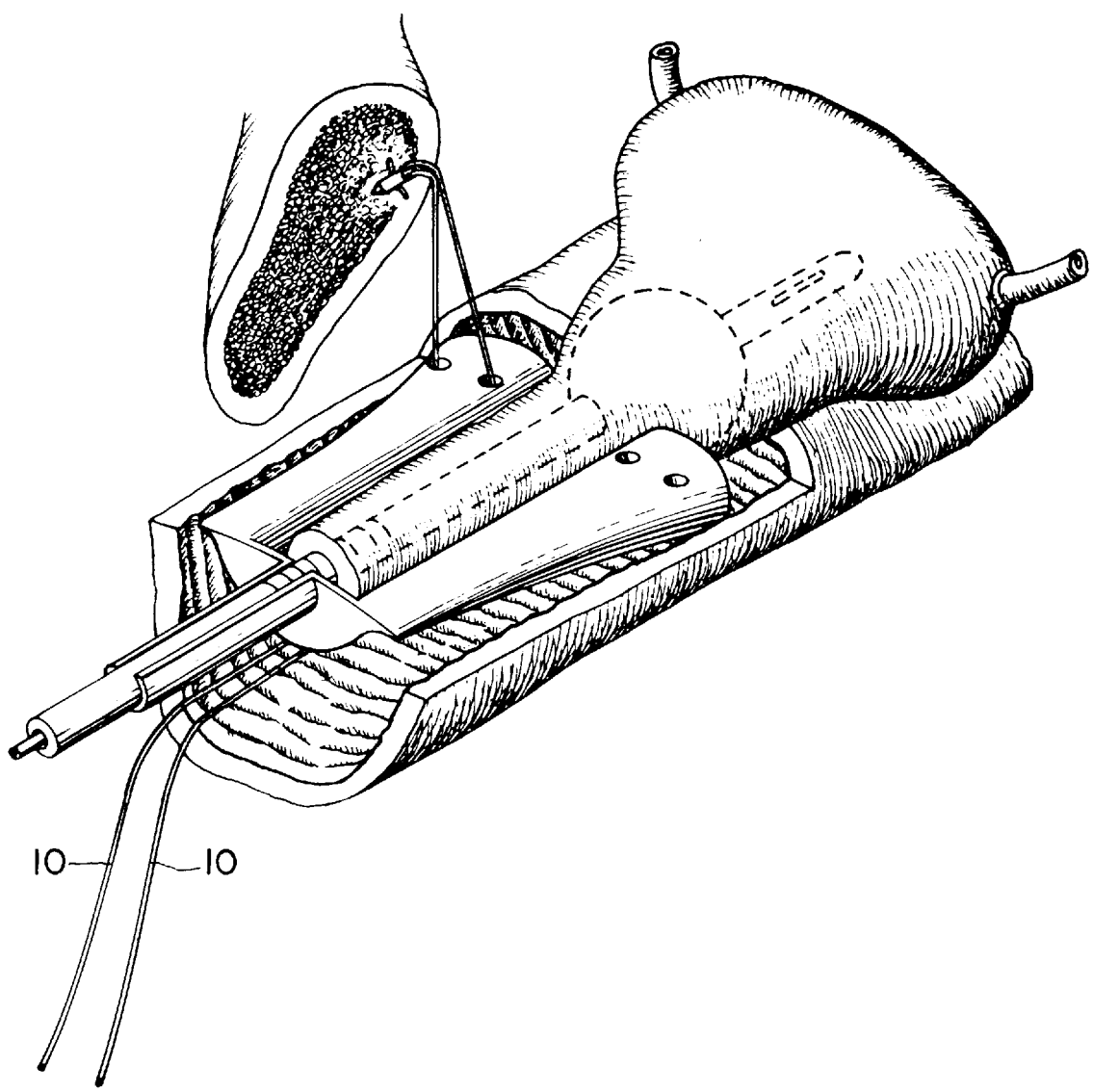
FIG. 21 is a perspective view of the surgical procedure of the present invention wherein portions of the patient's anatomy cut-away for clarity, and wherein the sutures have been retrieved from the pre-peritoneal region for tying.
Figure 22:
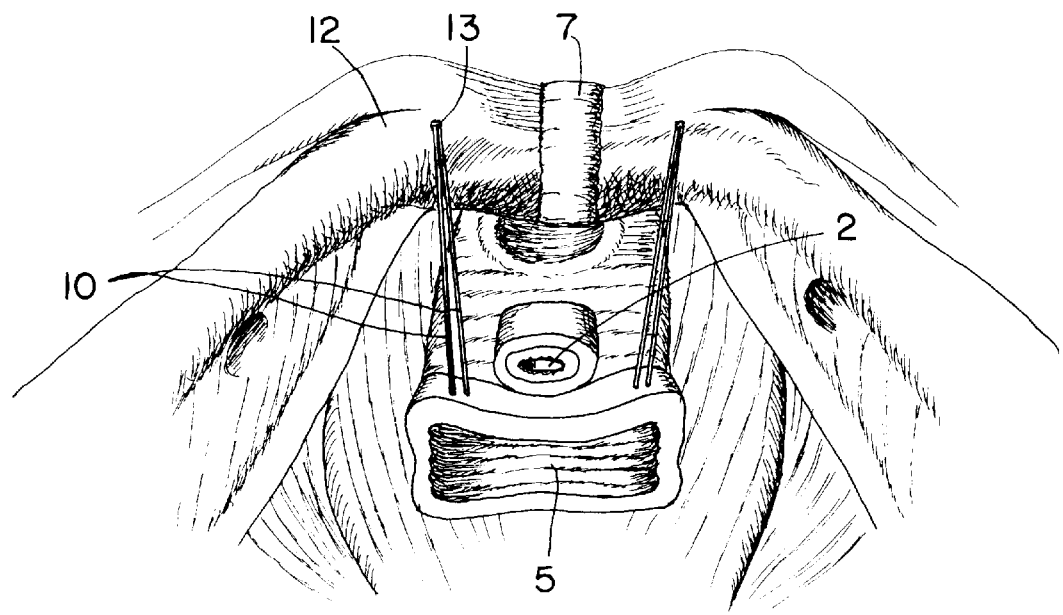
FIG. 22 is a perspective view of the space of Retzius, and illustrates the proper placement of the anchors and sutures employed in the present invention.

In order to create the starter "crater" in the pubic bone, a $CO_2$ laser (such as a SHARPLAN 20 watt) is inserted through the laparoscopic channel, and is employed to create a cone-shaped crater slightly larger than the diameter of the laser beam in the pubic bone on either side of the pubic symphysis. The diameter of the laser beam is preferably about 2 mm, and therefore the cone-shaped crater created in the pubic bone is slightly larger than 2 mm in diameter. The crater should be sufficiently deep to reach the cancellous bone. A crater is established on either side of the pubic symphysis directly above and approximately 1cm lateral to the periurethral fascia at the UVJ. FIG. 21 depicts the space of Retzius after creation of bores 9 and 17 in pubic bone 12 on either side of pubic symphysis 7. The desired placement location can be readily determined through means of the optics of the laparoscope, as proper dissection of space of Retzius 8 will provide sufficient vision for proper identification of the appropriate structures in the patient. If needed, the surgeon may use one or more fingers to press upwardly on the periurethral tissue on either side of the urethra within the vagina in order to properly position the two starter craters in the pubic bone.

Once access to the cancellous bone has been provided by the cone-shaped craters created on either side of the pubic symphysis using the laser, the bore for insertion of the anchor may be readily created using the drill tamper tool of the present invention. Since the cancellous bone is significantly softer than the periosteum or cortical bone, it is not necessary that a sharp awl or drill bit be used to create the bore. Rather, a bluntly pointed drill tamper tool may be used, wherein the end of the tamper tool is not sufficiently sharp to puncture the bladder or other soft tissue under normal use. This provides a significant advantage in that damage to the bladder or other soft tissue structures in the patient may be readily avoided, and drill guides and the like which must be used with the MITEK instruments and similar apparatus can be avoided. As will be understood, the MITEK drill guides cannot possibly be employed laparoscopically. The laser employed to create the cone-shaped craters can be readily aligned in the proper location, without risk of slippage or other inadvertent movement during the procedure. The laser-created craters can then be readily employed to insure that the bores for anchor placement are created in the exact, desired location.

One embodiment of the drill tamper tool of the present invention is shown in FIGS. 5–7, and comprises an elongate rigid member 20 having a distal end which comprises a conical boring tip 21. End 22 of conical boring tip 21 preferably has a cross section similar in size and shape to the crater created in the pubic bone by the laser. In this fashion, alignment of conical boring tip 21 within the crater will be relatively easy. It is also preferred that end 22 of conical boring tip 21 be blunt so that it will not penetrate soft tissue such as the bladder during normal use (i.e., not sufficiently sharp to penetrate soft tissue or organs during normal use). Certainly, however, conical boring tip 21 should be sufficiently thin and blade-like to permit boring tip 21 to create the bore in the soft cancellous bone by use of hand force through the laparoscope. In this regard, conical boring tip 21 is preferably shaped similar to a flat bladed screwdriver. Thus, boring tip 21 has tapered side surfaces 23 and 24 which terminate in portion 25 which is of a circular cross-section. The diameter of circular/cross-section portion 25 is identical to the diameter of the bore which will be created in the pubic bone. By rotating the drill tamper tool while simultaneously pressing boring tip 21 into the crater in the pubic bone, the desired bore will be readily created therein. The diameter of portion 25 is also approximately the same as the body of the anchor to be inserted into the bore.

In order to ensure sufficient support for the bone anchors of the present invention, it is also important that the anchor be seated deep within the pubic bone. In order to ensure proper depth of the bore, therefore, collar 26 is provided on the drill tamper tool. Collar 26 is of a larger diameter than conical boring tip 21, and therefore will act as a stop preventing further penetration of the drill tamper tool into the bone. Although collar 26 is shown as tapering in diameter between conical boring tip 21 and intermediate portion 27, it is also possible that collar 26 simply comprise a non-tapered end of intermediate portion 27. Intermediate portion 27 has a diameter significantly greater than that of conical boring tip 21, and is positioned on the opposite end of collar 26. Intermediate portion 27 not only allows the provision of collar 26, but also adds rigidity to the tamper tool. Intermediate portion 27, however, should be significantly smaller in diameter than the operative channel of the laparoscope so that sufficient vision of the operative region is provided. Preferably, the length of conical boring tip 21 is between about 1, and 3 cm, and most preferably about 1.4 cm. Intermediate portion 27 is preferably between about 2, and 6 cm, and most preferably about 5 cm.

In order to provide stability during the boring procedure, cylindrical guide portion 28 is also included on the drill tamper tool. Guide portion 28 has first end 29 and second end 30. First end 29 is attached to intermediate portion 27 at the opposite end of collar 26. Cylindrical guide portion 28 preferably has a diameter slightly less than the operative channel of the laparoscope. In this fashion, guide portion 28 provides the necessary stability within the laparoscope to ensure proper placement of the bores. Second end 30 of guide portion 28 is preferably attached to handle 31. While handle 31 is shown as having a flat end portion 32 and curved hand grip surfaces 33, handle 31 can be of a variety of forms and still be sufficient for purposes of the present invention. Handle 31 facilitates the proper manipulation of conical boring tip 21 through the laparoscope, and provides a sufficiently firm surface 32 upon which force may be applied to complete the boring operation. Guide portion 28 preferably has a length between about 50 and about 55 cm, and most preferably about 52 cm. The overall length of the drill tamper tool therefore permits sufficient access to the pubic bone, while also providing an ergonomically-effective boring operation through the laparoscope and ensuring that the tool does not interfere with the anesthesiologist.

FIGS. 44–45 depict an alternative embodiment for the drill tamper tool of the present invention wherein the intermediate portion has been eliminated. Thus, the drill tamper tool of FIG. 44 comprises an elongate, rigid shaft 328, which corresponds to the guide portion in the embodiment of FIGS. 5–7. At one end of shaft 328 is handle 331 which serves the same purpose as described previously. At the opposite end of shaft 328 is boring tip 321. Boring tip 321 is as described previously, and thus has blunt end 322, circular cross-section portion 325, and tapered side surface 323 (the opposite tapered side surface is not visible). Collar 326 is positioned between boring tip 321 and shaft 328, and once again acts as a stop to limit penetration to the desired depth. Collar 326 is preferably tapered as shown in order to provide sufficient laparoscopic vision. Boring tip 321 has a length of between about 1 and about 3 cm, preferably about 1.4 cm. Shaft 328 has a length of between about 45 and about 60 cm, preferably between about 50 and about 52 cm, thereby providing laparoscopic access to the pubic bone. Shaft 328 also preferably has a diameter which is only slightly less than the operative channel of the laparoscope in order to provide stability and prevent insufflation gas from escaping. While end 322 of tip 321 may be blunt as previously described, in the embodiment of FIGS. 44–45 it has a pointed tip.

C. Insertion of Bone Anchors in Pubic Bone

One preferred anchor for use in the present invention is shown in FIGS. 3 and 4, and is identical to that disclosed in U.S. Pat. No. 5,207,679. Anchor 9, which is preferably made of titanium alloy or other suitable material, has a cylindrical body 40 and a conical end 44 attached thereto. At least two flexible barbs 41 curve outwardly away from body 40. A groove 42 is provided on either side of body 40 at the end opposite to conical end 44. In addition, cylindrical end 45 extends away from body 40 adjacent groove 42. The longitudinal axis of cylindrical end 45 is aligned with the longitudinal axis of body 40. The diameter of cylindrical end 45 is preferably equivalent to the diameter of body 40 within grooves 42 positioned on opposite sides of body 40. As will be understood below, this structure facilitates the attachment of anchor 9 to an insertion tool.

As best shown in FIG. 4, body 40 and cylindrical end 45 have an aperture 43 provided therethrough. Aperture 43 is sized so as to accommodate a suture appropriate for the fixation procedure of the present invention. It is preferred that a size 0 GORE-TEX suture be employed, and thus anchor 9 and its accompanying aperture 43 should be sized accordingly. The use of a GORE-TEX suture is preferred for reasons of strength and non-elasticity. Certainly other types of sutures could be employed if necessary. A portion of suture 10 is shown in FIG. 3 having been inserted through aperture 43.

The insertion of anchor 9 is relatively straightforward, and merely requires that the anchor be pressed completely into the bore which has previously been created in the pubic bone. Preferably, anchor 9 is inserted into the bore in the pubic bone until conical end 44 reaches the distal end of the bore. The bore should be at least as long as the length of anchor 9, however, it is preferably considerably longer to ensure sufficient support for the anchor. As anchor 9 is pressed into the bore, flexible barbs 41 will be compressed against body 40 as they are inserted past the hard periosteum and cortical bone surrounding the bore. Once within the bore, however, flexible barbs 41 will tend to spring back into the soft cancellous bone, thereby securing the anchor in place. A slight tug on the tails of the suture 10 will also cause barbs 41 to further deploy.

In order to insert anchor 9 into the bore previously created in the pubic bone, the anchor insertion tool shown in FIGS. 8–10 may be employed. Thus, after the drill tamper tool has been employed to create the necessary bores, the anchor insertion tool of the present invention having an anchor and threaded suture loaded there, is inserted into the laparoscope for proper seating of anchor 9.

The anchor insertion tool of the present invention comprises a rigid elongate member 50 having a handle 51 at one end, and an anchor-receiving tip 52 at the opposite end of elongate member 50. As was the case with the drill tamper tool, handle 51 can be of any variety, and that shown is only one embodiment for this handle. Anchor-receiving tip 52 is similar in construction to that shown in FIGS. 4–6 of U.S. Pat. No. 5,207,679. Anchor-receiving tip 52 is constructed so as to matingly receive anchor 9 in order to facilitate insertion of anchor 9 into the bore. As will be apparent, the longitudinal axis of anchor-receiving tip 52 should be aligned with the longitudinal axis of elongate member 50. Anchor-receiving tip 52 is cylindrical in nature, having a diameter approximately equivalent to body 40 of anchor 9. In this manner, at least a portion of anchor-receiving tip 52 may pass through the bore in the pubic bone during the anchor insertion process to properly seat the anchor completely within the bore.

Anchor-receiving tip 52 has a pair of guide tabs 53 extending from the end of anchor-receiving tip 52 on either side thereof. Guide tabs 53 are sized and shaped so as to be matingly received within grooves 42 positioned on either side of anchor 9. Anchor-receiving tip 52 also has a cylindrical slot 54 aligned with the longitudinal axis of tip 52. Cylindrical slot 54 should correspond in size and shape to cylindrical end 45 of anchor 9 in order to matingly receive the same. It is also preferable that the distance between guide tabs 53 be slightly smaller than the distance between the corresponding grooves 42 on anchor 9. In this fashion, guide tabs 53 as well as cylindrical slot 54 will apply compressive force against anchor 9 thereby more securely holding anchor 9 in place when loaded within anchor-receiving tip 52.

Since suture 10 will extend outwardly on either side of anchor 9, it is preferable to provide a means for ensuring that suture 10 is not abraded by the bone surrounding the bore during the insertion process. Thus, a pair of tapered grooves 55 are provided on either side of the anchor insertion tool, and extend from the end of anchor-receiving tip 52 along at least a portion of the length of elongate member 50. As best shown in FIG. 10 wherein anchor 9 has been loaded upon the insertion tool, grooves 55 ensure that the sutures will be protected by anchor-receiving tip 52 and a portion of elongate member 50 during the insertion process. Since any nicks in the suture may compromise the strength and permanency of the fixation, it is important to ensure that the suture is not damaged in any fashion.

Anchor-receiving tip 52 should also be of the proper length to ensure deep placement of anchor 9 completely within the bore. Thus, the length of the combination of anchor-receiving tip 52 and bone anchor 9 when loaded in the manner shown in FIG. 10 should be equivalent to the size of the bore created in the pubic bone. Since the diameter of elongate member 50 is significantly greater than that of anchor-receiving tip 52, distal end 56 of elongate member 50 will firmly abut the pubic bone once the anchor has been completely inserted into the bore. In this manner, the surgeon can be certain that the anchor has been seated to its complete and proper depth.

As was the case with the drill tamper tool of the present invention, elongate member 50 further comprises an intermediate section 57 and a guide portion 58. Intermediate portion 57 should have a diameter sufficiently less than that of the laparoscope in order to provide adequate vision for the surgeon, and intermediate portion 57 also has distal end 56 described above. Preferably, intermediate portion 57 has a length between about 2 and about 6 cm, most preferably about 5 cm. It should be kept in mind that, as shown in FIG. 10, suture 10 will extend along the length of intermediate portion 57 on either side thereof. This consideration must be kept in mind when sizing the diameter of intermediate portion 57 to ensure not only that it can be easily inserted through the laparoscope, but also to ensure adequate vision.

Guide portion 58 will necessarily be slightly smaller than the diameter of the guide portion for the drill tamper tool previously described, since, as shown in FIG. 10, suture 10 will extend along either side of guide portion 58. With this in mind, the total of the diameter of guide portion 58 and twice the diameter of suture 10 should be only slightly less than the inside diameter of the operative channel of the laparoscope. In this fashion, guide portion 28 provides a rigid support for the surgeon during the anchor insertion process. Preferably, guide portion 58 has a length between about 50 and 55 cm., most preferably about 52 cm. This provides an overall inserter length comparable to that of the drill tamper tool, thereby providing the same advantages with regard to the tamper tool length.

In order to effectively employ the procedure of the present invention laparoscopically, it is necessary that the two tails of suture 10 be controlled as much as possible. If the sutures are permitted to hang away from anchor 9 or the anchor insertion tool, the tails will generally become balled within the space of Retzius, thereby making the suture tying procedure difficult, if not impossible. Although the sutures may be held against the anchor insertion tool by hand, Applicant has developed a more effective manner of accomplishing this. Thus, first and second shouldered depressions 59 and 60 are preferably provided about the circumference of guide portion 58. A small rubber band 61 (as shown in FIG. 10), or other suitable elastic band, may be held within each of the two shouldered depressions, with the two tails of suture 10 held beneath rubber band 61 on either side of guide portion 58 as shown. First shouldered depression 59 is preferably positioned approximately 10 cm from the ends of guide tabs 53. Second shouldered depression 60 is preferably positioned about 40 cm from guide tabs 53. Both shouldered depressions act, in conjunction with an elastic band contained therein, to hold suture 10 in place on the sides of the anchor insertion tool.

Figure 20:
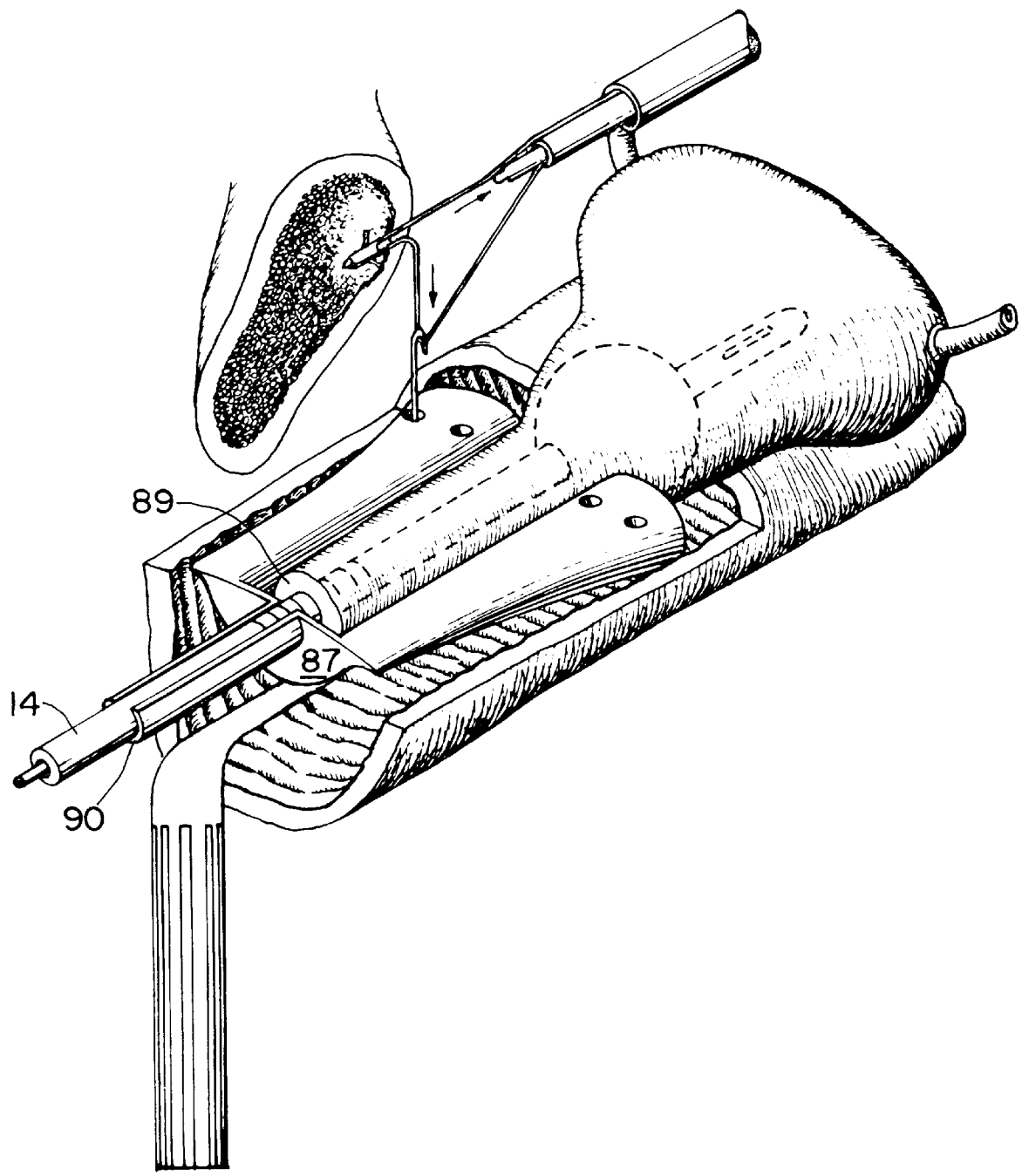
FIG. 20 is a perspective view of the surgical procedure of the present invention wherein portions of the patient's anatomy cut-away for clarity, and wherein the suture retriever of FIG. 11 is being employed.

In addition to holding the suture in place on the anchor insertion tool, the shouldered depression/elastic band combination further improves the laparoscopic procedure of the invention by not only assisting in seating the anchor, but also in the suture retrieval process. As shown in FIG. 20, the anchor insertion tool of the present invention, with a preloaded anchor and suture assembly attached thereto, is inserted through the laparoscope for placement of the anchor as previously described. Once the anchor has been seated within the bore, the anchor insertion tool is then pulled outwardly utilizing handle 51 contained thereon. The combination of shouldered depressions 59 and 60 and rubber band 61 act to provide tension in suture 10 which in turn pulls outwardly on anchor 9 which is now contained in the bore. This outward force on anchor 9 will cause flexible barbs 41 to extend outwardly into the cancellous bone surrounding the bore, thereby further securing anchor 9 in position. In other words, this outward force on suture 10 by the drag created by the shoulder depression/elastic band combination will act to deploy the previously compressed barbs 41 on anchor 9, thereby rigidly securing anchor 9 within the bore.

In order to facilitate the surgical procedure of the present invention, the drill tamper tool and the anchor-insertion tool described above may be provided in the form of a reusable surgical kit.

D. Fixation of Periurethral Tissue at the UVJ Via Suturing

Once the anchor and suture assembly have been secured within the bore created in the pubic bone, it is next necessary to utilize the two tails of the suture to elevate the periurethral tissue on the corresponding side of the urethra at the UVJ. Applicant has found that the most effective means for accomplishing this is to pull each tail of the suture through the periurethral tissue into the vagina. In this fashion, the two tails may then be easily tied to one another within the vagina to provide the necessary support, and eliminating any need for laparoscopic suture tying. Obviously, however, a means for retrieving the suture tails must be provided.

The method of suture retrieval is best shown in FIG. 20, which is a perspective view of the procedure with portions of the patient's anatomy cutaway for purposes of clarity. As shown in FIG. 20, as the anchor insertion tool of the present invention is partially withdrawn from the patient through the laparoscope, first shouldered depression 59 in combination with rubber band 61 will cause both suture tails to be tensioned between the anchor and the anchor insertion tool as shown. Were this not the case, the suture tails would merely fall into the space of Retzius similar to a ball of yarn, and thereby be difficult (if not impossible) to retrieve. While the suture tails could be tensioned between the anchor and the anchor insertion tool by pulling outwardly on the sutures, this would unnecessarily require an additional pair of hands. Thus, the shouldered depression/rubber band combination is also effective in this regard.

Once the anchor insertion tool has been partially removed in order to tension the suture tails in the manner shown in FIG. 20, a suture retrieving tool may be inserted into the vagina and then pressed upwardly on one side of the urethra into the space of Retzius in order to retrieve one of the suture tails in the manner shown. Thus, the suture retrieving tool must have a sharp point capable of passing completely through the full thickness of the periurethral fascia and vaginal mucosa adjacent the urethra. The suture retrieval tool must also have a means for grasping the suture tail and pulling the tail back through the full thickness of the periurethral and vaginal mucosa by means of the same entry hole created by the sharp point. Each tail is pulled into the vagina in this fashion at the proper location. Preferably, one tail is pulled into the vagina approximately 1 cm from the urethra at the UVJ, and the other tail is pulled into the vagina approximately 2 cm lateral from the urethra. In other words, each tail penetrates the periurethral tissue along an imaginary line extending substantially perpendicularly away from the urethra. Each tail may then be pulled out of the vagina for purposes of tying.

The suture tails are tied to one another using a series of standard surgeon's knots, and each knot is slid by hand to the point in the vagina at which the suture tails were previously retrieved. The tails are tied to one another in a sufficiently tight fashion so that suture 10 creates an upward force on the periurethral tissue adjacent the urethra in order to elevate the urethra at the UVJ and restore the urethra to its proper angle. The position of the urethra can be readily observed by the surgeon as this procedure is performed, thereby ensuring that the urethra is restored to the desired angle. The entire procedure (anchor insertion, suture retrieval, etc.) is then repeated for the anchor placed on the opposite side of the pubic symphysis, and the suture tails of that anchor are pulled into the vagina through the periurethral tissue as the opposite side of the urethra as the first suture tails. Tying is then performed in the same fashion, thereby elevating the other side of the urethra to thereby completely restore the urethral angle at the UVJ.

The result of this process is best shown in FIG. 2, wherein it is shown that suture 10, and the corresponding suture on the opposite side of the urethra have restored the urethra to its proper angle. It should be noted that at no time do the sutures pull upward directly beneath the urethra, since doing so would create the risk that the suture would cause urethral blockage. After tying, the remaining tails of suture 10 are cut at the knot. Cutting may be accomplished using the suture cutter disclosed in copending application Ser. No. 08/719, 487 (filed Sep. 25, 1996) in order to ensure proper and even cutting of the tails. After the suture tails have been cut adjacent to the knot, it is preferred that the knot be moved into the abdominal cavity. This can be accomplished merely by pulling lightly on one portion of the suture within the vagina, which thereby causes the suture to be pulled through one of the holes previously traded in the vaginal mucosa and periurethral fascia towards anchor 9. In other words, the suture acts much like a rope on a pulley system, such that when one portion of the tied suture is pulled downwardly into the vagina, the opposite side will traverse upwardly, carrying the knot with it into the abdominal cavity. In this manner, the knot will not be present within the vagina where it might cause irritation. The portion of suture 10 remaining in the vagina will epithelize within three to four days, and the patient will no longer sense that the sutures are in place. The result is a permanent fixation of the periurethral tissue on both sides of the urethra, thereby restoring the urethra to its correct angle and eliminating the SUI. After completion of the tying process, the surgical area within the patient is flushed with a dilute lidocaine solution, the laparoscope and trocars removed, a stronger lidocaine solution is applied to the incision sites, and the incisions are closed in the usual fashion. The Foley catheter may then be removed, and the patient permitted to recover in the usual fashion. Normal everyday activities may be resumed within 2–3 days.

E. Suture Retriever

In order to pull the tails of suture 10 through the entire thickness of the periurethral fascia and vaginal mucosa, various tools can be employed. For example, a U.S. Surgical Auto-Stitch tool may be effectively employed for this purpose. It is critical, however, that the tool employed being capable of readily be inserted through the periurethral tissue from the vagina into the space of Retzius, while also being capable of grasping the suture tails. It is also critical that the surfaces contacting suture 10 be perfectly smooth in order to eliminate the risk of nicks or cuts in suture 10 which would obviously compromise the effectiveness of the procedure. Applicant has developed a novel suture retriever for accomplishing this purpose which provides a convenient and simple means of retrieving the suture tails.

The suture retrieval tool of the present invention is depicted in FIG. 11, and comprises metal retrieving end 65, midshaft 66, and handle 67. Midshaft 66 and handle 67 may be singularly molded from polycarbonate or a similar FDA-approved material in the typical fashion. As shown in FIG. 12, handle 67 is also preferably knurled in order to facilitate grasping and manipulation of the retriever. Metal retrieving end 65 is preferably made of stainless steel and can be securely molded into distal end 68 of midshaft 66.

Metal retrieving end 65 comprises a rigid, rod-like shaft 69, and a sharp tip 70 capable of penetrating the periurethral tissue. The diameter of distal end 68 is preferably significantly greater than that of shaft 69, and will act as a stop in order to limit the penetration of the suture retrieval tool into the space of Retzius. Thus, the length of shaft 69 and tip 70 may be selected so as to ensure that when the suture retrieval tool is inserted into the space of Retzius through the vagina that sharp tip 70 will generally be incapable of striking any surrounding soft tissue.

Retrieving end 65 further comprises a return leg 71 which extends away from sharp tip 70 in the same direction of shaft 69. Shaft 69, return leg 71 and the underside of sharp tip 70 thus create an inverted U-shaped region capable of ensnaring suture 10 for retrieval purposes. The distance between return leg 71 and shaft 69 in the region of the inverted U-shape is preferably approximately the same diameter as suture 10. In this fashion, and as shown in FIG. 20, after sharp tip 70 has penetrated the periurethral tissue adjacent the vagina in order to enter the space of Retzius, the inverted U-shape may be pulled downwardly over a suture tail, thereby snaring the suture. Metal retrieving end 65 may then be pulled back through the periurethral tissue, and the tail of suture 10 will remain snared between return leg 71 and shaft 69 directly beneath sharp tip 70. Although the suture tail will slide within the U-shaped region, it will nevertheless be pulled into the vagina.

One critical feature of the suture retriever of FIG. 12 is that the inner surfaces of metal retrieving end 65 which contact suture 10 must be rounded and smooth in order to permit suture 10 to freely slide within the inverted U-shaped portion as the retriever is withdrawn. This prevents nicking or fraying of the suture while still permitting the suture tail to be withdrawn. Thus, the only sharp portion of metal retrieving end 65 is sharp tip 70.

While it is possible that handle 67, midshaft 66, and metal retrieving end 65 may all be positioned along the same longitudinal axis thereby forming a rigid, elongate structure, Applicant has found that the process of the present invention can be simplified if the elements of the retriever have the angular relationship indicated in FIG. 11. This is particularly true when the template of the present invention (to be described further herein) is employed. Thus, metal retrieving end 65 preferably is positioned at an angle of between about 100 degrees and about 130 degrees, most preferably about 120 degrees, to midshaft 66 (this angle is indicated as A in FIG. 11). Likewise, handle 67 is preferably positioned at an angle of between about 100 degrees and about 130 degrees, most preferably about 120 degrees, to midshaft 66 (this angle is indicated as B in FIG. 11). Thus, the longitudinal axis of shaft 69 of metal retrieving end 65 will be parallel to the longitudinal axis of handle 67. In this fashion, when the retriever of the present invention is employed midshaft 66 will generally be positioned parallel to the longitudinal axis of the vagina. Metal retrieving end 65 will then extend upwardly through the periurethral tissue into the space of Retzius as desired. As best shown in FIG. 20, handle 67 will thereby extend downwardly outside of the vagina, and thus sharp tip 70 may be readily forced through the periurethral tissue as desired merely by pushing upwardly on handle 67.

As shown in FIG. 11, the transitions between handle 67 and midshaft 66 as well as between midshaft 66, and retrieving end 65 should be gently curved in order to ease placement. It should be noted that angles A and B can vary significantly, however it is preferred that they be as close to one another as possible so that the parallel relationship of handle 67 and retrieving end 65 is maintained. In addition, the present configuration ensures that the retrieving end 65 will enter the space of Retzius at an angle of approximately 90 degrees to the tensioned suture tails (i.e., the suture tails tensioned between the anchor and the anchor insertion tool). This parallel relationship allows for effective snaring of the suture, as well as improved vision of the retrieval through the laparoscope.

Preferably, midshaft 66 is between about 2 and about 6 cm. in length, most preferably about 4 cm. The cross-sectional area of midshaft 66 should merely be a size chosen to provide the necessary rigidity while also not blocking vision within the vagina during the procedure. Likewise, handle 67 is preferably about 4 cm long, however the length is not as critical since handle 67 remains completely outside of the body. The diameter of handle 67 should be chosen so as to provide a comfortable and secure means of grasping the suture retrieval tool. Preferably, handle 67 is about 3 cm in diameter.

An alternative, and presently preferred embodiment for the suture retrieval tool of the present invention is shown in FIGS. 46–48. In this embodiment, the suture retrieval tool once again comprises metal retrieving end 265, a midshaft 266 and a handle 267. The longitudinal axis of these three elements are as shown by the dashed lines. Midshaft 266 and handle 267 may be singularly molded from polycarbonate or a similar FDA-approved material in the typical fashion. Handle 267 preferably is curved in the manner shown so as to provide a comfortable grip for the surgeon.

Metal retrieving end 265 comprises a rigid, rod-like shaft 269 and a tip of portion 270. As best shown in FIG. 47, tip portion 270 is preferably flat in nature, and, as shown in FIG. 48, has a width L which is less than the width or diameter of shaft 269. Tip 270 has a sharpened distal end 274, and a suture slot 271 located approximately of the distal end. Slot 271 also has an entrance 275 thereto, and entrance 275 is spaced inwardly from shaft 269. In other words, the center line of tip portion 270 is slightly off-set from the longitudinal axis of shaft 269. In this manner, a suture may be snared in the manner described previously by allowing the suture to enter entrance 275 until it rests within slot 271. When the tip of the suture retrieval tool is then retracted back into the vagina, the off-set between opening 275 and shaft 269 will ensure that leg 276 adjacent suture slot 275 will not snag against the patient's tissue. In other words, since shaft 269 tends to create a puncture hole in the patient's tissue which is greater than the width of tip 270, the tip will not snag on the edges of this puncture hole.

In addition, shaft 269 preferably has a diameter which is significantly greater than that of the suture employed. In this manner, shaft 269 will create a puncture hole is the soft tissue which is larger than the knot in the suture. In this manner, the knot may be moved from the vagina into the abdominal cavity of the patient through this puncture hole in the manner previously described. In order to facilitate insertion of shaft 269 into the patient, tapered walls 277 are provided. Tapered walls 277 provide a smooth transition between flat tip 270 and rounded shaft 269.

In the embodiment of FIGS. 46–48, the angular arrangement of retrieving end 265, midshaft 266 and handle 267 is preferably modified somewhat from that previously described in that the angle between midshaft 266 and retrieving end 265 is greater than that previously described. Applicants have found that by opening this angle further, the surgeon will be better able to avoid striking blood vessels on the undercarriage of the pubic bone with the sharp distal end 274. Thus, while angle M between midshaft 266 and handle 267 is preferably between about 120 degrees and about 135 degrees, the angle between retrieving end 265 and midshaft 266, however, is between about 135 degrees and about 155 degrees, more preferably about 150 degrees. In order to add strength and rigidity, a small extension to 278 on midshaft 266 has a longitudinal axis corresponding to that of retrieving end 265. Extension 278 may be hollow, thereby allowing retrieving end 265 to be inserted and secured therein. The diameter of extension 278, as well as the remainder of midshaft 266, is preferably larger than that of shaft 269. This allows end 268 of extension 278 to act as a stop which prevents the midshaft from penetrating the soft tissue once the retrieving end is inserted through the soft tissue of a patient.

F. Surgical Template

While the placement of the sutures through the periurethral tissue at the UVJ may be accomplished by merely feeling for the correct location within the vagina by hand, particularly in relation to the ball of the Foley catheter, Applicant has developed a novel template which greatly simplifies proper placement of the sutures. The term "template" is intended to include any device which may be employed to direct placement of a fixation device (such as a suture) through tissue at a predetermined location or in a predetermined relationship to a specific location (e.g., a predetermined distance from the UVJ). One or more guides on the template direct placement of the fixation device. The phrase "directing placement of the fixation device" is intended to include templates wherein the guides on the template direct passage of the fixation device through the tissue, as well as templates wherein the guides direct the creation of an incision or other opening in the tissue through which the fixation device is later inserted. The guides on the template may comprise, for example, apertures, slots, notches, protrusions or visible indicia (such as one or more lines or graduations, or even a light source for transilluminating the tissue through which placement of the fixation device is to be directed).

The template of the present invention not only prevents bladder injury, urethral injury, and vascular accidents during the urethropexy procedure previously described, the template also ensures proper placement of a fixation device. For example, the template of the present invention can ensure a proper distance between the two suture tails to ensure that there is adequate periurethral tissue between the tails to provide the necessary support in a retropubic bladder neck suspension. Obviously if the suture tails are placed too close to one another, there is a risk that the suture will tear through the periurethral tissue and eliminate the fixation. Thus, a template specific for a retropubic bladder neck suspension (particularly one performed laparoscopically) is provided, wherein the guides on the template comprise at least two apertures which may be properly positioned on either side of the urethra. The suture retriever described previously may then be inserted through these apertures and thereafter through the periurethral tissue in order to snare the suture tails in the manner described above.

One embodiment for the surgical template is depicted in FIGS. 13–17. The template comprises a trough 80 of arcuate cross-section, wherein trough 80 is sized so as to cradle the patient's urethra when properly positioned. First and second wing members 81 and 82 extend away from opposite sides of trough 80, preferably perpendicularly to the longitudinally axis of trough 80 in the manner shown. Most preferably wing members 81 and 82 extend perpendicularly away from opposite sides of trough 80 at the upper most edges 83 and 84 of trough 80. First and second suture guide apertures 85 and 86 are positioned in each of the wing members 81 and 82 as shown. The guide apertures are positioned so that when the urethra of the patient is properly positioned within trough 80, guide apertures 85 and 86 on each wing will indicate the proper location for the sutures. First suture guide aperture 85 is positioned so that the first tail of suture 10 will penetrate the periurethral tissue approximately 1 cm from the urethra adjacent the UVJ. Second guide aperture 86 is preferably positioned about 1 cm further away from the urethra along a line perpendicular to the longitudinal axis of trough 80. In other words, the distance between first suture guide aperture 85 and second suture guide aperture 86 is preferably about 1 cm. In this manner, the surgeon can be confident that sufficient periurethral tissue will be present between the two suture tails.

Figure 13:
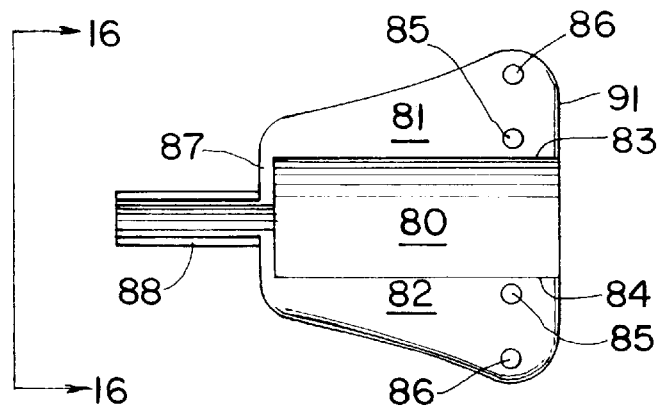
FIG. 13 is a top plan view of a suture template of the present invention.
Figure 14:
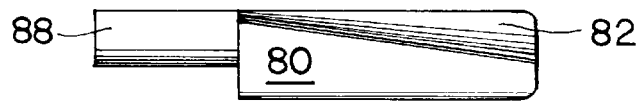
FIG. 14 is a side plan view of the template of FIG. 13.
Figure 15:
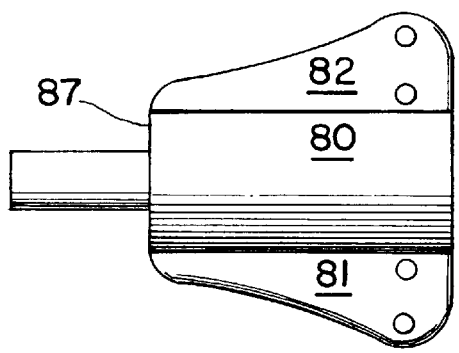
FIG. 15 is a bottom plan view of the template of FIG. 13.
Figure 16:
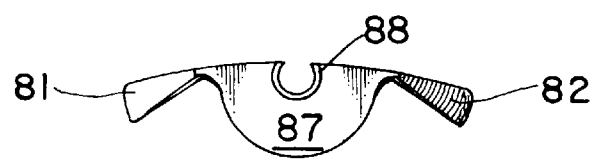
FIG. 16 is an end plan view of the template of FIG. 13, taken along line 16—16 thereof.

It is certainly possible that the template of the present invention may merely be held in place by hand, and in fact the downwardly sloping nature of the underside of wing members 81 and 82 are suitable for placement of the surgeon's fingers thereunder. Additional alignment means are preferably provided, however. At a minimum, end wall 87 is provided at the end of trough 80 furthest away from the suture guide apertures. Thus, as long as the template is properly sized for the length of the patient's urethra, the surgeon may hold the template in place with end wall 87 abutting the outermost end 89 of urethra 4 in order to ensure proper alignment. For example, if the length of the patient's urethra is determined to be three cm, the distance between end wall 87 and first and second guide apertures 85 and 86 should be between about 2.5 and about 3.2 cm, most preferably about 2.8 cm. The guide apertures should also be between about 0.25 and about 0.5 cm from distal end 91 of the wing members (FIG. 13). As long as the template is positioned with end wall 87 abutting the outermost portion of the urethra, the surgeon will be assured that the sutures will be properly placed without risk of puncturing the bladder, or urethra.

While the surgeon may employ two fingers beneath wing members 81 and 82 to hold the template in the proper position, Applicant has found that the provision of arcuate alignment member 88 secured to end wall 87 may be effectively employed for securing the template in place without the need for the surgeon to hold the template in any manner. Alignment member 88 is preferably positioned parallel to trough 80, with the center line of alignment member 88 aligned with the center line of trough 80. Alignment member 88 may either extend away from trough 80 as shown in FIG. 13, or alternatively may extend away from end wall 87 directly along the interior of trough 80 as shown in FIG. 18.

When the embodiment of FIGS. 13–16 is employed, alignment member 88 is preferably sized so that when the template is manufactured from a resilient material, alignment member 88 may be rigidly snapped about Foley catheter 14 as shown in FIG. 20. Thus, the shaft of Foley catheter will be securely held within alignment member 88, and the surgeon need only pull outwardly on the Foley catheter while sliding the template into the vagina towards the urethra until end wall 87 abuts end 89 of urethra 2. The ball of the Foley catheter will thus be positioned at the UVJ, and the template will likewise be positioned at the appropriate location assuming that a template of the proper size has been selected based upon the length of the urethra. Alternatively, the template may be secured to any of a variety of other elongate members which are inserted into the patient's urethra, or the elongate member to be inserted into the urethra may be provided as part of the template itself. Thus, the template may even include a Foley-type catheter as an integral part of the template, wherein the catheter is located in the same relative position as that shown in FIG. 17.

As an alternative to providing various sizes for the template of the present invention, a single, larger-sized template may be employed provided that alignment member 88 is snapped about the shaft of Foley catheter 14 (or other elongate member) in the proper location. Thus, instead of abutting end wall 87 against end 89 of urethra 2, end wall 87 is instead aligned with the appropriate graduation along the shaft of Foley catheter 14 based upon the previously-measured length of the urethra. Likewise, end 90 of alignment member 88 could alternatively be aligned with the appropriate graduation along the shaft of Foley catheter 14 in order to provide the proper placement of the template based upon the length of the patient's urethra.

Figure 18:
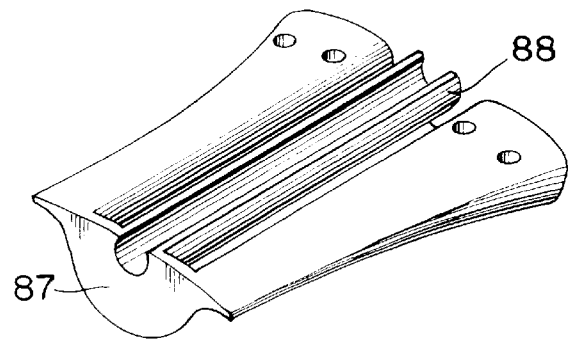
FIG. 18 is a perspective view of an alternative embodiment of the suture template according to the present invention.

FIG. 18 depicts yet another alternative embodiment for the template of the present invention in which alignment member 88 extends along the interior of trough 80. In employing this embodiment, alignment member 88 is inserted into the urethra along with Foley catheter 13 until end wall 87 of the template abuts end 89 of urethra 2. As will be understood, therefor, an appropriately-sized template will ensure proper placement of the sutures.

Figure 42:
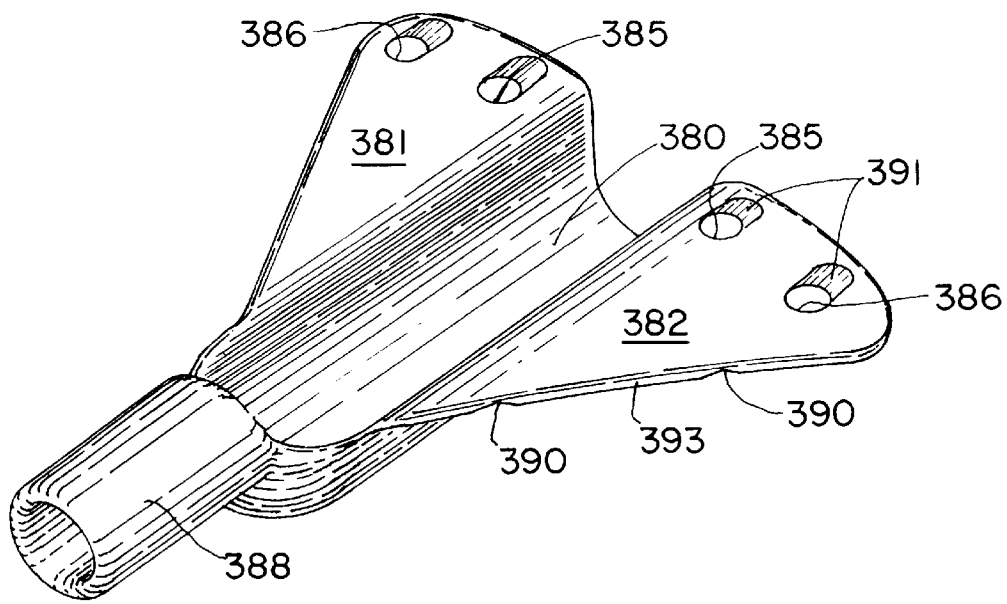
FIG. 42 is a top perspective view of an alternative embodiment for the surgical template of the present invention.
Figure 43:
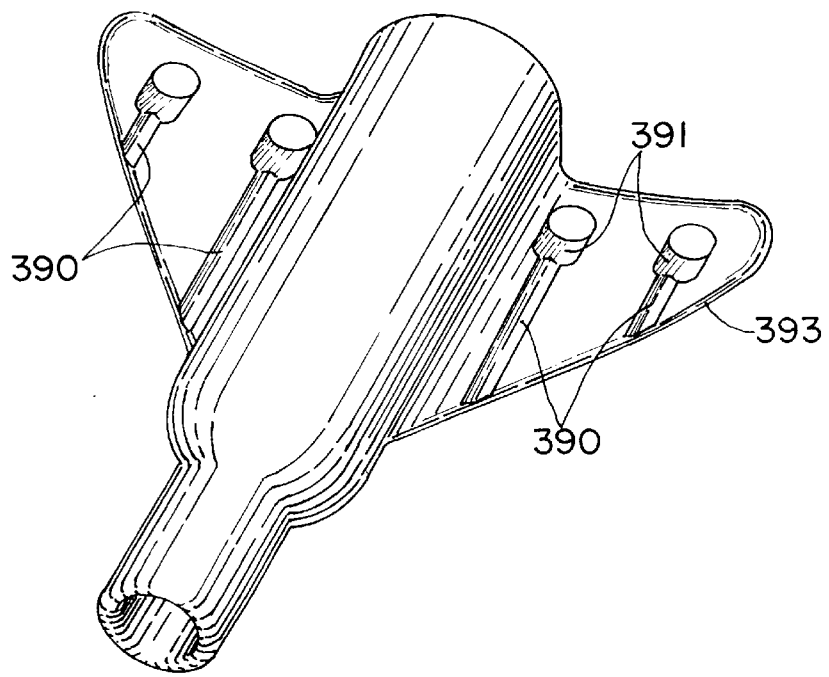
FIG. 43 is a bottom perspective view of an alternative embodiment for the surgical template of the present invention.

FIGS. 42–43 depict another alternative embodiment for the surgical template of the present invention. As was the case in the embodiment of FIGS. 13–16, alignment member 388 extends away from trough 380. In this embodiment, alignment member 388 is tubular in nature. In addition, the longitudinal axis of alignment member 388 is positioned slightly above the longitudinal axis of trough 380. This spacing provides for more proper alignment of the template. Instead of rigidly snapping about a Foley catheter, a Foley catheter may merely be slide into alignment member 388 and held in place by friction or other suitable adhesive means. The template of FIGS. 42–43 may even be provided to the surgeon with a Foley catheter already extending through alignment member 388. Preferably, alignment member 388 is sized so as to snugly hold the Foley catheter therein, and the template is provided to the surgeon with the Foley catheter permanently affixed to the template at the desired location.

Wing members 381 and 382 are once again provided, along with first and second guide apertures 385 and 386 therein. In order facilitate the insertion of the tip of a suture retrieval tool through these apertures, grooves 390 are provided on the underside of each wing. Grooves 390 extend parallel to the longitudinal axis of trough 380, and preferably extend between the apertures and the front edge 393 of each wing. In this fashion, the tip of the suture retrieval tool may be slid along grooves 380 until it reaches the desired aperture. A bevel 391 is also provided on the side of the aperture adjacent grooves 390. Bevel 391 permits the retrieving end of the suture retrieval tool to be moved to a more acute angle with respect to the wing member during the retrieval process. A similar bevel 391 is provided on the upper surface of each wing member adjacent each aperture. Bevels 391 on the upper surface of the wing members extend from the opposite side of each aperture as the bevels on the under surface of the wing members, and may extend partially or completely to the distal end of each wing member. This further ensures that the retrieving end of the suture retrieval tool can be moved to an acute angle with respect to the wing members.

The template of the present invention can be manufactured of any suitable material such as polycarbonate or other FDA-approved plastic. The template may be readily molded using known technology, and is preferably manufactured as a disposable, single-use item. The drill tamper tool and anchor insertion tools, on the other hand, should be made from medical-grade stainless steel. The handles, however, may be polycarbonate or other FDA-approved plastic.

G. Alternative Anchor and Anchor-Insertion Tool for Laparoscopic Urethropexy

Figure 19:
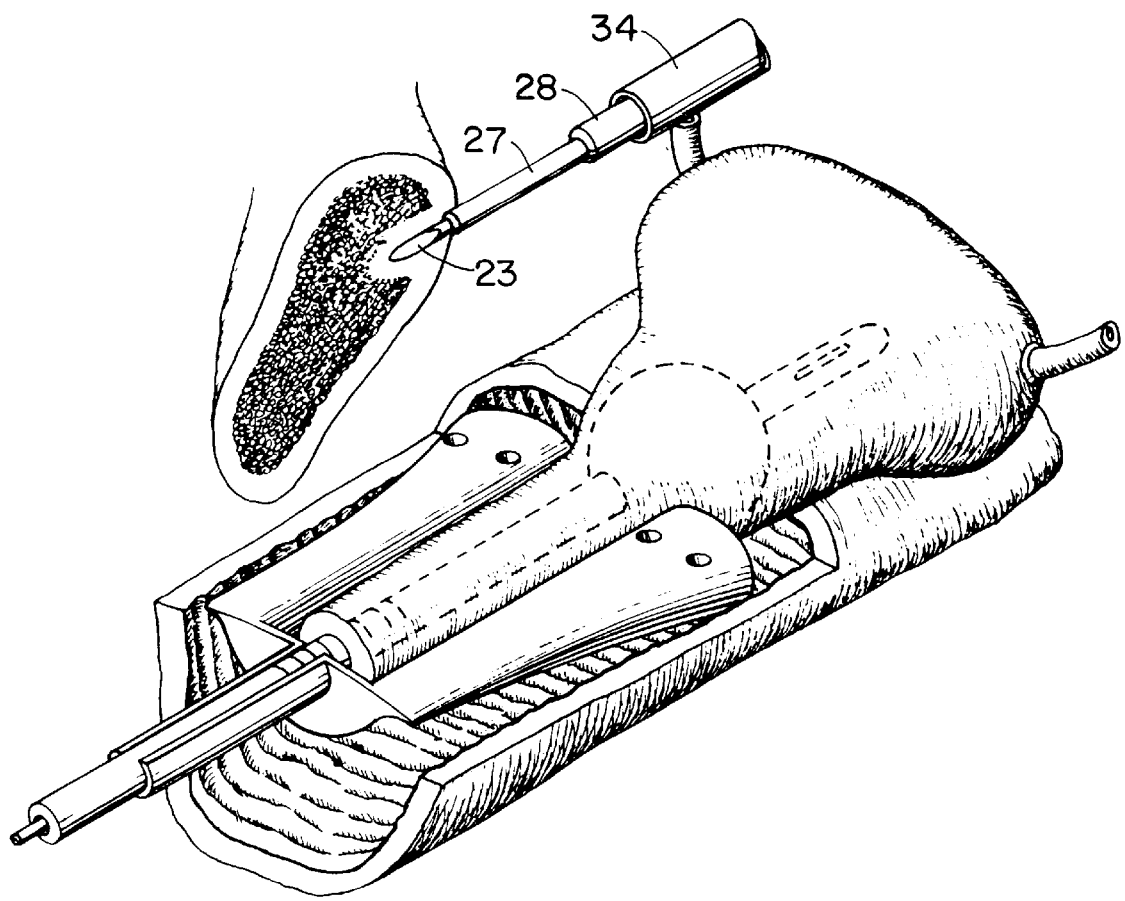
FIG. 19 is a perspective view of the insertion tool of FIG. 8 in use during a surgical procedure with portions of the patient's anatomy cut-away for clarity.
Figure 23:
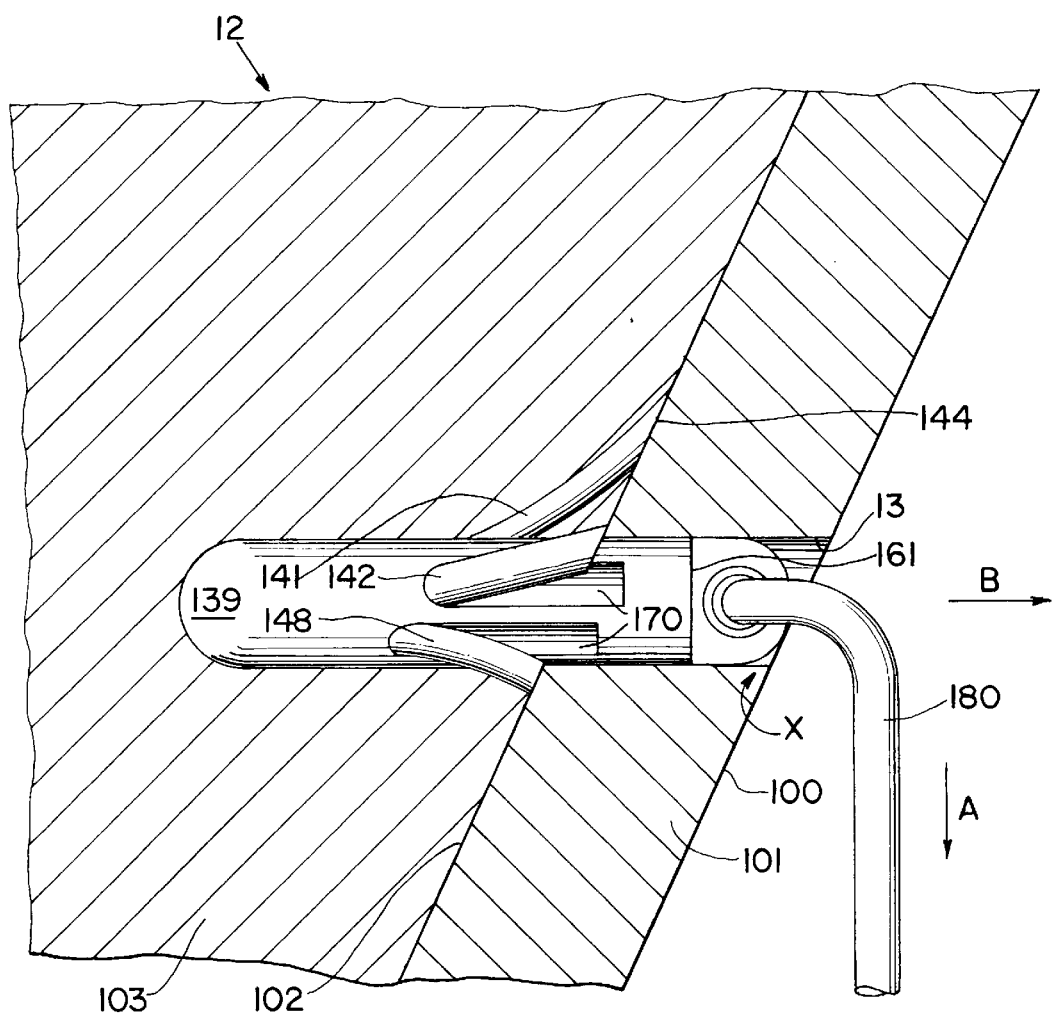
FIG. 23 is a side plan view of the anchor of the present invention in place in the pubic bone of a patient, wherein the pubic bone is shown in cross-section.

As mentioned previously, and as best shown in FIG. 19, pubic bone 12 falls away from the laparoscope at an angle of about 45° to 60°. Thus, it is impossible to create a bore in the pubic bone which extends perpendicularly from the surface of the bone. Thus, the bore produced in pubic bone 12 extends inwardly at an angle of between about 20° and about 60°. In other words, as shown in FIG. 23 which is a cross-sectional view of pubic bone 12, when bore 13 is viewed in cross-section as shown, the angle between surface 100 of the pubic bone and bore 13 at X will be between about 20° and about 60°, preferably about 45°. During the laparoscopic surgical procedure of the present invention, the surgeon may readily modify angle X in order to provide an angle which corresponds to that of the anchor to be described (preferably about 45°). This may be accomplished by inflating or deflating the abdominal cavity as needed in order to change the angle of the laparoscopic channel in relation to the pubic bone. Since interior surface 102 of cortical bone 101 is parallel to outer surface 100 of pubic bone 12, this same angular relationship will exist within the interior of the bore. When an anchor such as that disclosed in FIGS. 3 and 4 is employed, one will immediately recognize that this angular relationship of surface 102 and bore 13 will only permit the lower barb of the anchor to contact surface 102. Since cancellous (or tribecular) bone 103 offers very little support for the anchor, only the contact between the lower most barb of the anchor of FIGS. 3 and 4 and surface 102 provides the principle support which prevents the anchor from being pulled out of the bore.

When anchors of the type shown in FIGS. 3 and 4 are tested for pull-out strength, they are typically pulled only in the direction of arrow B. After the urethropexy procedure of the present invention is accomplished, however, any force on the anchor is most often in the direction of arrow A. As will be readily understood, due to that fact that only the lower barb will be in contact with surface 102, it is possible for the anchor to be pulled out of the bore due to forces acting in the direction of arrow A. This results from the fact that the end of the anchor to which the suture is secured is able to pivot downwardly in the direction of Arrow A since cancellous bone 103 offers little support.

Figure 24:
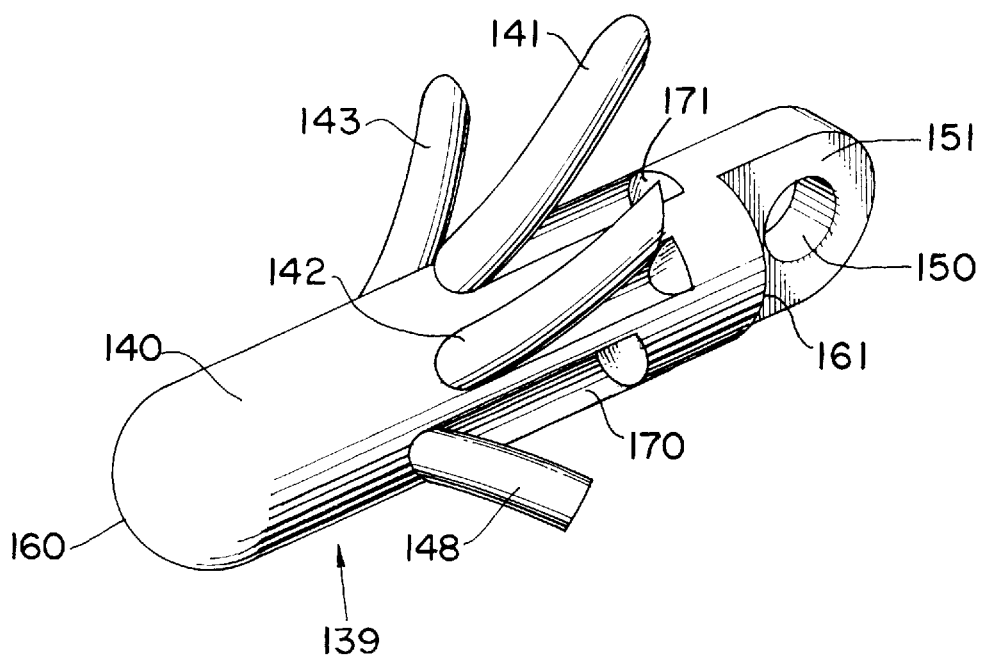
FIG. 24 is a perspective view of the anchor of FIG. 23.
Figure 25:
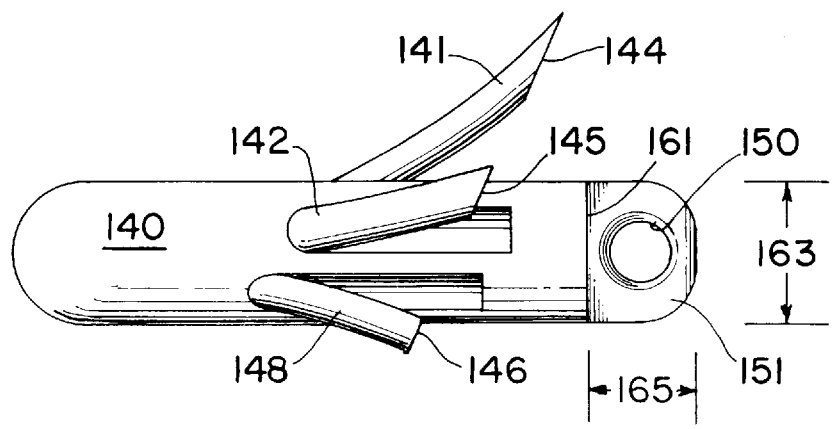
FIG. 25 is a side plan view of the anchor of FIG. 23.

In order to overcome the problems of the prior art anchor designs noted above, the present applicant has developed a new anchor design shown in FIGS. 23–30. The shortcomings of the prior art are overcome by modifying the orientation of the wing members or barbs to ensure that the external ends of the wing members (i.e., the portions which contact inner surface 102 of the cortical bone) have an angular relationship corresponding to the angular relationship between bore 13 and surface 102 (to be further described in detail below). Thus, as best shown in FIGS. 24 and 25, anchor 139 comprises cylindrical body 140, at least three wing members (barbs 141, 142 and 143), and aperture 150 positioned in tab member 151. Body 140 is similar to that of the prior art designs, however distal end 160 may be rounded since it is relatively easy to urge distal end 160 into cancellous bone as needed. The conical shape of the prior art design, however, will certainly work. Proximal end 161 is preferably perpendicular to longitudinal axis 162 of body 140 to thereby provide a flat proximal end surface which may cooperate with the new anchor-insertion tool to be described herein. Aperture 150 serves the same purpose described previously (i.e., a means for attaching a suture to the anchor), and once again the surfaces and edges of aperture 150 should be as smooth as possible to prevent fraying of the suture. In fact, aperture 150 may even be highly polished or even coated to reduce friction.

Figure 26:
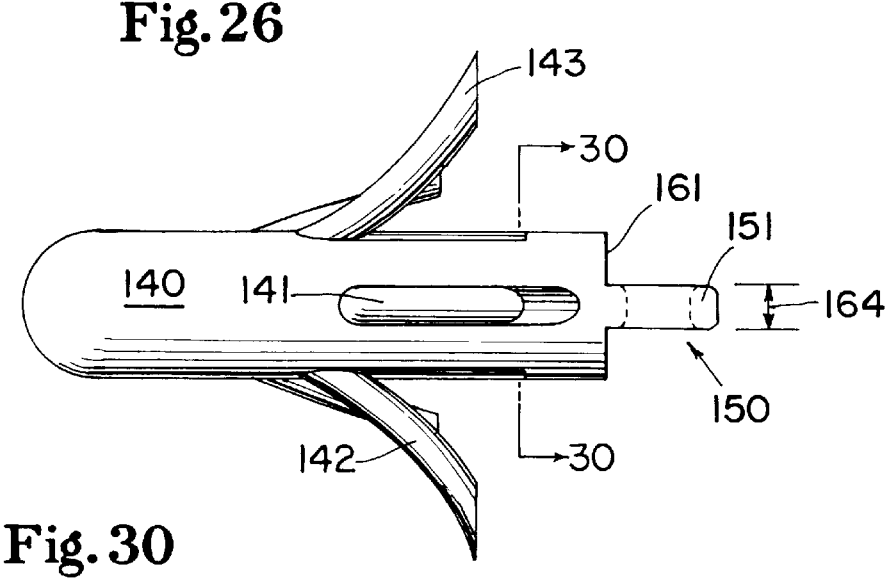
FIG. 26 is a top plan view of the anchor of FIG. 23.

Tab member 151, as shown in FIGS. 24–26, preferably has a height 163 corresponding approximately to the diameter of body 140 and a width 164 less than the diameter of body 140. The length 165 of tab member 151 should be sufficient for aperture 150 to permit a size 0 suture to be passed therethrough. It is also preferred that the length of tab member 151 extend perpendicularly away from proximal end 161 to facilitate cooperation and mating with the anchor insertion tool to be described.

As mentioned above, the most significant feature of the anchor shown in FIGS. 23–30 is the arrangement of the wing member or barbs. As is the case with the prior art anchor design, the barbs may be elastically flexed (i.e., have memory) from the normal deployed position (as shown in the figures), to a compressed position. In the deployed position, the barbs preferably curvilinearly extend radially and axially away from body 140, as shown. In the compressed position, the barbs are substantially straightened to permit insertion of the anchor into a bore created in bone in the manner of the prior art (see, for example, U.S. Pat. Nos. 5,207,679 and 5,217,486 both of which are herein incorporated by way of reference). To facilitate compression and insertion, a plurality of channels 170 are provided along the length of body 140. One of channels 170 is positioned beneath each of the wing members, and is aligned therewith. Each of the channels is further sized so as to accept at least a portion of, and preferably the entirety of the corresponding wing member aligned therewith. In this manner, when a wing member is compressed during the anchor insertion process, the compressed and straightened wing member will be positioned entirely within channel 170 positioned adjacent the wing member.

With the wing members in this compressed state, the diameter of the anchor will be equivalent to that of body 140, thereby permitting the anchor to be inserted into a bore having a diameter only slightly greater than body 140. As the wing members extend into the bore beyond interior surface 102 of the cortical bone, the wing members will return to their deployed position, since the cancellous bone is not sufficiently hard to resist the spring-back of the wing members due to their inherent elasticity (or memory). As shown in FIG. 23, since the diameter of bore 13 is only slightly greater than body 140, the external ends of the wing members will abut against interior surface 102 thereby preventing removal of the anchor from the bore. For example, external end 144 of barb 141 is shown in FIG. 23 as resting against interior surface 102.

Figure 30:
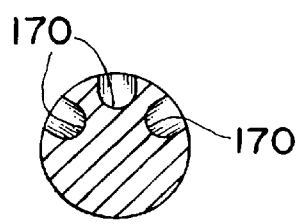
FIG. 30 is a cross-sectional view of the anchor of the present invention taken along the line 30—30 of FIG. 26.

The cross-sectional profile of channels 170 is shown in FIG. 30, which is a cross-sectional view of the anchor of FIG. 26. As shown in this view, channels 170 are preferably sufficiently deep to permit an entire wing member to be compressed into the channel. In addition, as shown in FIG. 24, the length of each channel 170 is only sufficiently long to contain the entire corresponding wing member when the latter is compressed, Thus, channels 170 may be of different lengths depending upon the various lengths of the corresponding wing members. End 171 of channel 170 (see FIG. 24) may also be angled in relation to the longitudinal axis 162 as shown in order to correspond with the external ends of the wing members, should these external ends be angled in the manner to be described.

Figure 25A:
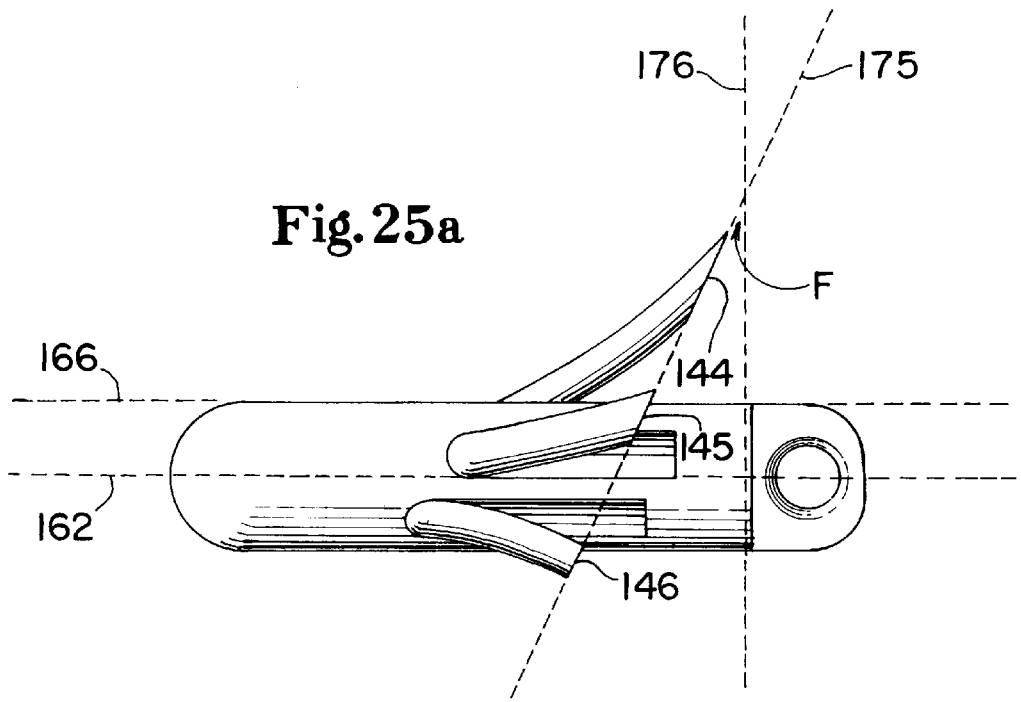
FIG. 25a is another side plan view of the anchor of FIG. 23.

In order to ensure that at least a portion of the external ends of each wing member contacts interior surface 102 of the cortical bone adjacent bore 13 when bore 13 is positioned non-perpendicularly to outer surface 100 of the pubic bone, at least a portion of the external end of each wing member is aligned along first imaginary plane 175 extending through body 140 (see FIG. 25a). In the prior art anchor designs this imaginary plane is perpendicular to longitudinal axis 162, thereby evenly aligning all of the external ends of the wing members. In the anchor of the present invention, however, first imaginary plane 175 extends through said body at an angle to transverse cross-section 176 through body 140, wherein cross-section 176 is perpendicular to longitudinal axis 162. As will be understood, angle F of FIG. 25a is preferably substantially equivalent to angle X of FIG. 23, thereby ensuring that at least a portion of the external end of each barb will contact interior surface 102 of the cortical bone adjacent bore 13. Thus, angle F is preferably between about 20° and about 60°, most preferably about 45°. The external ends of the wing members are more preferably tapered as shown so that the entirety of each external end will lie along first imaginary plane 175. Thus, external ends 144, 145 and 146 of corresponding barbs 141, 142, and 148 are aligned along plane 175, thereby adding further support when the anchor is secured within bore 13.

As will be more fully understood later, it is helpful at this point to also define the top of the anchor by a top-line 166 which extends along the surface of body 140 parallel to longitudinal axis 162. First imaginary plane 175 intersects top-line 166 at the point of intersection between the surface of body 140 and imaginary plane 175 which is nearest to proximal end 161. In other words, therefore, the barb extending from body 140 at point nearest to top-line 166 will also have an external end which is closest to proximal end 161. The further from top-line 166 that a barb extends from body 140, the further its external end will be from proximal end 161. The upper portion of body 40 is defined as that half of body 40 nearest to top-line 166, and the lower portion is therefore the remainder.

To provide the alignment described above, the wing members may extend from the anchor body in a number of fashions. Most preferably, however, each barb should be of a similar length in order to provide similar flexing characteristics for each barb thereby ensuring that the anchor will be urged straight into the bore. Thus, each wing member preferably extends from body 140 along a second imaginary plane extending through body 140 at an angle to cross-section 176. As will be understood, the angle between this second imaginary plane and cross-section 176 should be approximately equivalent to angle F of FIG. 25a. Alternatively, the wing members may extend from the anchor body at points equidistant from proximal end 161 (i.e., along a plane extending perpendicular to longitudinal axis 162). In order to provide the proper alignment for the external ends of the barbs, however, the length of the barbs in this embodiment would necessarily not all be equivalent to one another.

Figure 27:
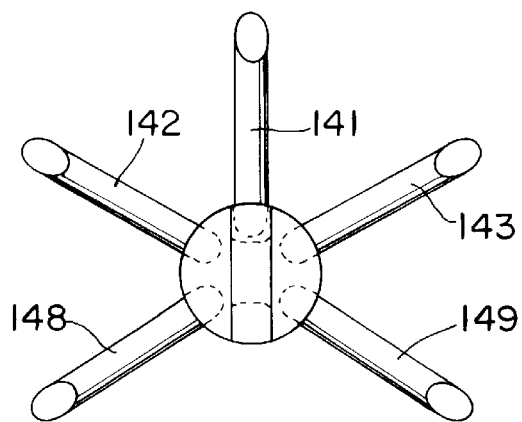
FIG. 27 is an end plan view of the anchor of FIG. 23, viewed from the proximal end towards the distal end.
Figure 28:
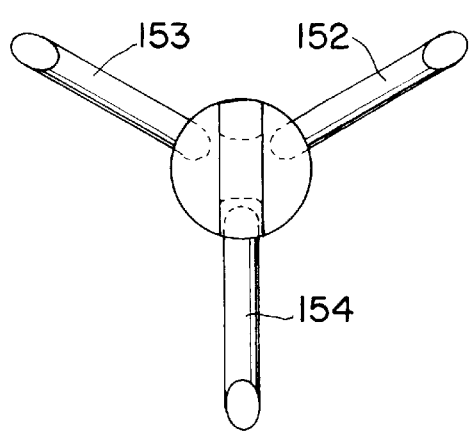
FIG. 28 is an end plan view of another embodiment of an anchor according to the present invention, viewed from the proximal end towards the distal end.
Figure 29:
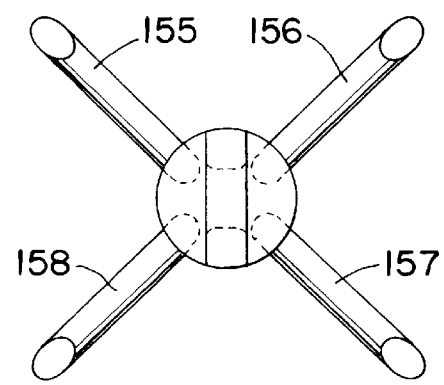
FIG. 29 is an end plan view of another embodiment of an anchor according to the present invention, viewed from the proximal end towards the distal end.
Figure 39:
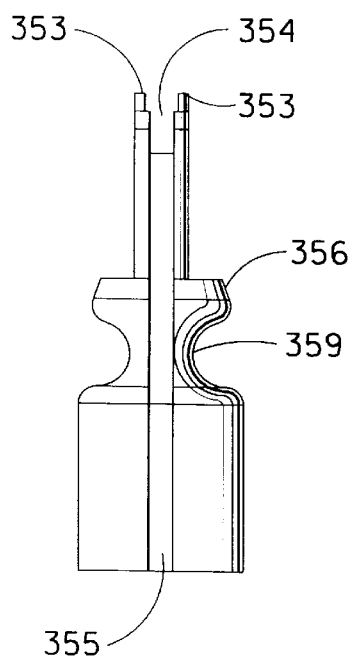
FIG. 39 is a top plan view of the tip portion of the anchor-insertion tool of FIG. 37.

In order to provide proper support during use, various configurations and numbers of barbs may be employed. Three preferred arrangements are shown in FIGS. 27–29. In the embodiment of FIG. 27, which corresponds to that of FIGS. 23–26, five barbs are employed. Thus, barbs 141,142, and 143 extend upwardly away from the upper portion of body 40, while barbs 148 and 149 extend downwardly away from the lower portion. When the anchor is viewed from the proximal end towards the distal end (FIG. 27–29), it is seen that barb 141 is substantially aligned with the top-line of body 140. To simplify the description, this will be defined as the 12 o'clock position in terms of a standard clock face. Thus, barb 141 is at about 12 o'clock, barb 142 is between about 10 and 11 o'clock, barb 143 is between about 1 and 2 o'clock, barb 149 is between about 4 and 5 o'clock, and barb 148 is between about 7 and 8 o'clock. It should be pointed out that whenever an odd number of barbs are employed, it is preferable that a greater number of barbs extend from the upper portion of the body rather than the lower portion, since further support is needed in this area.

In the embodiment of FIG. 28, three barbs (152, 153 and 154) are employed, two of which extend from the upper portion of body 140. Preferably, barb 153 is between about 10 and 11 o'clock, barb 152 is between about 1 and 2 o'clock, and barb 154 is at about 6 o'clock. In the embodiment of FIG. 29, four barbs (155, 156, 157 and 158) are utilized, two extending upwardly away from the upper portion of body 140, and two extending downwardly away from the lower portion of body 140. Preferably, barb 155 is between about 10 and 11 o'clock, barb 156 is between about 1 and 2 o'clock, barb 157 is between about 4 and 5 o'clock, and barb 158 is between about 7 and 8 o'clock. It should be noted that any of a number of alternative configurations are possible, and the three shown are merely exemplary of the simplest and preferred embodiments.

The anchor of the present invention may be made of any of a number of materials, however titanium or titanium alloys are preferred. The anchor is also preferably singularly molded, however the wing members may be formed separately and attached to body 140 during the assembly process. For example, the wing members or barbs may be attached to body 140 in the manner described in U.S. Pat. Nos. 5,207, 679 and 5,217,486. It is preferred, however, that the barbs comprise wire-like members, and may even be formed from titanium or nickel-titanium wires in a known fashion.

As also discussed previously, aperture 150 of anchor 139 is designed so that suture 180 may pass therethrough. In this fashion, two suture tails will extend from aperture 180, and may be used in the manner previously described to elevate the periurethral tissue at the UVJ, for example. It is important during such a procedure, however, that the suture be protected from nicks and other abrasions which would compromise suture strength. While the proximal end of the anchor shown in FIGS. 23–30 may be modified to that shown in FIGS. 3–4 so that the anchor-insertion tool of FIGS. 8–10 can be employed therewith, Applicant has developed yet another anchor-insertion tool which can be employed with the anchor design shown in FIGS. 23–30. This new anchor-insertion tool not only protects the suture, it also facilitates proper alignment of the anchor within the bore and also provides a means for tensioning the suture tails in the manner shown in FIG. 20.

An anchor-insertion tool according to the present invention is shown in FIGS. 31–35, and comprises a rigid elongate member 250 having:

anchor-receiving tip 252 hollow cylindrical intermediate portion 253 having distal end 260 adjacent anchor-receiving tip 252, intermediate portion 253 preferably having a diameter greater than the diameter of tip 252 handle 251 attached to intermediate portion 253 at the end opposite anchor-receiving tip 252 passageway 254 providing communication between the interior of intermediate portion 253 and the exterior of the tool Since anchor-receiving tip 252 is also preferably hollow and its interior is in communication with the interior of intermediate portion 253, an anchor having a suture extending therefrom may be secured on tip 252, and the suture (preferably a pair of suture tails) will extend through tip 252, through at least intermediate portion 253, and through passageway 254. As shown in FIG. 31, passageway 254 is preferably provided in handle 251 and terminates on rear face 255 of handle 251. Since passageway 254 is in communication with the interior of intermediate portion 253, the suture tails may extend along the entire interior length of the tool, and exit at rear face 255 of handle 251. Thus, as shown in FIG. 32, suture tails 260 and 261 extend from anchor 139 held on tip 252, through the entire interior of the tool, and exit at rear face 255. Although the suture tails may exit from the interior of the tool at various other locations, rear face 255 provides a location convenient for the surgeon during laparoscopic urethropexy and similar procedures. In addition, the sutures are completely enclosed within the tool, and thus nicking or fraying cannot occur during the insertion process. It should be noted that the length of suture tails 260 and 261 has been shortened for purposes of clarity.

Anchor-receiving tip 252 should be structured so as to matingly engage the particular anchor being employed. In addition, as described previously, the diameter of tip 252 should be equivalent to that of the anchor body to facilitate anchor insertion. In the embodiment of FIG. 31–32, tip 252 has a slot 256 extending across the diameter of the tip and at least partially along its length, slot 256 capable or matingly receiving tab member 151 of anchor 139. Since it is critical that anchor 139 be properly aligned within the bore in the pubic bone, slot 256 prevents rotation of the anchor during the anchor insertion process. Slot 256 is preferably sized equivalent to or slightly larger than tab member 151 of anchor 139, so that tab member 151 may be placed within slot 256. Tab member 151 may be wedged within slot 256 to hold the anchor on tip 252, or alternatively, end 258 of tip 252 may be secured to proximal end 161 of anchor 139 by means of a releasable adhesive. Any FDA-approved epoxy or other adhesive may be employed, as long as the bond between end 258 and proximal end 161 may bereadily broken after the anchor has been seated within the bore merely by pulling the insertion tool away from the bore. In addition, since the suture tails are preferably tensioned between the anchor and handle 251 in a manner to be described, suture tails 260 and 261 will also act to keep tab member 151 held in place in slot 256.

As best shown in the cross-sectional views of FIGS. 33–34, the wall thickness of tip 252 should be such that suture 180 which extends through aperture 150 of the anchor tab member will not be compressed by the interior walls of tip 252 when the anchor is in place on tip 252. In other words, the interior diameter of anchor-receiving tip 252 is greater than the sum of the width of tab member 151 plus twice the diameter of suture 180. I n this manner, suture 180 will be further spared from damage during the anchor insertion process.

As will be apparent, in order to properly seat anchor 139, anchor-receiving tip 252 should have a length sufficient to ensure that all of the barbs of the anchor are inserted past the cortical bone for proper barb deployment. Since it is preferred that proximal end 161 of anchor 139 be approximately aligned with interior surface 102 of the cortical bone surrounding the bore when the anchor is properly seated within a bore (i.e., external ends of all barbs resting against interior surface of cortical bone), it will be apparent that anchor-receiving tip 252 should have a length approximately equivalent to, or slightly greater than the thickness of the cortical bone (between about 5 mm and about 8 mm). End 260 of intermediate portion 253 not only acts to drive the anchor into the bore, but also acts as a stop since its diameter is preferably greater than the anchor body and the bore into which it is being inserted. Thus, the proper length for tip 252 will ensure not only that the anchor is driven sufficiently deep within the bore to fully deploy all of the barbs, but also to ensure that the anchor is not driven too far into the bore. In the latter situation, anchor stability may be compromised, and the suture may be damaged by the edges of the bore once the surgical procedure has been completed.

In order to facilitate manipulation of the anchor-insertion tool within the laparoscope, a plurality of ridges 259 are preferably provided about the circumference of intermediate portion 253. Ridges 259 are preferably positioned adjacent handle 151, most preferably between about 5 cm and about 10 cm from the handle. Since the diameter of intermediate portion 253 is preferably slightly smaller than the diameter of the laparoscope to be employed (preferably 7.8 mm and 8.0 mm respectively), ridges 259 will assist in controlling the insertion tool during the procedures of the present invention. Preferably, ridges 259 are sized so as to cooperate with the standard rubber grommet of a laparoscope.

Handle 252 may be secured to intermediate portion 253 by any of a number of means, however it is preferable that handle 252 be threadably secured to intermediate portion 253. Thus, corresponding male and female threads are provided on the handle and the intermediate portion. Once again handle 251 preferably has curved hand grip surfaces. In this embodiment, however, handle 251 preferably has dissimilar top and bottom portions 271 and 272, respectively. If anchor 139 is secured to tip 252 such that the top-line of the anchor is aligned with top portion 271 of handle 251, the surgeon can readily ensure that the anchor will be properly inserted into the bore. As long as top portion 271 extends directly upwardly during anchor insertion, proper placement will be guaranteed. In order to facilitate alignment, bottom portion 272 of handle 251 is preferably significantly heavier than top portion 271. This weight differential will further guarantee alignment, since gravity will cause the insertion tool to rotate within the laparoscopic channel to the correct position. It should be appreciated, however, that this alignment means (i.e., and oriented handle) requires that the engagement of handle 251 with intermediate portion 253 be precise. Of course other alignment means may be provided, such as guide lines, leveling bubbles, and the like.

As mentioned previously, providing tension in the suture tails extending from the anchor will not only help in maintaining the anchor on anchor-receiving tip 252, but will also assist during the suture retrieval step shown in FIG. 20 (i.e., when the insertion tool has been partially removed from the laparoscopic channel). Proper tensioning can be achieved by means of at least one notch into which the suture tail(s) may be wedged. Preferably, the notch(es) are positioned adjacent said passageway so that the suture tails may extend through the passageway directly into the notch(es). Thus notches 280 and 281 are preferably provided on rear face 255 of handle 251. In fact, passageway 254 preferably exits handle 251 in an elongated diamond-shaped exit 279, and thus notches 280 and 281 may comprise the opposing narrow corners of exit 279 as shown. When suture tails 260 and 261 leave passageway 254 through exit 279, each tail may be wedged within notches 280 and 281, respectively. In this manner, the tails will be tensioned between notches 280 and 281 and aperture 150 of the anchor. After the anchor has been inserted into the bore, and as the insertion tool is pulled partially out of the laparoscopically channel, suture tails 260 and 261 will slide within their respective notches, thus maintaining the desired tension in the suture tails as needed for the suture retrieval step. To further enhance the tensioning of the sutures, passageway 254 may taper from intermediate portion 253 towards exit 279, thereby providing an additional wedging of the suture tails within the final portions of passageway 254.

It should be noted that intermediate portion 253 preferably has a length of between about 52 cm and about 55 cm to facilitate its use through a laparoscope.

To facilitate a quick and proper anchor insertion process, anchor 139 and the anchor-insertion tool of the present invention may be provided to the surgeon in the loaded form of FIG. 32 (with suture attached and wedged for tensioning as shown). The anchor may even be releasably adhered to the anchor-receiving tip as shown. In this manner, the surgeon can merely open a sterile surgical kit containing preferably two pre-loaded insertion tools (i.e., anchor 139 engaged with anchor-receiving tip and suture tensioned between anchor and notches on handle 251). The pre-loaded insertion tools are sufficiently inexpensive to permit one-time use, or the manufacturer could provide a credit for the return of used anchor-insertion tools which can be sterilized and re-loaded. The surgical kit for performing laparoscopic urethropexy can also include a drill tamper tool, a suture retrieval tool, and/or one or more variously-sized templates (all of which have been described previously). In this fashion, the surgeon will have all of the tools necessary for a quick and simple urethropexy within a small sterile kit.

H. Additional Embodiment for Anchor-Insertion Tool

FIGS. 37–41 depict yet another embodiment for the anchor-insertion tool of the present invention. The anchor inserter of FIGS. 37–41 is similar in some respects to that shown in FIGS. 8–10. The principle differences are the elimination of an intermediate portion, a lengthening of the grooves, and the positioning of a depression adjacent to the tip. As will be understood shortly, these modifications are significant and provide a considerable advantage over the previously-disclosed design.

The anchor-insertion tool of FIGS. 37–41 comprises an elongate shaft 358 having a handle 351 at its proximal end, and an anchor-receiving tip 352 at its distal end. Handle 351 may be provided in any of a variety of shapes, and that shown is merely one possibility. Handle 351 may be secured to shaft 358 by means of threading, glue or other means well-known to those skilled in the art. Additionally, handle 351 may be plastic, wherein the remainder of the insertion tool is preferably stainless steel, or other appropriate material.

Anchor-receiving tip 352 is preferably similar to that shown in FIGS. 8–10, which in turn is similar to that shown in FIGS. 4–6 of U.S. Pat. No. 5,207,679. Thus, anchor-receiving tip 352 is constructed so as to matingly receive anchor 9 of FIGS. 3–4. Anchor-receiving tip 352 is cylindrical in nature, having a diameter approximately equivalent to body 40 of anchor 9. In this manner, at least a portion of anchor-receiving tip 352 may pass into the bore in the pubic bone during the anchor insertion process in order to properly seat the anchor completely within the bore.

Anchor-receiving tip 352 has a pair of guide tabs 353 extending from the end of anchor-receiving tip 352 on either side thereof. Guide tabs 353 are sized and shaped so as to be matingly received within the corresponding grooves on anchor 9. Anchor-receiving tip 352 also has a cylindrical slot 354 aligned with the longitudinal access of tip 352. Cylindrical slot 354 should correspond in size and shape to the cylindrical end of anchor 9 in order to matingly receive the same. Guide tabs 353 and slot 354 preferably apply a compressive force against anchor 9 in the manner previously described in order to hold anchor 9 on tip 352.

In order to protect the suture tails extending from anchor 9 during the anchor insertion process, a pair of grooves 355 are provided on either side of the anchor-insertion tool, and extend from tip 352 at least partially along the length of shaft 358 as shown. As compared to the previous insertion tool design, however, grooves 355 extend along a considerable portion of the length of shaft 358. In fact, grooves 355 preferably have a length sufficient to insure that the entire length of each suture tail is positioned within one of the grooves. In other words, when an anchor 9 having a suture extending therefrom is positioned on anchor-receiving tip 352, a suture tail may be placed entirely within each of grooves 355 with the suture terminating prior to end 402 of groove 355 (FIG. 37).

Figure 40:
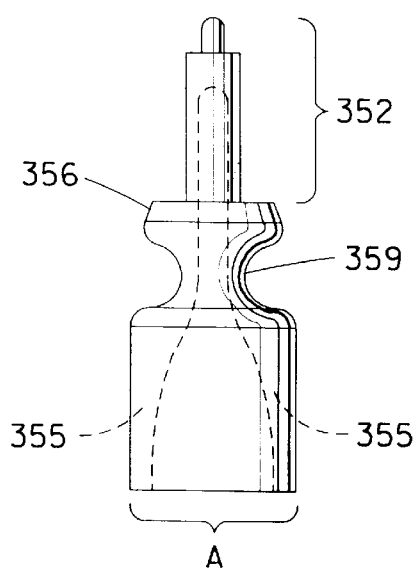
FIG. 40 is a side plan view of the tip portion of the anchor-insertion tool of FIG. 37.

As best shown in FIG. 40, grooves 355 also preferably taper in the manner described previously. On tip 352, grooves 355 should be sufficiently deep to ensure that the suture does not extend above the surface of the tip. In other words, the sutures will be completely hidden within the grooves along anchor-receiving tip 352. A distal depression 359 is provided adjacent tip 352, and grooves 355 preferably begin to taper outwardly just prior to distal depression 359. Although grooves 355 should be at least as deep (as measured from the surface of the shaft 358) as the diameter of the suture, the depth of grooves 355 in the region of depression 359 should be such that a portion of the suture tails will pass through depression 359. In this manner, an 0-ring or other retaining band may be secured about depression 359 in order to slidably hold the suture tails within grooves 355. Grooves 355 continue to taper outwardly beyond distal depression 359, and thus, the distance A between grooves 355 will increase. This provides additional strength and rigidity to shaft 358.

The anchor-insertion tool of FIGS. 37–41 also has one or more depressions 360 which extend about the circumference of shaft 358 and intersect grooves 355 as shown. Depressions 360 are sized to accommodate a retaining band, such as O-rings 361, in order to slidably hold the suture tails within grooves 355. Thus, depressions 360 should have a depth less than that of grooves 355. Grooves 355 in the region of depressions 360 should also be sized such that the O-rings 361 may compressively and slidably hold the suture tails within grooves 355. Therefore, the difference in depth between grooves 355 and depressions 359 and 360 should be less than the diameter of the suture. A suture positioned within 355 will thus be slidably held between O-rings 361 and grooves 355. In this manner, the anchor insertion method previously described can be readily accomplished with the anchor-insertion tool of FIGS. 37–41, wherein tension is applied to the suture tails when the insertion is removed from a bore within which the anchor has been secured.

In the embodiment shown in FIGS. 37–41, the retaining bands, or O-rings 361, may be sized such that they act as a grommet during the anchor insertion process. In other words, after anchor 9 has been loaded upon the anchor insertion tool, the tip of the tool is inserted through a cannula (such as the operative channel of a laparoscope) in order to present anchor 9 to the bore into which it will secure. Shaft 358 is preferably only slightly smaller in diameter than the interior diameter of the cannula, and 0-rings 361 may extend above the surface of shaft 358. O-rings 361 may therefore act as a grommet within the cannula (e.g. the operative channel of a laparoscope), thereby preventing the escape of insufflation gas from the interior of the patient. Furthermore, O-rings 361 provide additional stability because of the tight fit within the operative channel of the laparoscope.

In the presently preferred embodiment, O-rings 361 preferably are sized so that they do not extend substantially above the surface of shaft 358. Although such a configuration lessens or eliminates any sealing effect caused by the O-rings, applicant has found that sealing may also be provided by the interaction of a seal placed on the end of the cannula with shaft 358. Such seals are well-known in the art, and are commonly employed for this purpose. Additionally, since the suture tails are carried entirely within grooves 355, a relatively tight fit between shaft 358 and the cannula may be maintained, thereby further lessening the escape of insufflation gas. Furthermore, end 402 of grooves 355 is located well ahead of handle 351, preferably at a distance sufficient to ensure that during the normal insertion process grooves 355 (and hence the suture tails present therein) will remain entirely within the patient or the cannula. In this fashion, grooves 355 will not permit insufflation gas to escape from the interior of the patient.

Figure 41:
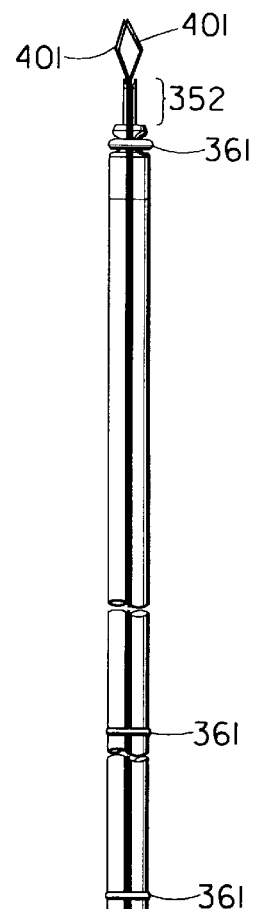
FIG. 41 is a top plan view of the anchor-insertion tool of FIG. 37, with a pair of suture threaders loaded therein.

Often it is difficult for a surgeon to thread sutures into needles and the like while performing surgical procedures, particularly because of the difficulties caused by surgical gloves. In order to alleviate such problems, applicants have also developed a unique method for threading the sutures onto the anchor-insertion tool. As best shown in FIG. 41, a pair of suture threaders 400 are pre-loaded on the anchor-insertion tool. Similar suture threaders are employed for threading surgical needles and the like. In the present case, each suture threader 400 comprises a length of wire which is bent at its middle to form a loop 401. The opposite ends of the threader are then secured to a pull tab (or handle) 357. In the present case, both suture threaders are preferably connected to a single pull tab 357 as shown. Each suture threader is inserted into one of the grooves 355 as shown, with its loop 401 extending beyond and adjacent tip 352. At its opposite end, each threader preferably extends beyond end 402 of grooves 355 such that pull tab 357 may be readily accessed. O-rings 361 are then secured about the anchor-insertion tool within depressions 359 and 360. This results in each suture threader being slidably held within one of grooves 355 beneath O-rings 361 as shown.

In order to utilize the suture threaders, an anchor is first secured on top tip 352. Since tip 352 will orient the anchor in a pre-determined manner, loops 401 of the threaders as shown in FIG. 41 will align with aperture 43 on anchor 9. In this manner, the surgeon or other medical personnel may simply thread the suture straight through one of loops 401, aperture 43 on anchor 9, and thereafter through the second loop 401. Once threaded, the suture is centered within aperture 43, and then pull tab 357 is grasped. As pull tab 357 is retracted in the direction of handle 351 away from grooves 355, the suture tails will be pulled into grooves 355 by loops 401. As the surgeon continues to retract pull tab 357, the sutures are threaded into grooves 355 beneath O-rings 361, thereby loading the suture onto the device in the proper manner. Thus, the suture threaders provide a convenient way for the surgeon to prepare the anchor-insertion tool for the surgical procedures of the present invention.

As discussed previously, after anchor 9 has been secured within a bore in the pubic bone, the anchor-insertion tool can be retracted away from the anchor by means of handle 351. When the insertion tool is retracted in this way, the suture tails will slide between O-rings 361 and grooves 355 such that the suture tails will extend between the anchor and the tool after this retraction step. The tool should not be completely withdrawn at this point, however, since the suture tails should be permitted to extend between the tool and the anchor in order to allow suture retrieval as shown in FIG. 20. It is also preferred that the suture tails and grooves 355 be sufficiently long so that the insertion tool can be retracted as shown in FIG. 20 while ensuring that the suture remains beneath all of the O-rings 361. In this manner, the suture tails will be controlled and the barbs of the anchor will be deployed by means of the tensioning of the suture tails. In addition, this insures that the O-rings 361 will remain within the cannula or operative channel of the laparoscope for sealing purposes, if any. Finally, shaft 356 also terminates in distal end 358 which is shown as being tapered. The tapering of distal end 356 provides improved laparoscopic vision during the insertion process. In addition, tapered distal end 356 acts as a stop during the anchor insertion process, thereby insuring that the anchor is inserted to the proper depth.

In the embodiment shown in FIGS. 36–38, anchor-receiving tip 352 once again preferably has a length sufficient to insure proper anchor depth. Since anchor-receiving tip 352 preferably has a diameter equivalent to that of anchor 9, which in turn is only slightly smaller than the bore in the pubic bone, distal end 356 acts as a stop during the insertion process. Therefore, the length of anchor-receiving tip 352 should be approximately equal to the depth of the bore minus the length of the anchor. Shaft 358 should be of a length sufficient to permit the tool to be effectively employed through a laparoscope. Thus, shaft 358 has a length of between about 45 and about 60 cm, preferably between about 50 and about 52 cm. The length of the grooves should be sufficient ensure that the entire length of both suture tails can be positioned entirely within one of the grooves, while also ensuring that the grooves remain either within the abdominal cavity or within the operative channel of the laparoscope when the insertion tool is partially retracted as shown in FIG. 20. This ensure that insufflation gas cannot escape through the grooves. Preferably, the grooves between about 25 cm and about 30 cm from the tip. While it is preferred that a at least one depression be positioned adjacent the tip, any number of additional depressions may be provided anywhere along the length of the shaft. Two or three additional depressions 360 are preferred as shown in the accompanying drawings.

Alternative Surgical Templates

Although the previously-described template configurations are well-suited for retropubic bladder neck suspensions, whether performed laparoscopically or via traditional open procedures, Applicant's template of the present invention may be readily adapted to any of a variety of surgical procedures. In particular, the present invention provides a template for guiding the placement of a fixation device or medical instrument through at least a portion of the tissue adjacent the vagina. Placement of the fixation device or medical instrument may be directed through the tissue at a predetermined location or in a predetermined relationship to a landmark within the patient's body. For example, the template of the present invention may be used to direct the placement of a fixation device or medical instrument through the tissue adjacent the patient's vagina in a predetermined relationship to the patient's urethra, particularly the UVJ portion of the urethra. In the embodiments previously described, the sutures (i.e., the fixation device) are directed through the periurethral tissue in a predetermined relationship to the UVJ.

Preferably, the patient's anatomy regulates and defines the orientation of the template at least partially within the vagina, thereby ensuring that the fixation device or medical instrument is placed through the tissue at the desired, predetermined location. More preferably, at least part of the template of the present invention nests within the vagina, with a portion of the template conforming to the shape and dimensions of a portion of the vagina and/or the urethra in order to direct the orientation of the template during use. In the embodiments previously described, for example, the trough of the body generally conforms to the shape and size of the urethra and the vaginal wall around the bottom portion of the urethra. In addition, the Foley catheter (or other elongate member) conforms generally to the shape and dimensions of the urethra, and thus acts to further direct the orientation of the template within the vagina. Thus, the template of the present invention preferably has an elongate member which may be inserted into the urethra of a patient to thereby position the template in the desired orientation. The elongate member may be an integral part of the template, or may be a separate device attached to a portion of the template (e.g., the Foley catheter previously described).

In contrast to the template of the present invention, devices such as that shown in U.S. Pat. No. 5,507,796 to Hasson merely act as probes for designating a location for the fixation device, wherein this location must be selected by the surgeon. In essence, the probe of Hasson is merely a substitute for the surgeon's (or an assistant's) finger, and is therefore no more accurate than the "finger probe" technique. In contrast, the template of the present invention precisely directs placement of the fixation device or surgical instrument through the tissue at a predetermined location or in a predetermined relationship to a landmark within the patient's body. The template guides placement of the fixation device, rather than the surgeon doing so (as in the Hasson patent).

Figure 49:
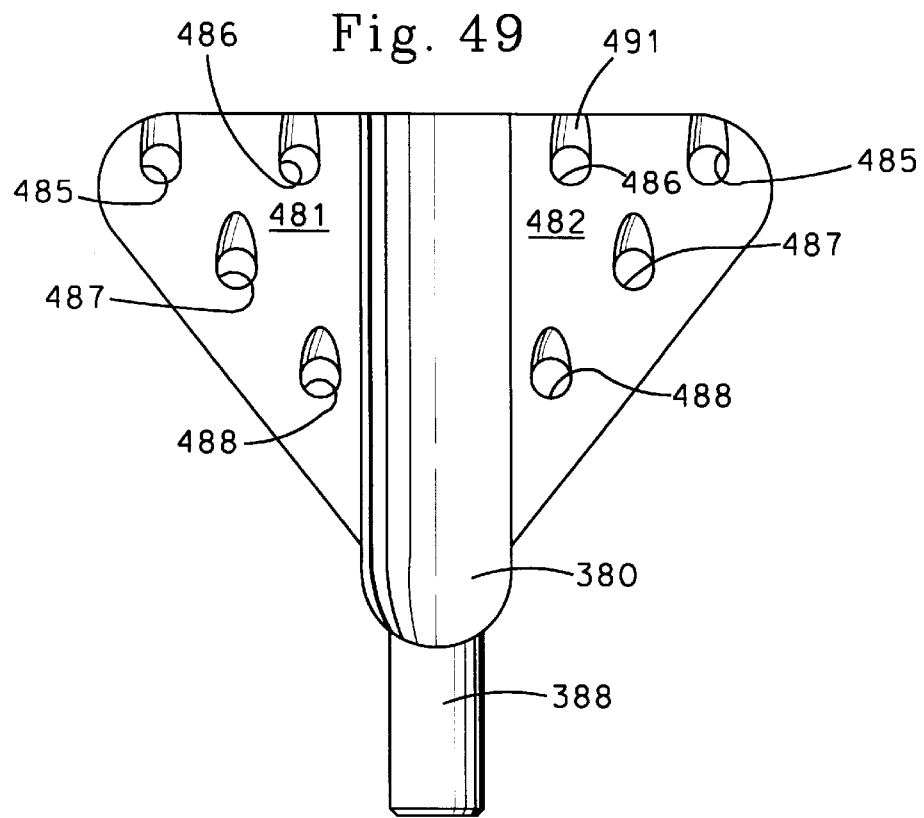
FIG. 49 is a top plan view of an alternative embodiment of the surgical template of the present invention.
Figure 50:
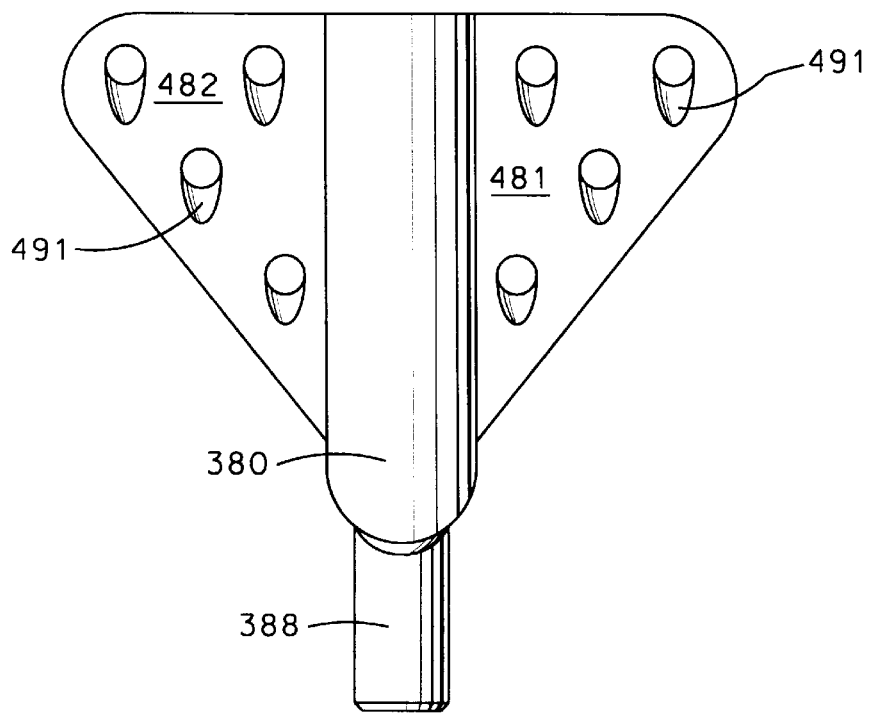
FIG. 50 is a bottom plan view of the surgical template of FIG. 49.

FIGS. 49 and 50 are top and bottom plan views, respectively, of yet another alternative template configuration. The embodiment of FIGS. 49 and 50 is nearly identical to that of FIGS. 42–43, however a total of eight guides are disposed in a predetermined spacial relationship to the body of the template. In this case, the guides once again comprise apertures through which a fixation device such as a suture may be passed. These apertures are arranged in a predetermined spacial relationship to the body, which once again comprises trough 380 and alignment member 388. The apertures are preferably provided on wing members 481 and 482 which once again extend away from opposite sides of trough 380, as was the case in the previously-described template embodiments. The size of wing members 481 and 482 has also been increased slightly in order to not only accommodate four apertures on each wing member, but also to enable the apertures to be positioned a sufficient distance from each other. Additionally, bevels 491 are provided adjacent each of the apertures on both the topside and underside of the wing members. These bevels will facilitate manipulation of a suture retriever, needle or other surgical instrument which extends through the apertures. The bevels permit these implements to be moved to a more acute angle with respect to the surface of the wing members when the implement is extending through an aperture, as described previously.

The template of FIGS. 49–50 can be used in a variety of gynecological procedures, including the urethropexy procedure described in detail above. For example, a surgeon may desire to employ a pair of bone anchors on each side of the pubic symphysis for additional support, and therefore four apertures in each wing member are required. The suture tails extending from a first anchor positioned in the pubic bone to one side of the pubic symphysis may be retrieved through first and second apertures 485 and 486 in the manner previously described. The suture tails extending from a second anchor positioned to the same side of the pubic symphysis are then retrieved through third and fourth apertures 487 and 488, respectively. The process is repeated on the opposite side of the urethra, the template is removed, and the two tails of each suture are then tied within the vagina in the same manner as before, thereby providing additional support. First and fourth apertures 485 and 488 should be positioned between about 1 and about 2 cm from the centerline of trough 380. The distance between first and second apertures 485 and 486, as well as the distance between third and fourth apertures 487 and 488, should also be between about 1 and about 2 cm in order to ensure proper spacing between the locations where the suture tails penetrate the periurethral tissue.

Figure 51:
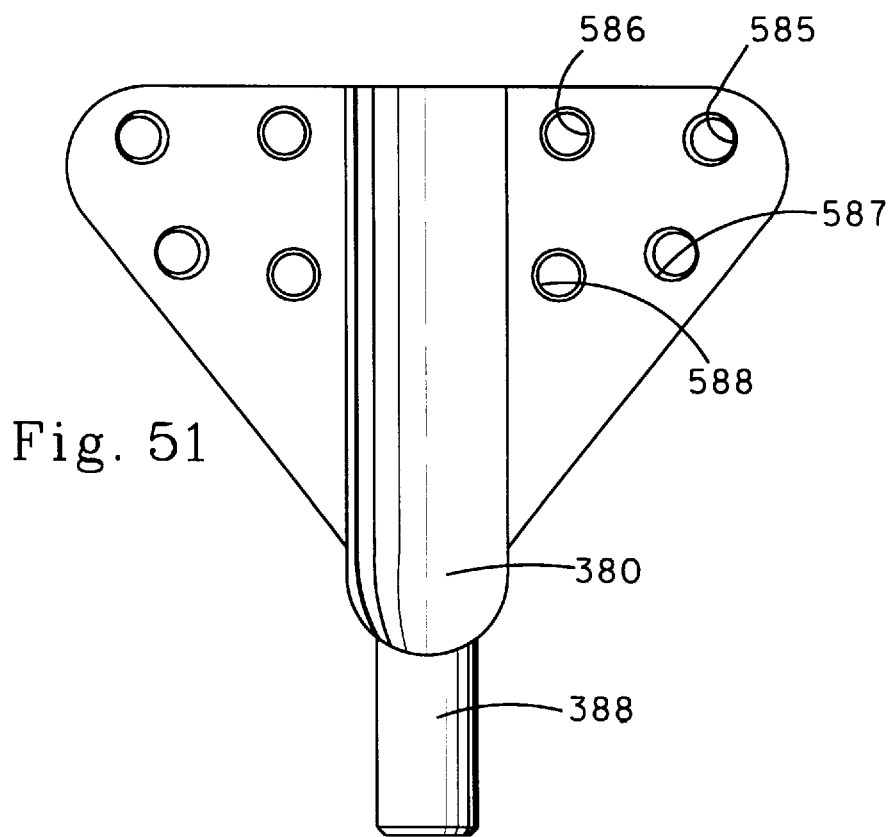
FIG. 51 is a top plan view of another alternative embodiment of the surgical template of the present invention.

It should be pointed out that the orientation of the four apertures to one another in the embodiment of FIGS. 49–50 is merely exemplary of one possible arrangement, and this arrangement can be varied as needed without diminishing the effectiveness of the template and procedures using the template. For example, FIG. 51 is a top plan view of another template embodiment having four apertures in each wing member, including first aperture 585, second aperture 586, third aperture 587, and fourth aperture 588. The aperture configuration of FIG. 51 provides for an alternative suture placement arrangement, and is particularly suited for a Burch procedure as more fully described below. The template of FIG. 51 can be used, however, in other procedures described herein, including the laparoscopic urethropexy procedure using bone anchors described above.

Although the templates of the present invention have heretofore only been described in conjunction with a urethropexy procedure employing bone anchors and sutures extending therefrom, the use of these templates is not so limited. Thus, the templates of the present invention may be employed in any surgical procedure wherein a fixation device is placed through at least a portion of the tissue adjacent the patient's vagina (including the vaginal wall and the periurethral tissue), and is thereafter connected relative to a structure within the patient's body. The fixation device can comprise any of a number of items, including a filamentatious (i.e., filament-like) member and an urethral sling. The filamentatious member can be a suture as previously described, or even a thread or wire. In fact, a thread, wire or similar filamentatious member may replace the suture in the previously-described procedures. The urethral sling is a fixation device employed in the urethral or pubovaginal sling procedure briefly described above. In all of these procedures, however, the template acts as a guide for directing the proper placement of the fixation device in predetermined relationship to a landmark within the patient's body, such as the urethra and more particularly the UVJ. The tissue may be connected relative to a structure within the patient's body using the fixation device, and the structure used for fixation can be, for example, the pubic bone, the periosteum of the pubic bone, the pubic symphysis, Cooper's ligament, or the rectus fascia. In this manner, the success rate of such procedures will be increased due to the precise placement of the fixation device through the tissue, and, more importantly inadvertent damage to structures such as the urethra, bladder, and other delicate structures within the patient's body can be avoided.

As one example, the templates of the present invention can be readily employed during either a Burch procedure, or a needle suspension procedure, including those described by Benderev in U.S. Pat. Nos. 5,544,664 and 5,582,188. In the Burch procedure, the fixation device connects the periurethral tissue to Cooper's ligament. This procedure was developed because it is much easier to pass a needle through Cooper's ligament than the periosteum of the pubic bone. Typically, the fixation device is a suture, and various types of needles are employed for passing the suture through Cooper's ligament and the periurethral tissue. Although the Burch procedure has been accomplished laparoscopically, most are still done through a large Pfannenstiel incision due in part to the difficulty in tying sutures laparoscopically.

In a Burch procedure, a needle having a suture attached thereto is typically passed through Cooper's ligament, and then through the periurethral tissue from inside the space of Retzius into the vagina. The needle is then brought back up through the vaginal wall in spaced relationship to the point in the periurethral tissue through which the needle previously passed. Once the needle reenters the space of Retzius, the suture may be cut from the needle, and the free ends of the suture tied to one another in order to elevate the urethra to the desired angle. Preferably, however, the needle is first passed back through the periurethral tissue into the vagina, and thereafter back through the vaginal wall and the periurethral tissue into the space of Retzius. In this manner, the surgeon takes two "bites" of the periurethral tissue, with the suture actually entering the vagina for each bite. It should be pointed out that in order for the needle and suture to pass from the space of Retzius into the vagina, both must pass through not only the periurethral fascia but also the vaginal mucosa. Alternatively, the surgeon may instead merely take one or more bites of periurethral tissue without ever passing the needle into the vagina.

Figure 52:
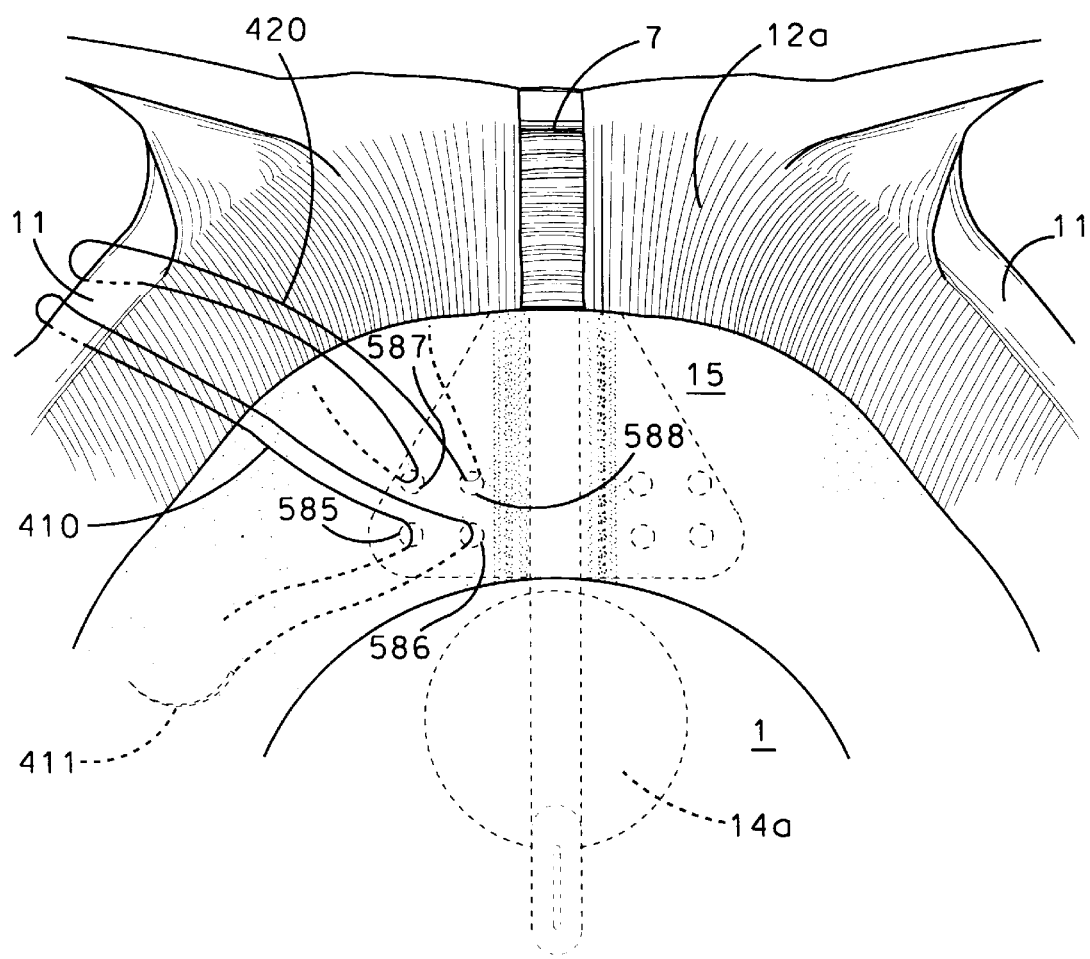
FIG. 52 is a perspective view of the space of Retzius, and illustrates a Burch procedure employing the template of FIG. 51.

The template of FIGS. 49–51 may be employed in a Burch procedure (either open or laparoscopic) in the manner shown in FIG. 52, wherein the template of FIG. 51 is shown in hidden lines. Additionally in FIG. 52, the pubic sympysis 7, the periosteum 12*a* of the pubic bone, the bladder 1, the bulb 14*a* of a Foley catheter, and Cooper's ligament 11 are all depicted. A first suture 410 is provided, and a needle 411 is swaged onto one end of suture 410. Needle 411 may be of any variety known to those skilled in the art, and may be curved or straight. Needle 411 is first inserted into the vagina and passed through aperture 585, and is directed by the aperture through the vaginal mucosa and periurethral fascia 15 adjacent thereto. Needle 411 is then passed through Cooper's ligament 11 as shown, and multiple bites may be taken if desired. Manipulation of the needle and suture may be accomplished laparoscopically or under full open vision by any of a variety of needle graspers, as is well known to those skilled in the art.

After passing through Cooper's ligament, needle 411 is passed back through periurethral fascia 15, the vaginal mucosa, and second aperture 586 back into the vagina. As will be apparent, however, the surgeon must locate aperture 586 from within the space of Retzius (either through direct vision through the surgical incision or through a laparoscope). This can be readily accomplished by any of a number of ways, such as shining a beam of light through aperture 586 in order to transilluminate the aperture within the space of Retzius. A small, flexible, fiber optic light source may be inserted into the vagina, and its beam directed against the vaginal mucosa accessible through aperture 586.

Alternatively, the suture retriever previously described may be passed through the aperture, the vaginal mucosa, and the periurethral fascia into the space of Retzius in order to snare suture 410 in the manner previously described. The needle grasper used to pass needle 411 through Cooper's ligament may also be used to provide the necessary tension in suture 410 to facilitate snaring of the suture by the suture retriever. Needle 411 will generally follow the suture into the vagina through aperture 586, or the needle may be cut from the suture once a portion of suture 410 has been retrieved into the vagina. As another less preferred alternative, the surgeon may merely insert the tip of a sharp object through aperture 586 into the space of Retzius, and then use this share object to direct passage of needle 410 back into the vagina through aperture 586. A needle grasping device having a sharp end may also be inserted through the aperture into the space of Retzius in order to grasp needle 410 and pull it back into the vagina. Finally, the surgeon may even resort to probing with needle 410 in order to locate aperture 586.

After suture 410, and optionally needle 411 have reentered the vagina, suture 410 is cut at needle 411 (if necessary). In this manner, the two tails of suture 410 both extend through the periurethral tissue into the vagina, spaced approximately 1 cm from each other. This procedure is then repeated with a second suture 420 using third and fourth apertures 587 and 588 so that both tails of second suture 420 are also present in the vagina. This process is then repeated on the opposite side of the urethra. The template is removed, and the two tails of each suture are tied to each other (e.g., the first tail of suture 410 is tied to the second tail of suture 410) in order to elevate the UVJ to the desired angle. It should be noted that first aperture 585 is preferably spaced about 1 cm from third aperture 587, and second aperture 586 is preferably spaced about 1 cm from fourth aperture 588. Such spacing is sufficient to ensure proper support of the UVJ.

As will be understood, various types of well-known suturing devices and systems may facilitate the above Burch procedure. For example, a LAURUS™ PUSH & CATCH™ Suturing System, manufactured by the Laurus Medical Corp., of Irvine, Calif. and described in U.S. Pat. No. 5,578,044 may be employed. Alternatively, a Carter-Thomason percutaneous suturing needle, manufactured by Inlet Medical, may also be used. Although these devices may simplify needle and suture passage through the tissue, the essential elements of the procedure described above remain unchanged. These devices are even more appropriate in the Burch procedure described below wherein the needle and accompanying suture do not enter the vagina.

The above-described Burch procedure can be simplified and improved, particularly when the surgeon desires to tie the suture tails within the abdominal cavity rather than within the vagina, by use of yet another alternative template design shown in FIGS. 53–60. It should be pointed out once again, however, that this template design is not limited to a Burch procedure, and can therefore be employed for an MMK, Mitek-MMK, or even a needle suspension procedure (including that of Benderev).

Once again four apertures are provided in each wing member of the template of FIGS. 53–60, however each aperture is connected to an adjacent aperture by a slit. As will be apparent, the slits allow the template to be removed after the sutures or other fixation devices have been secured in place (e.g., by tying of the suture tails). First slit 689 connects first and second apertures 685 and 686, respectively, while second slit 690 connects third and fourth apertures 687 and 688, respectively. When the template shown in the top and bottom plan views of FIGS. 53 and 54, respectively, is used in the Burch procedure previously described, suture tying may be accomplished in the abdominal cavity. The final result, however, will be similar to that shown in FIG. 52. Thus, a needle having a suture attached thereto may be first passed through Cooper's ligament, and several bites may optionally be taken. The needle is then passed through the periurethral tissue into the vagina through first aperture 685. Needle placement may be directed in the manner previously described (e.g., transillumination, suture retriever, needle grasper inserted through the aperture, etc.). The needle is then returned to the space of Retzius through second aperture 686, with the portion of the suture between the first and second apertures positioned within slit 689. The needle is then cut off, and the two tails of the suture tied to one another within the abdominal cavity. Since the suture is positioned within slit 689, the tied suture will not prevent removal of the template, as would be the case with the template of FIGS. 51–52 if suture tying were accomplished prior to removal of the template. This process may then be repeated for the three additional sutures in the same manner. The result is that the UVJ is returned to its desired elevation, and two parallel segments of suture material will extend perpendicular to the urethra on each side thereof.

The template of FIGS. 53–60 can also be used in the manner depicted in FIG. 52, with suture tying accomplished in the vagina. Thereafter the knot may be rotated into the space of Retzius, and the template removed. The template of FIGS. 53–60 may be advantageous even when suture tying is accomplished in the vagina, since the suture tails of each suture may be tied with the template in place. Thus, the surgeon need not wait until the suture tails of all four tails have been brought into the vagina before tying.

Figure 53:
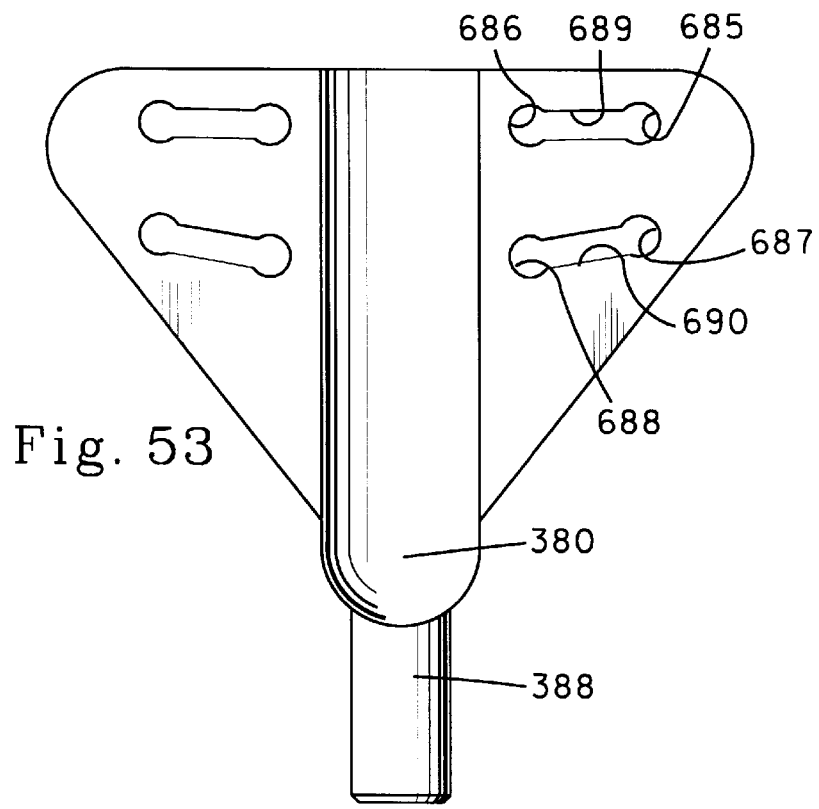
FIG. 53 is a top plan view of an another embodiment of the surgical template of the present invention.
Figure 54:
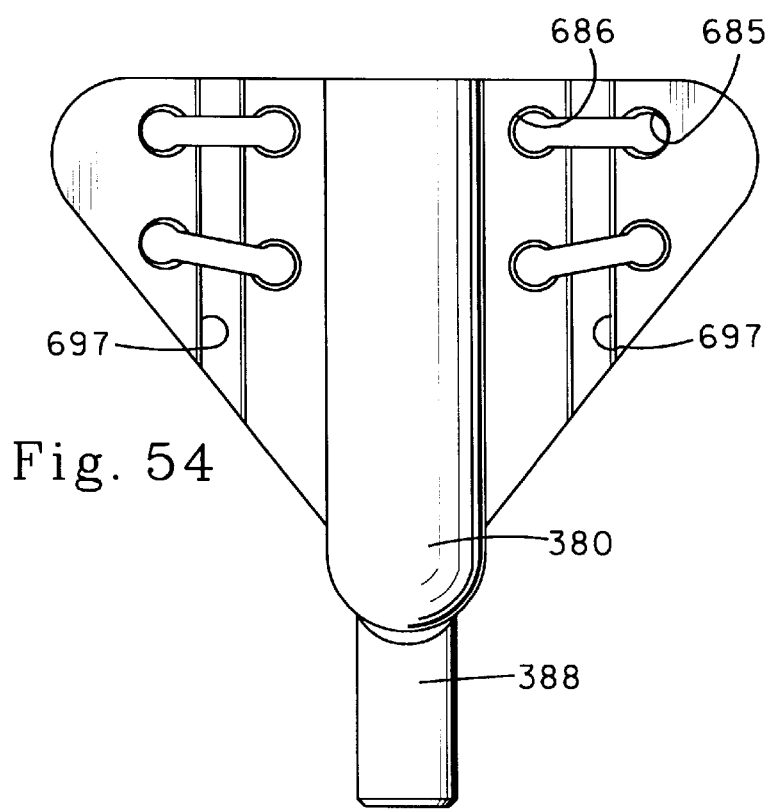
FIG. 54 is a bottom plan view of the surgical template of FIG. 53.

When the template of FIG. 53 is employed, it will be apparent that when the suture is tied, the suture will pull against the tissue beneath slot 689. This tissue, however, is very pliant, and it may be difficult to tie the sutures within the abdominal cavity so that the urethra is elevated evenly on both sides. In addition, the suture lying within slot 689 will be difficult to observe during tying, since the suture is pulled up behind the pubic bone (hence the term "retropubic"). This lack of vision will make it even more difficult to observe the degree of elevation during suture tying. In order to overcome these problems, a pair of removable support struts 691 are provided.

Figure 56:
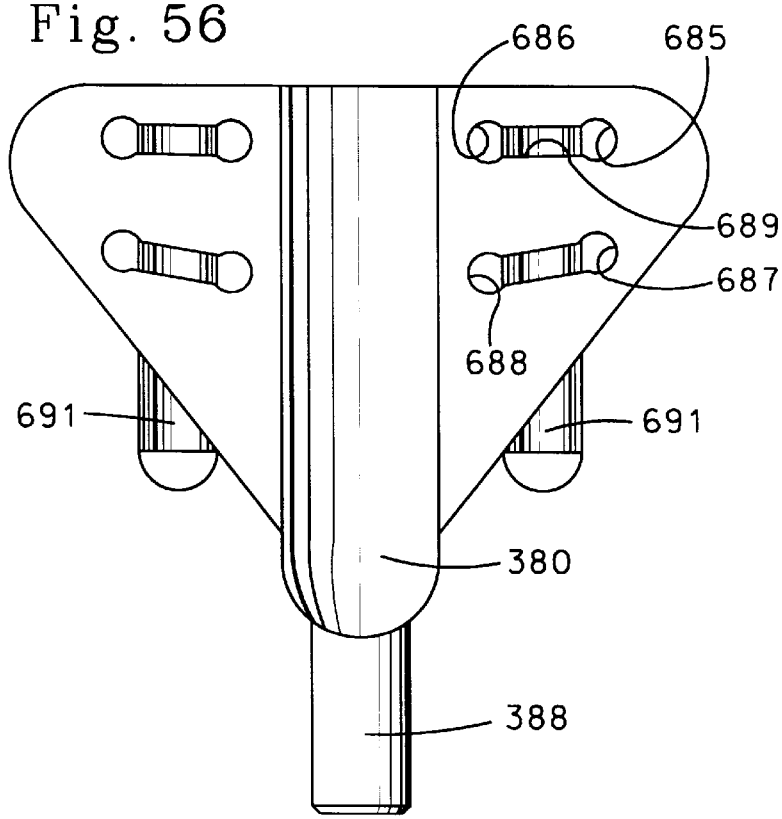
FIG. 56 is a top plan view of the template of FIG. 53, wherein a pair of support struts have been attached thereto.
Figure 55:
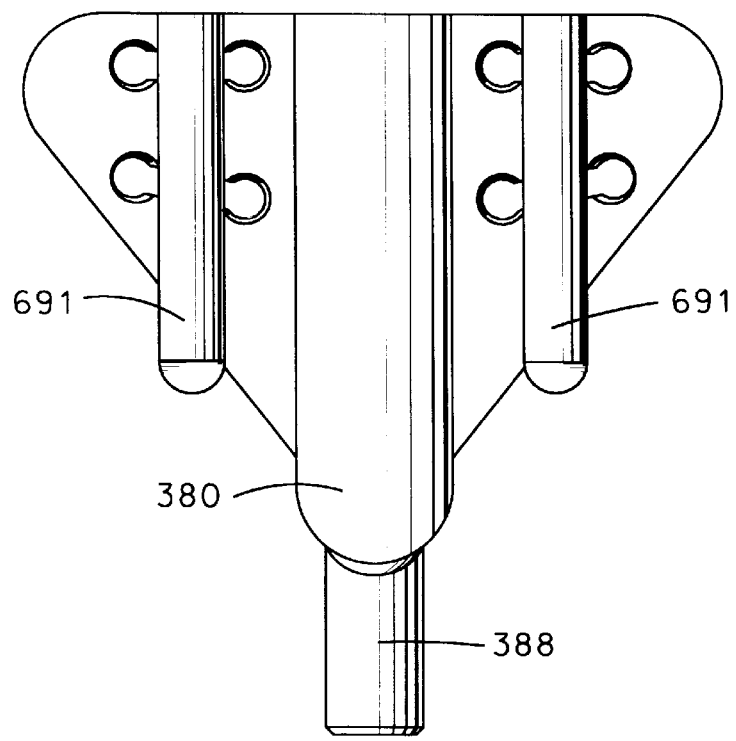
FIG. 55 is a bottom plan view of the template of FIG. 53, wherein a pair of support struts have been attached thereto.

As best shown in FIGS. 55–56, support struts 691 are removably attached to the underside of each wing member, and act to block the communication between adjacent apertures provided by the slit therebetween. For example, when the support strut is not in place, slit 689 provides communication between first aperture 685 and second aperture 686, as shown in FIG. 53. When support strut 691 is attached to the underside of the wing member, support strut 691 will block communication between first aperture 685 and second aperture 686, as shown in top plan view 56.

Figure 73:
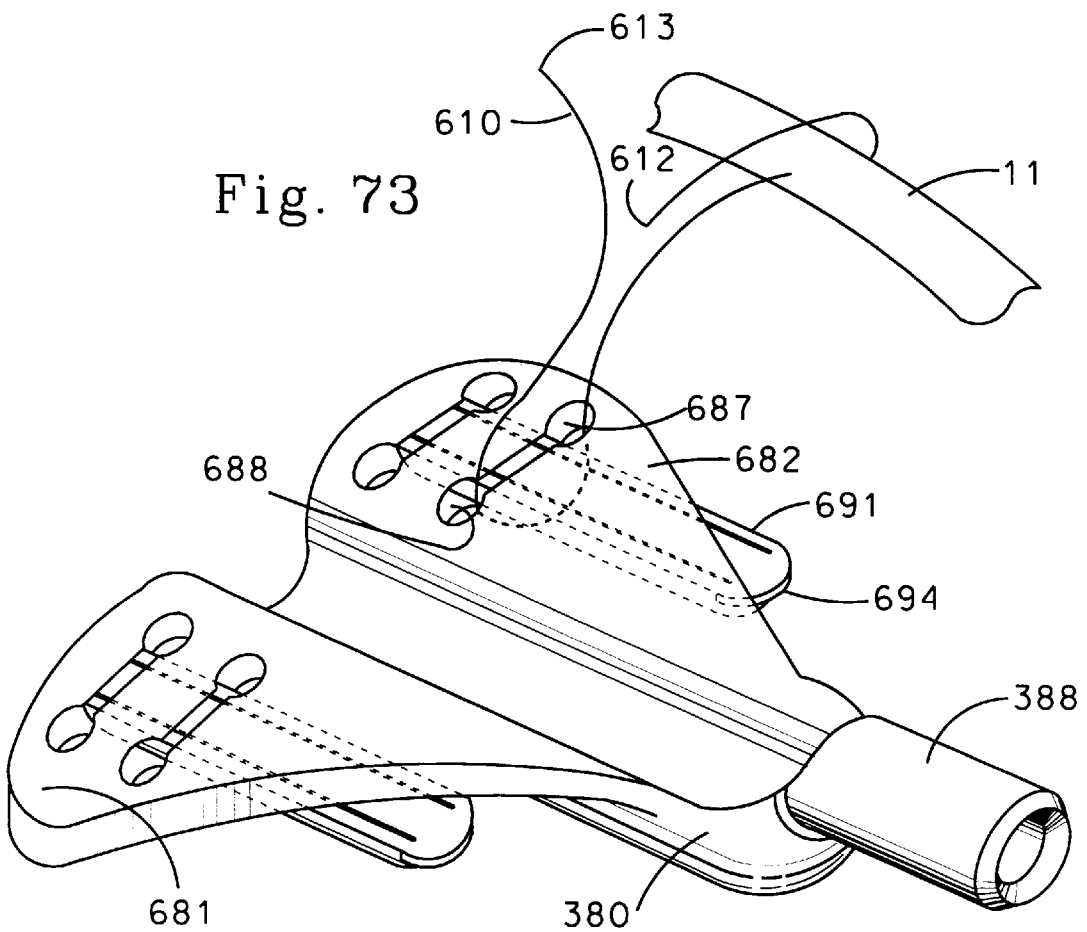
FIG. 73 is a perspective view illustrating use of the template of FIG. 53.

FIG. 73 is a perspective view of the template of FIG. 55 in use during a Burch procedure, wherein the patient's anatomy, other than Cooper's ligament 11, has been eliminated for purposes of clarity. A suture 610 has been passed through Cooper's ligament 11, and has been passed into the vagina through both third aperture 687 and fourth aperture 688 and looped around strut 691 as shown. First and second ends 612 and 613 of suture 610 may then be tied to one another in the typical fashion. Since suture 610 will bear against strut 691 during this process, the surgeon or the surgeon's assistant may monitor the elevation of the UVJ merely by observing the degree that second wing member 682 is deflected upwardly within the vagina. If strut 691 were not present, the elevation would be difficult to observe, because the pliable tissue and the pubic bone would obscure the amount of elevation being provided. In addition, upward movement of the template is much easier to observe than the upward movement of a small area of the vaginal wall.

After one side of the urethra has been elevated using a fixation device extending between the periurethral tissue and mooper's ligament, the process may be repeated on the opposite side. The surgeon or the surgeon's assistant may once again observe the elevation of first wing member 681 within the vagina, while also ensuring that the wing members are elevated to the same extent. In this manner, the surgeon can verify that the UVJ has been elevated to the proper angle, and that the elevation on each side of the urethra is substantially equivalent. Once all of the sutures have been tied and proper elevation verified, struts 691 may be removed from the template, thereby releasing the suture from the template though the slots providing communication between adjacent apertures. While the template of FIG. 73 is shown in use during a Burch procedure, the strutted template may be used in any of the procedures described herein.

Figure 57:
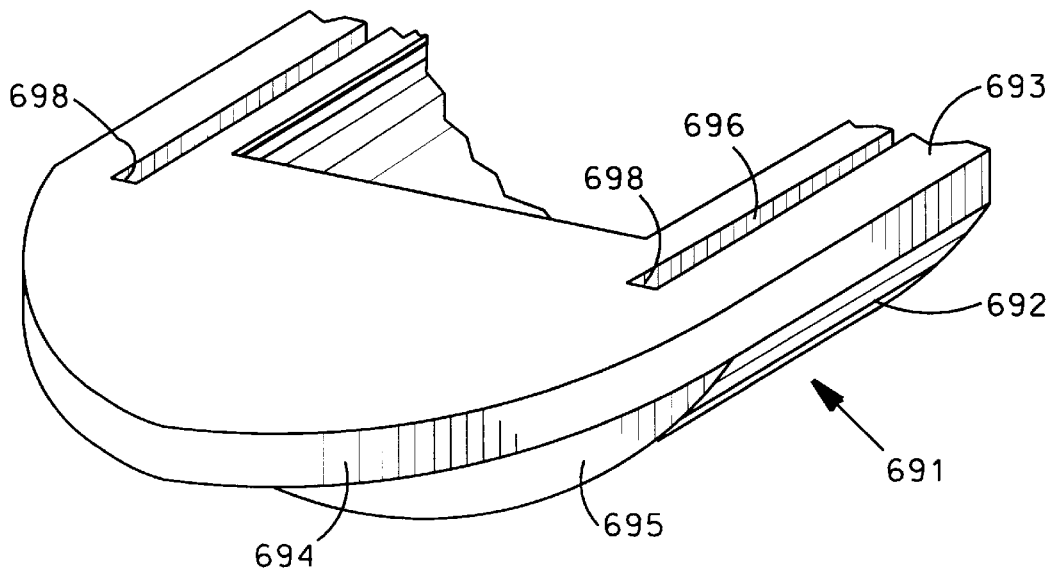
FIG. 57 is a perspective view of the front portion of a support strut for use with the template of the present invention.
Figure 58:
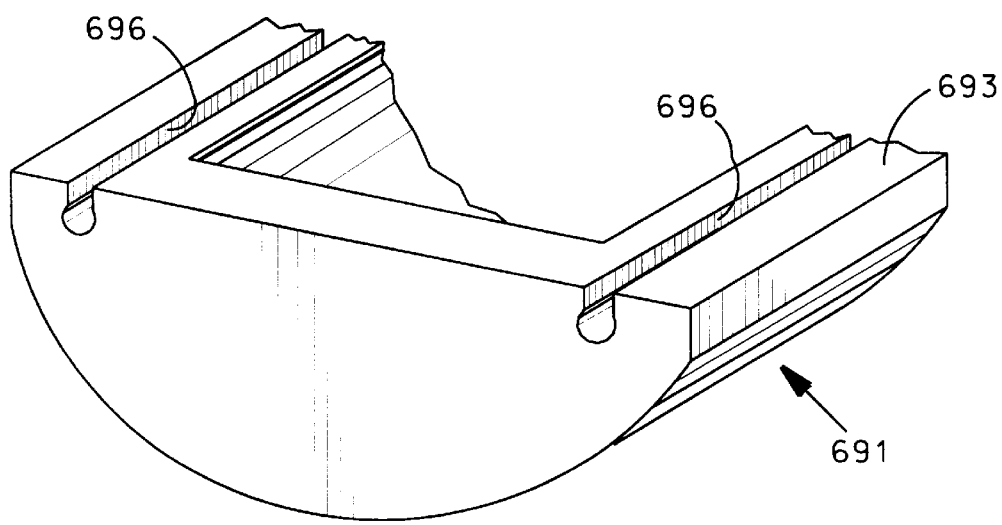
FIG. 58 is a perspective view of the rear portion of the support strut of FIG. 57.

Strut 691 is shown in more detail in FIGS. 57 and 58, which are partial perspective views of the front and distal ends of strut 691, respectfully. The preferred embodiment of Strut 691 essentially comprises a cylinder which has been cut in half lengthwise. Thus, strut 691 has a curved upper surface 692, and a substantially flat lower surface 693. Lower surface 693 may optionally be curved slightly in order to more accurately correspond to any curvature of the underside of the template wing members against which strut 691 will be attached. The interior of strut 691 may be hollowed as shown in order to account for any curvature of the underside of the wing members. Curved upper surface 692 provides a smooth surface against which the sutures or other fixation devices will bear. This smooth, curved surface will prevent any damage to the suture during the procedures of the present invention. The length of struts 691 should be chosen to ensure that both slits in the wing members are blocked, and to ensure that the struts can be readily removed from the template by grasping tab 694 which extends away from the front end 695 of the strut. Tab 694 may be provided in any of a variety of shapes, and the flat, curved tab shown in FIG. 57 is merely exemplary.

Struts 694 may be attached to the underside of the wing members in any manner desired, as long as the struts may later be removed at least partially from the wing members in order to unblock the slits 689 and 690 providing communication between adjacent apertures. For example, struts 691 may be lightly glued to the wing members, such that a firm pull on tab 694 will release the strut from the template. To facilitate such removal, tab 694 may be gripped with a mechanical grasping device, and then firmly pulled away from the template. Alternatively, a combination of alignable locking pins and apertures may be provided on lower surface 693 of the strut and the underside of the wing members.

Figure 60:
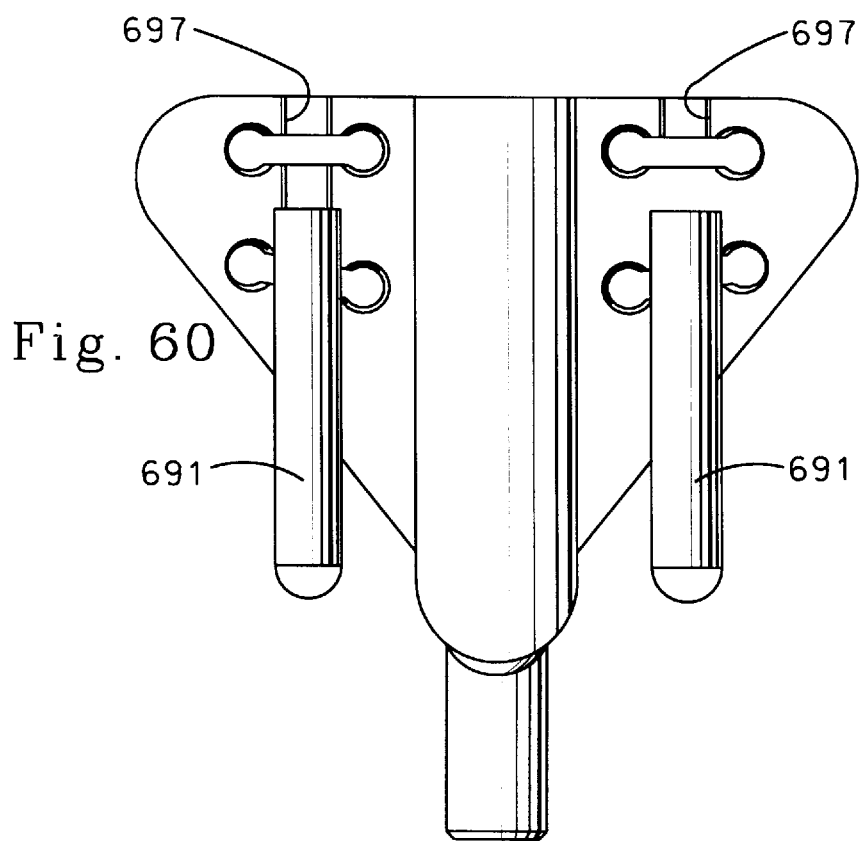
FIG. 60 is a top plan view of the template of FIG. 56, wherein said support struts have been partially detached from the template.
Figure 59:
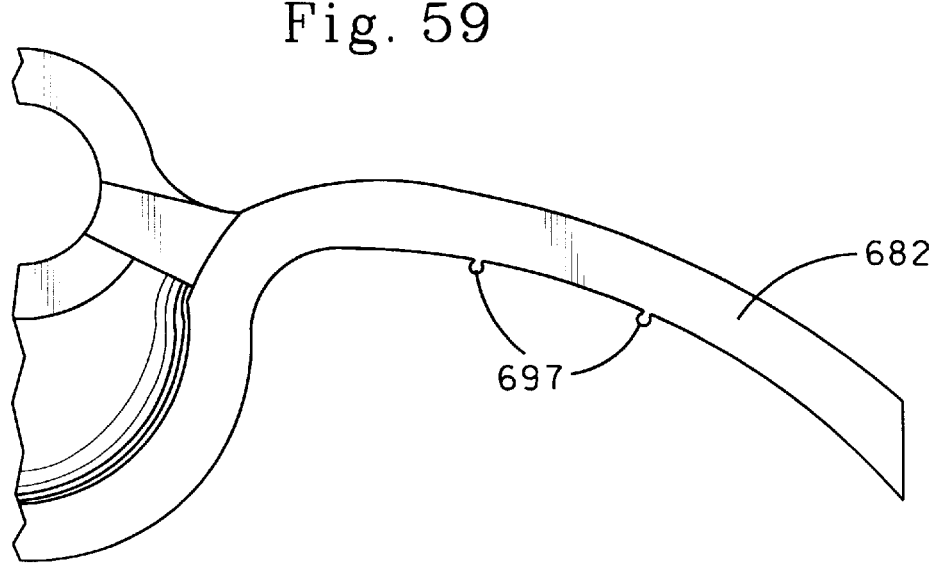
FIG. 59 is an end view of a portion of the template of FIG. 53.

It is preferred, however, that strut 691 be slid on and off of the template in order to provide for strut removal which is not encumbered by the suture extending around the curved upper surface 692 of the strut. This may be accomplished, for example, by providing at least one groove 696 along lower surface 693 of strut 691, and a corresponding tongue 697 along the underside of each wing member as shown in FIG. 59. Preferably, a pair of grooves 696 are provided along lower surface 693 of strut 691, and a pair of corresponding locking ridges or tongues 696. Tongues 696 are preferably their narrowest adjacent the underside of the wing member, and are their widest at the end furthest from the underside of the wing member. Any of a variety of shapes may be used, and the mushroom shape of FIG. 59 is by merely one example. Grooves 696 have a shape corresponding to that of tongues 697 such that strut 691 can be attached to the wing member by sliding the strut onto tongues 697. The male mushroom shape of the tongue and the corresponding female shape of the grooves ensure that the struts can only be attached or removed from the wing member by sliding the strut off of the front edge of the wing member. FIG. 60 depicts a pair of struts 691 which have been partially slid off of the underside of the wing members. Grooves 696 preferably extend along nearly entire length of the bottom surface of strut 691, and terminate at wall 698 adjacent tab 694. Wall 698 will act as a stop when strut 691 is slid onto the underside of the wing members as shown. Of course the positioning of the grooves and tongues may be reversed, such that the tongues are provided on the struts, and the grooves on the underside of each wing member.

Figure 61:
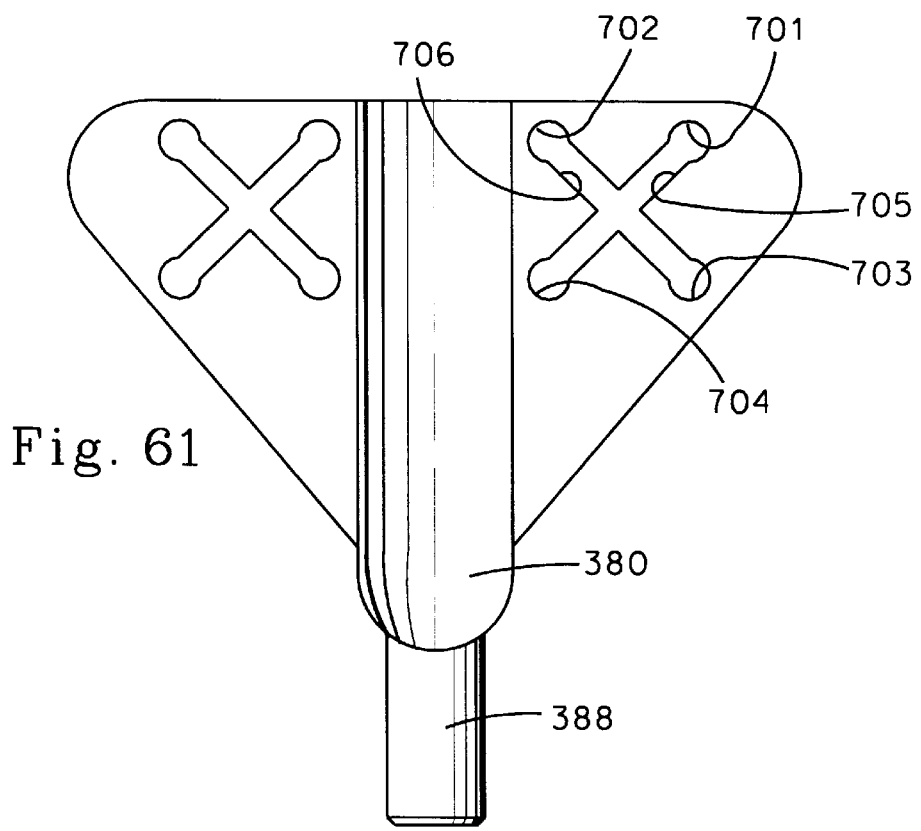
FIG. 61 is a top plan view of another embodiment of the template of the present invention.
Figure 62:
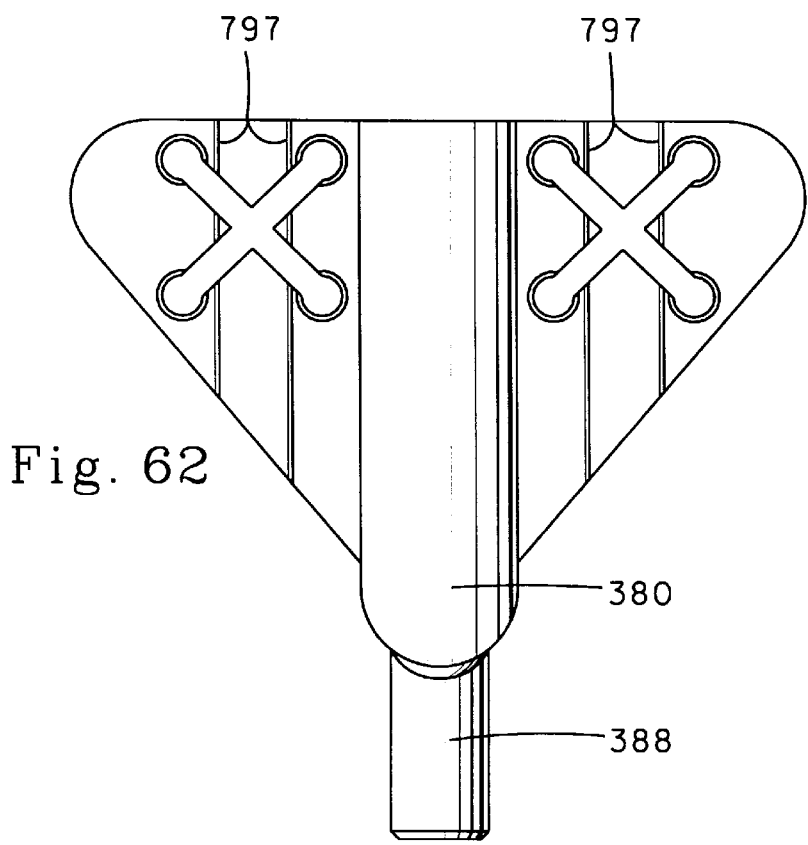
FIG. 62 is a bottom plan view of the template of FIG. 61.

FIGS. 61 and 62 depict yet another alternative embodiment of the template of the present invention. In this embodiment, the guides once again comprise four apertures in each wing member, and a slit provides communication between pairs of apertures. The slits, however, extend diagonally between apertures, and thus form the X-configuration shown. Thus, first aperture 701 is connected via slit 705 to fourth aperture 704, and second aperture 702 is connected via slit 706 to third aperture 703. The template of FIGS. 61 and 62 permits the surgeon to pass the sutures through the periurethral tissue in a figure-8 (or crossing) pattern.

Figure 78:
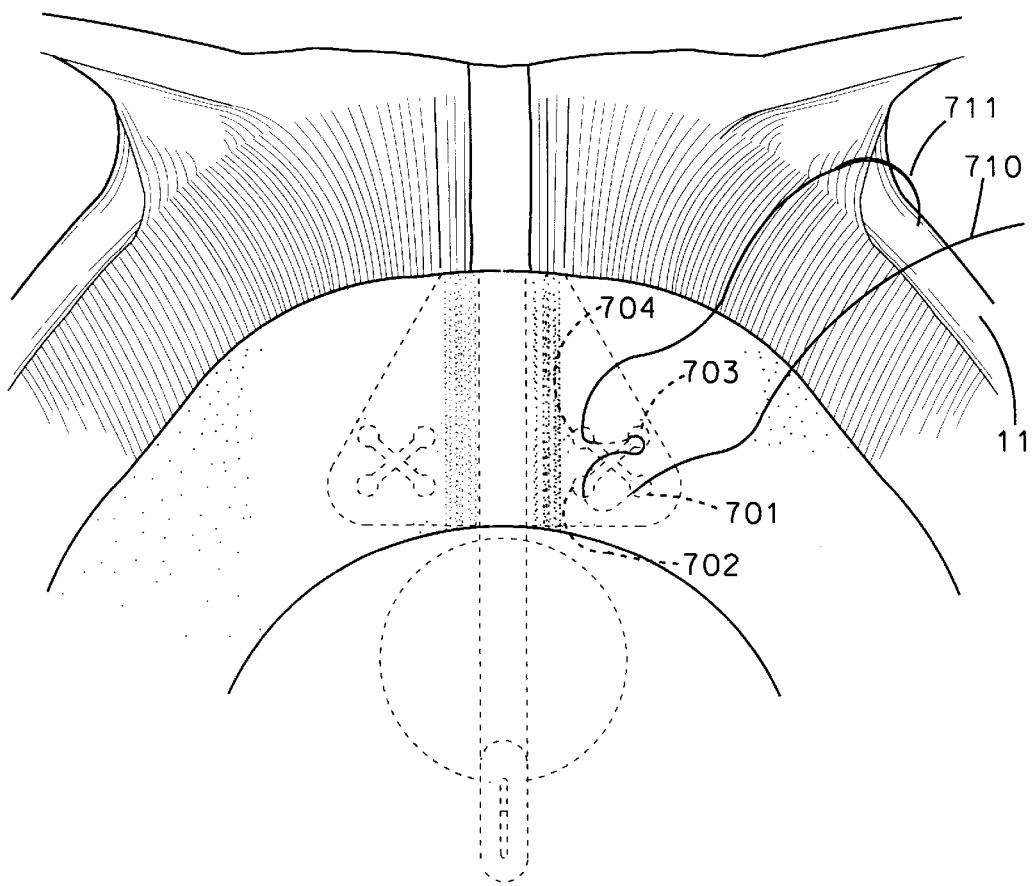
FIG. 78 is a perspective view of the space of Retzius showing the use of the template of FIG. 61.

FIG. 78 depicts one manner of using the template of FIGS. 61 and 62 during a Burch procedure wherein a single suture 710 is employed. Needle 711 is used to pass suture 710 through Cooper's ligament 11, and through the periurethral tissue into the vagina in the manner shown. Thus, suture 710 passes from the space of Retzius into the vagina through first aperture 701, passes back up into the space of Retzius through second aperture 702, returns into the vagina through third aperture 703, and finally returns back into the space of Retzius through fourth aperture 704. Needle 711 is cut from suture 410, and the two tails of suture 410 tied to each other. The process is repeated on the other side of the urethra, and the template is then removed by allowing the suture to be released through slits 705 and 706. It should also be noted that the template of FIGS. 61 and 62 may also be provided with grooves 797 for attaching the struts previously described thereto in order to provide blockage of the communication between apertures provided by slits 705 and 706, as desired.

If two sutures are employed on each side of the urethra during a Burch or needle suspension procedure using the template of FIGS. 61–62, the first suture will extend into the vagina through first and fourth apertures 701 and 704. The second suture will extend into the vagina through second and fourth apertures 702 and 703. When the template is removed after the sutures have been tied, the two sutures will cross over each other within the vagina.

It should be noted that while the above-described templates have been depicted in use during a Burch or urethropexy procedure employing bone anchors secured to the pubic bone, the templates of the present invention can be just as easily employed during a needle suspension (including that of Benderev). The procedure is similar to the Burch, with the primary difference being that the sutures or other fixation device are secured to the rectus fascia or the top of the pubic bone (in the case of Benderev). The sutures are also passed through the periurethral tissue into the vagina using a long needle device which is passed along the underside of the pubic bone. The templates of the present invention, however, are used in the same manner as described above to guide suture placement through the periurethral tissue, thereby simplifying these needle suspension procedures.

Figure 63:
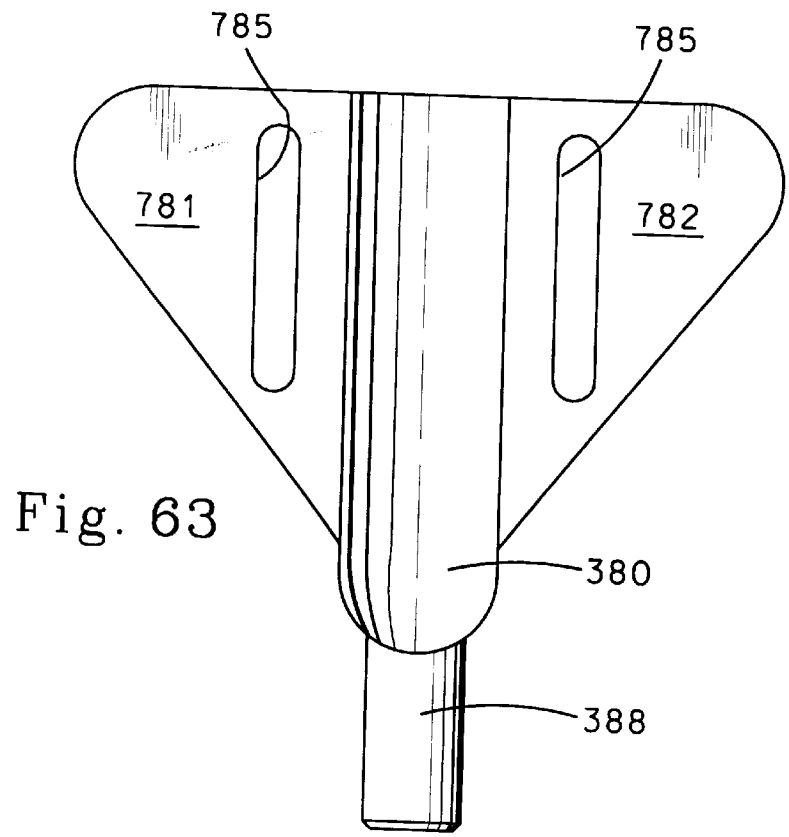
FIG. 63 is a top plan view of another embodiment of the template of the present invention.
Figure 64:
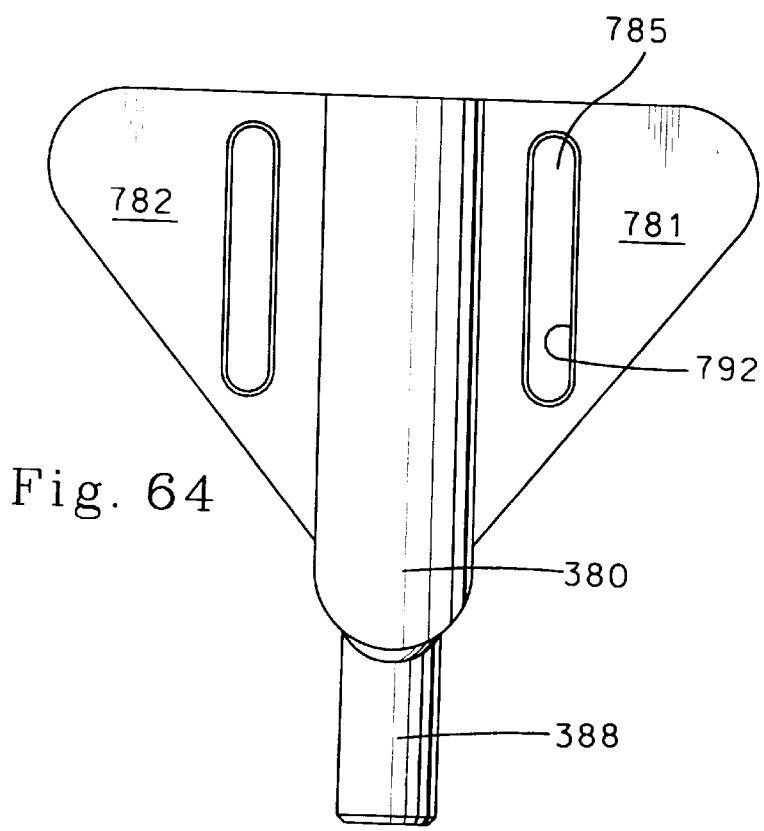
FIG. 64 is a bottom plan view of the template of FIG. 63.

FIGS. 63 and 64 depict yet another alternative embodiment for the template of the present invention. The body of FIGS. 63 and 64 is identical to that which has been previously described, and thus the body may comprise trough 380 and alignment member 388. A pair of guides, each comprising a slot 785, are disposed in a predetermined spacial relationship to the body portion. Preferably, a slot 785 is provided in each of wing members 781 and 782 as shown. Slots 785 should extend a considerable distance along each of the wing members, preferably substantially parallel to the longitudinal axis of trough 380. Slots 785 should each be positioned between about 1 and about 2 cm from the center line of the trough, and each preferably has a length of about 2 cm. Each slot 785 should also have a width of at least about 0.5 cm. Slots 785 should also be positioned a predetermined distance from distal end 791 of each wing member such that when the template of FIGS. 63 and 64 is positioned within the vagina in the manner previously described, each of slots 785 will extend to a point approximately 2 cm from the UVJ. In essence, the slots should be positioned on the wing members such that when the template is positioned in the vagina, the slot will extend from a point adjacent to the UVJ to at least the mid-point of the urethra. In addition, as shown in the bottom plan view of FIG. 64, the edge around each slot 785 on the underside of the wing members is preferably beveled slightly to facilitate insertion of a medical instrument therethrough.

Figure 65:
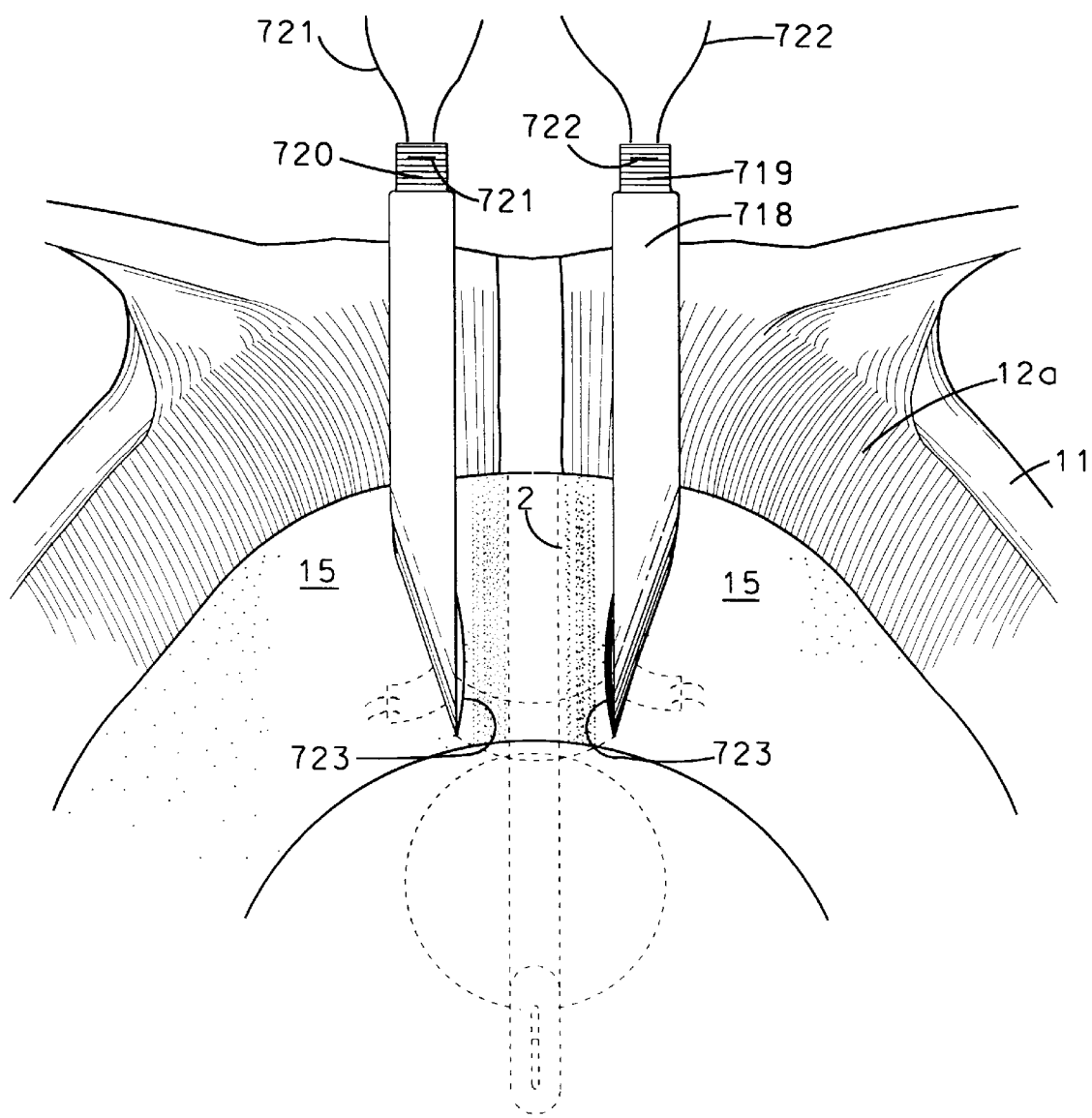
FIG. 65 is a perspective view of the space of Retzius, and illustrates the use of the template of FIGS. 63 and 64 in a sling procedure.

The template of FIGS. 63 and 64 is specifically designed for use in the urethral sling procedure (also known as a pubovaginal or suburethral sling procedure). In this sling procedure, the fixation device comprises a strip of flexible material (such as a polypropylene mesh or even a strip of fascia previously removed from the patient) which is positioned beneath the urethra, with the two ends of the sling connected relative to a structure within the patient's body. Thus, as shown in FIG. 65, a urethral sling 718 acts as a fixation device beneath urethra 2. First and second ends 719 and 720 of urethral sling 718 are secured relative to a structure within the patient's body, which in this case is the rectus fascia. Sutures 721 and 722 are passed through first and second ends 719 and 720 of the sling as shown, and are thereafter secured to the rectus fascia in the manner known to those skilled in the art. As is also well-known, ends 719 and 720 may also be secured by sutures or other known means to Cooper's ligament 11, or even periosteum of the pubic bone. As described below, Applicant has developed a new urethral sling which may even be riveted to the pubic bone itself.

In order for the sling to be positioned beneath urethra 2 and therefor act as a support, urethral sling 718 must pass through periurethral fascia 15. Thus, a pair of incisions 723 extending through the periurethral fascia 15 are provided on either side of urethra 2 adjacent to the UVJ, as shown. Preferably, these incisions extend only through the periurethral fascia 15, and not the vaginal mucosa, since urethral sling 718 will not be internalized as easily as sutures. In the standard sling procedure currently employed, a vaginal skin flap is created by peeling a portion of the vaginal mucosa away from the underlying periurethral fascia. The flap can later be reattached once the procedure is completed, thereby physically internalizing the sling. Once the flap of mucosa has been peeled away, the surgeon will then create the two incisions 723 which extend completely through the periurethral fascia into the space of Retzius using a scalpel or other cutting device. Preferably, incisions 723 extend from a point adjacent the UVJ to at least the mid-point of the urethra.

After the incisions in the periurethral fascia have been made, first end 719 of sling 718 is inserted through one of the incisions 723, and is then sewn to the rectus fascia. Second end 720 is then inserted from the vagina through the second incision 723 positioned on the opposite side of the urethra. Second end 720 is then brought into the space of Retzius, where it is likewise sewn to the rectus fascia. Alternatively, first and second ends 719 and 720 of sling 718 may be sewn to Cooper's ligament 11, or even to the periosteum 12a of the pubic bone.

One of the problems associated with the sling procedure described above is the proper positioning of the two incisions 723. The template of FIGS. 63 and 64, however, can readily overcome this problem, and can therefore direct placement of urethral sling 718 by guiding a cutting device to create incisions 695 in the proper location. After the vaginal mucosa has been peeled away, the template of FIGS. 63 and 64 is positioned in the vagina in the manner previously described, with the wing members positioned against the exposed suburethral fascia (as used herein, the term suburethral fascia is defined as the portion of the periurethral fascia located beneath the urethra). Once the template is in place, a hooked scalpel blade or other cutting device is positioned within slot 785 to create incisions 723. These incisions pass through the full thickness of the fascia, substantially parallel to the urethra and approximately 1.5 cm. lateral to the urethra. Slots 785 guide the movement of the blade, thereby providing precise location of the incisions and in turn preventing damage to structures and vasculature of the space of Retzius. The template may then be removed, and the sling procedure completed in the normal fashion.

FIGS. 74–77 depict Applicant's new urethral sling 718 which may be employed in the procedure described above. Urethral sling 718 essentially comprises a strip of flexible material. Sling 718 may have a length of between about 10 and about 20 cm, and a width in its central portion of between about 1.5 and about 2.5 cm. Ends 719 and 720 may be slightly narrower than the main body portion of the sling, and are also preferably slightly thicker. A series of ridges may also be provided on each of ends 719 and 720 to facilitate grasping of the ends by a mechanical grasping device such as a surgical clamp. Sling 718 may be made of any of the variety of polymeric materials, however polytetrafluoroethylene (PTFE) is preferred. PTFE is an extremely strong yet flexible material, which can also be molded into a variety of shapes. Thus, while the slings of the prior art generally comprise flat strips of flexible material, Applicant's urethral sling 718 is molded so as to better conform to the anatomy of the patient.

As shown in FIGS. 75 and 76, urethral sling 718 has a pair of 90° twists molded therein. Thus, sling 718 has a flat central portion 724, and right and left side portions 725 and 726, respectively. It should be pointed out, that FIG. 74 is a flat plan view of sling 718 wherein the pair of molded twists have been eliminated for purposes of clarity. Central portion 724 is configured so as to lie beneath the urethra as shown in FIG. 65. Side portions 725 and 726, on the other hand, are designed to extend upwardly through the incisions in the periurethral tissue as also shown in FIG. 65. Thus, in order to provide for the proper orientation, Applicant's sling 718 has a pair of twists 727 and 728 molded therein at the juncture between central portion 724 and right and left side portions 725 and 726, respectively. These 90° twist insure proper alignment of sling 718 during the procedure shown in FIG. 65. Thus, the plane defined by the surface of central portion 724 extends perpendicularly away from the plane defined by the surface of side portion 725 and 726.

During the surgical procedure of FIG. 65 when Applicant's sling 718 is employed, incisions 723 are created using the template in the manner described previously. A mechanical grasper is then inserted through one of the incisions 723 into the vagina, and grasp ridged end 719 of the sling. The grasper then pulls end 719 into the space of Retzius. A second mechanical grasper is then inserted into the other incision 723, and grasps second ridged end 720 and likewise pulls it into the space of Retzius. Both ends 719 and 720 of sling 718 are pulled upwardly until the desired elevation is achieved, and ends 719 and 720 are then sutured to the rectus fascia. Optionally, the surgeon may insert a pressure monitoring device into the urethra in order to determine the optimum degree of elevation provided by the sling. Suturing may be accomplished by passing a needle directly through each of ends 719 and 720 as shown in FIG. 65. The vaginal skin flap is then closed, thereby internalizing central portion 724 of sling 718.

Sling 718 may have a tendency to become displaced beneath the urethra, primarily because the PTFE material is non-scarring (i.e., scar tissue will not attach to the PTFE). Thus, Applicant's sling also has a pair of stabilizing tabs 729 and 730 extending therefrom. Preferably, stabilizing tabs 729 and 730 extend away from the surface of sling 718 adjacent twists 727 and 728 as shown. Stabilizing tabs 729 and 730 are preferably molded with sling 718, and may have a width which is slightly less than that of the sling itself. Thus, the stabilizing tabs preferably have a length and width of about 1 cm. After both ends 719 and 720 have been sutured to the rectus fascia, stabilizing tabs 729 and 730 are then sutured to the underside of the rectus fascia from within the vagina prior to closure of the vaginal skin flap. In this manner, movement of central portion of 724 of sling 718 in relation to the urethra will be prevented.

Although sling 718 can be sutured directly to the rectus fascia or even Coopers ligament or the periosteum of the pubic bone, Applicant's sling 718 may also be riveted to the pubic bone itself. Any of a variety of bone anchors may be employed for this purpose. While the anchor may be merely driven through the sling material into the pubic bone, such techniques are generally not preferred since the sling may be damaged and thereby weakened. Thus, Applicant's sling 718 may have a plurality of pockets 731 which extend away from each of side portions 725 and 726 as shown in FIG. 77. Pockets 731 should extend away from the surface of side portions 725 and 726 towards the pubic bone when sling 718 is positioned within the patient at the desired orientation. The interior of pockets 731 is then accessible from the opposite surface of the sides portions. Pockets 731 are configured such that an anchor may be inserted therein, and the anchor and pocket 731 combination then secured within a corresponding bore in the pubic bone for attachment thereto. Preferably, a plurality of pockets 731 are provided in each side portion 725 and 726 as shown, such that either a plurality of anchors may be used to secure sling 718, or the surgeon may select whichever pockets 731 are appropriate to provide the desired urethral elevation.

In a preferred method of using the sling of the present invention, ends 719 and 720 are pulled into the space of Retzius by means of mechanical graspers. The surgeon then manipulates the mechanical graspers so as to position sling 718 in a manner which will provide the desired elevation. The surgeon next determines the location for the bores to be provided in the pubic bone for the riveting of sling 718 thereto. This may be accomplished by merely comparing the locations of pockets 731 with respect to the pubic bone. The bores are then created in the pubic bone in the manner described previously. A pocket 731 is next aligned with its corresponding bore in the pubic bone, and an anchor is then driven into the interior of pocket 731 and into the bore in the pubic bone. In this manner, sling 718 is riveted to the pubic bone. While any of a variety of bone anchors may be employed for this purpose, it is presently preferred that the bone anchors manufactured by Innovasive Devices, Inc. of Hopkinton, Mass. or Lee Medical Technologies, Inc. of Shelton, Conn. be employed. Both of these anchors have an expandable portion which expands outwardly after the anchor has passed into the bore in the pubic bone. This, pockets 731 are preferably mushroomed shape and have a flat inner surface 732 against which the expandable portion of the bone anchors will bear. The distance 733 between the surface of the end portion of the sling and flat wall 732 of pockets 731, therefore, preferably corresponds to the thickness of the periosteum and cortical bone through which the bore has been created. Alternatively, although the Mitek™ anchors may be employed, these are not preferred since the sharp barbs of the anchor may damage the sling material. Pockets 731 may even be replaced by a simple aperture and the sling then riveted to the pubic bone by means of a bone rivet such as that shown in FIG. 2.2 of U.S. Pat. No. 5,268,001 to Innovasive Devices, Inc.

As indicated previously, the PTFE material from which the sling is made is non-scarring. It is preferred, however, that scar tissue form about the fixation devices of the present invention in order to enhance the attachment provided by these surgical methods. Thus, sling 718 may also be provided with a plurality of perforations through its thickness. These perforations will allow ingrowing of scar tissue in order to further secure the sling of the present invention in place. In addition, each side of the template (or more preferably, each side of ends 719 and 720), may be color coded or provided with other visible indicia such as diagonal bars 734 in order to indicate to the surgeon the preferred orientation of sling 718 such that pockets 731 will extend towards the pubic bone as desired.

Many surgeons would rather not pass sutures or other fixation devices into the vagina. All of the procedures described above can be accomplished, however, by merely passing the suture or fixation devise through a portion of the periurethral tissue without entering the vagina. For example, in a Burch procedure, the surgeon may merely pass the needle through a bite of periurethral fascia without actually passing the needle into the vagina itself. Several bites of periurethral fascia may be taken, and if done properly, the suspension of the periurethral fascia from Cooper's ligament may be successful. Many needle suspensions also take only a bite of tissue, rather than entering the vagina. In all of these procedures, however, the surgeon faces both the problem of proper location of the sutures, as well as the problem of ensuring that an adequate bite of tissue is taken. The surgeon will often insert a finger into the vagina in order to displace the periurethral fascia upwardly, thereby providing visualization from within the space of Retzius. This procedure can be difficult, however, in that precise location is not guaranteed, and the surgeon may either inadvertently stab his or her finger with the needle, or fail to take an adequate bite of tissue due, in part, to the surgeon's desire to avoid puncturing his or her own finger. While the device of the Hasson patent previously described offers a solution to the problem of inadvertent stabbing of the surgeon's or assistant's finger, it does not address the issue of precise suture placement. The templates of FIGS. 66–70, however, solve this problem.

Figure 67:
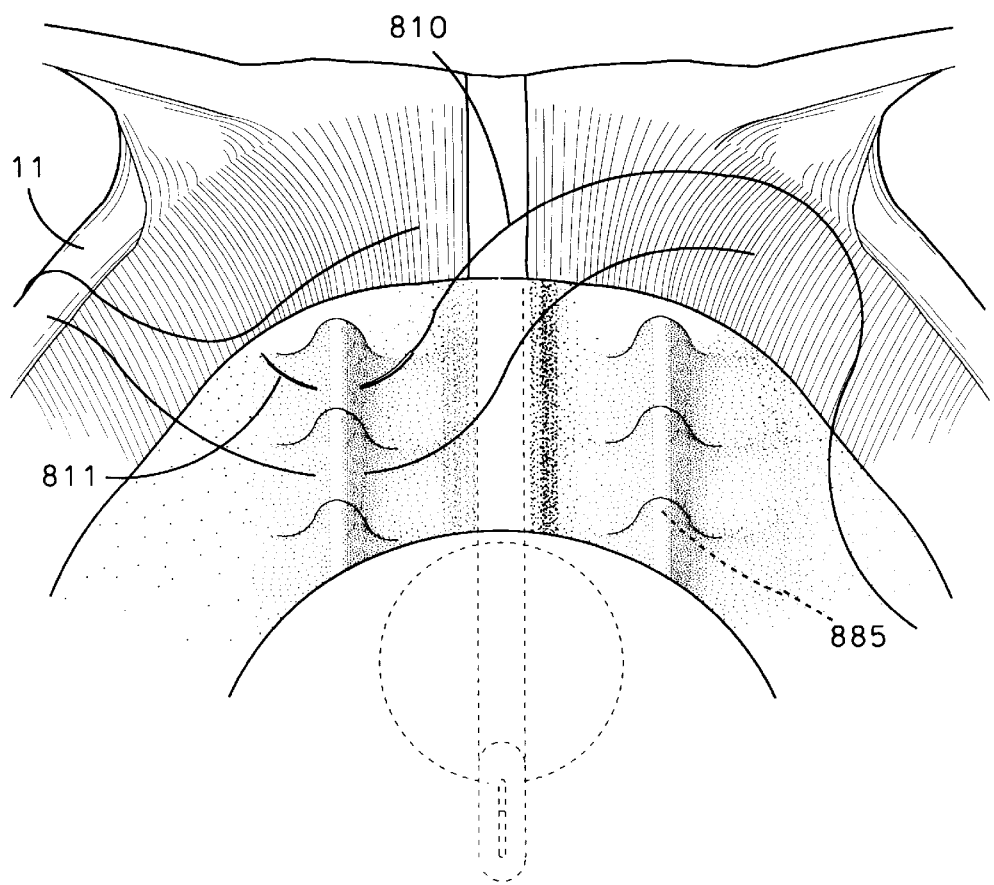
FIG. 67 is a perspective view of the space of Retzius, and illustrates the use of the template of FIG. 66.

Once again the template of FIG. 66 has body portion similar to that previously described, comprising trough 380 and alignment member 388. Instead of apertures, however, each wing member has at least one, and preferably at least three protrusions 885. The protrusions on each wing member are preferably spaced from and aligned with each other, preferably along a line which is substantially parallel to the longitudinal access of trough 880. While these protrusions can take any of a variety of shapes, it is preferred that they be conical, having a base diameter of about 0.2 to about 0.4 cm, and a height of about 1 cm. It should be noted, of course, that like all of the dimensions indicated herein, these are merely exemplary of one preferred embodiment. As shown in FIG. 67, when the template of FIG. 66 is positioned within the vagina in the manner described previously, protrusions 885 will displace a predetermined region of a the periurethral fascia upwardly into the space of Retzius. This displacement will be visible from within the space of Retzius, either by normal operative vision in a full open procedure, or through a laparoscope or other viewing device. In this manner, the protrusions will direct placement of a fixation device through the periurethral tissue approximately 1.5 to 2 cm from the centerline of the urethra. It should also be noted that the wing members in the template of FIG. 66 are swept distally (i.e., distal edge not perpendicular to the longitudinal axis of trough 380) to allow the tissue tented between the two most distal protrusions to be at the UVJ.

In FIG. 67, a Burch procedure is shown, wherein a curved needle 811 having a suture 810 is passed between a pair of adjacent protrusions 885 as shown. Since protrusions 885 are relatively closely spaced, the tissue between each protrusion 885 will also be displaced upwardly, although not to the same extent as the tissue directly contacted by each protrusion. Thus, not only do the protrusions provide visualization of the proper location of the sutures, the region between adjacent protrusions 885 will also be tented upwardly, thereby allowing the surgeon to pass the needle through this displaced region. This ensures that an adequate bite of tissue is taken. The conical nature of the protrusions will also act to guide the needle into the space between adjacent protrusions.

After needle 811 and suture 810 have been threaded through the region between a first pair of adjacent protrusions as shown in FIG. 67, it may then be passed through Cooper's ligament, the needle removed, and the tails of the suture tied to each other. A second suture may be similarly passed between another pair of adjacent protrusions 885 and secured to Cooper's ligament 11. Alternatively, a single suture may take multiple bites between adjacent protrusions. The procedure is then repeated on the opposite side of the urethra, thereby elevating the UVJ to the desired angle.

In order to insure that protrusions 885 provide sufficient displacement of the periurethral tissue so as to be visible from within the space of Retzius, the surgeon or their assistant may need to press the template upwardly from within the vagina. Alternatively, a portion of the template body may be expandable such that after the template is positioned within the patient's vagina in the manner previously described, this expandable portion may be expanded so as to urge the expandable portion against a portion of the interior wall of the vagina. This will in turn force protrusions 885 upwardly against the vaginal mucosa adjacent the urethra, thereby providing for increased displacement of the periurethral tissue. This increased displacement of the periurethral tissue will improve visibility of the displacement from within the space of Retzius.

Figure 69:
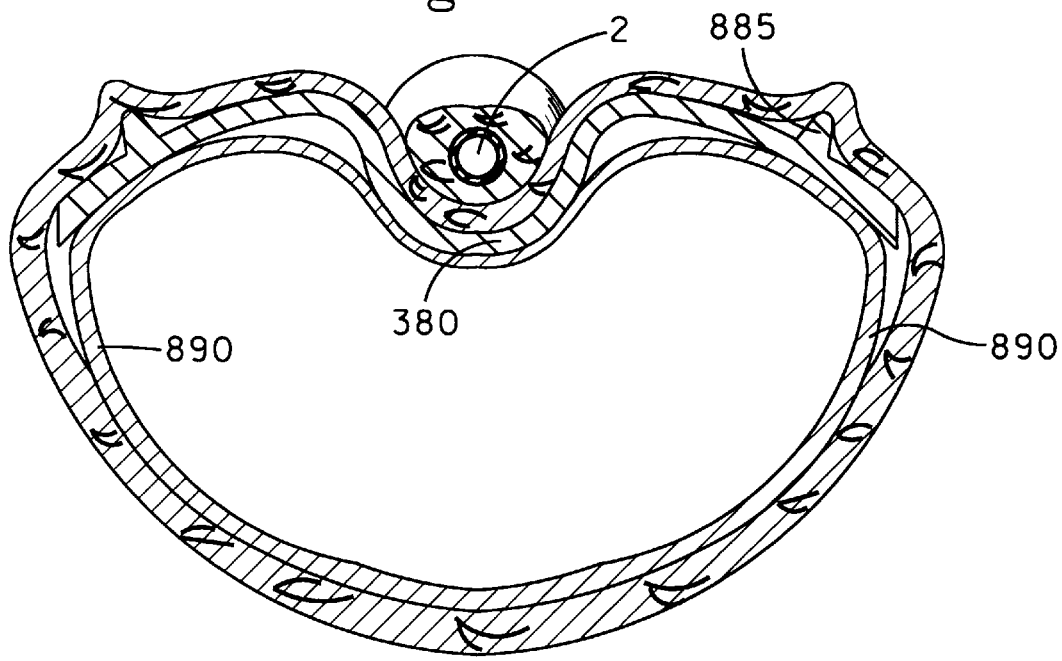
FIG. 69 is a cross-sectional view of a vagina with the template of FIG. 67 positioned therein.

As shown in FIG. 66, 68 and 69, the expandable portion of the template body may comprise a balloon 890 which is secured to the underside of trough 880. Balloon 890 may be of any of a variety of shapes and sizes, however, in the preferred embodiment balloon 890 is cylindrical in order to better match the shape of the vaginal cavity when inflated. A port 891 is provided at one end of the balloon, and provides communication to the interior of balloon 890. Balloon 890 may be inflated with any of a variety of fluids, including both gases and liquids. A simple syringe or hand-held pump may be inserted through port 891, and used to inflate balloon 890 with air. Alternatively, port 891 may be connected to any of a variety of fluid sources, such as a compressed air source. It is preferred, that a hand-operated pump be used. In addition, a pop-off valve may be provided in order to prevent overinflation of the balloon.

As best shown in the cross-sectional view of FIG. 69, inflated balloon 890 attached to the underside of trough 880 will fill the vaginal cavity beneath the template, thereby urging protrusions 885 upwardly against the periurethral tissue. The upward displacement of the periurethral tissue will then be readily visible from within the space of Retzius. It is preferred that the balloon be filled with between about 10 and 200 cc of fluid, thereby providing sufficient upward displacement of tissue without damaging the vaginal cavity or the support structures for the vaginal cavity. Balloon 890 may be attached to trough 880 by any of a variety of means, including a simple adhesive strip 892. After the surgical procedure has been completed, balloon 890 is deflated, and the template removed from the vaginal cavity.

Figure 70:
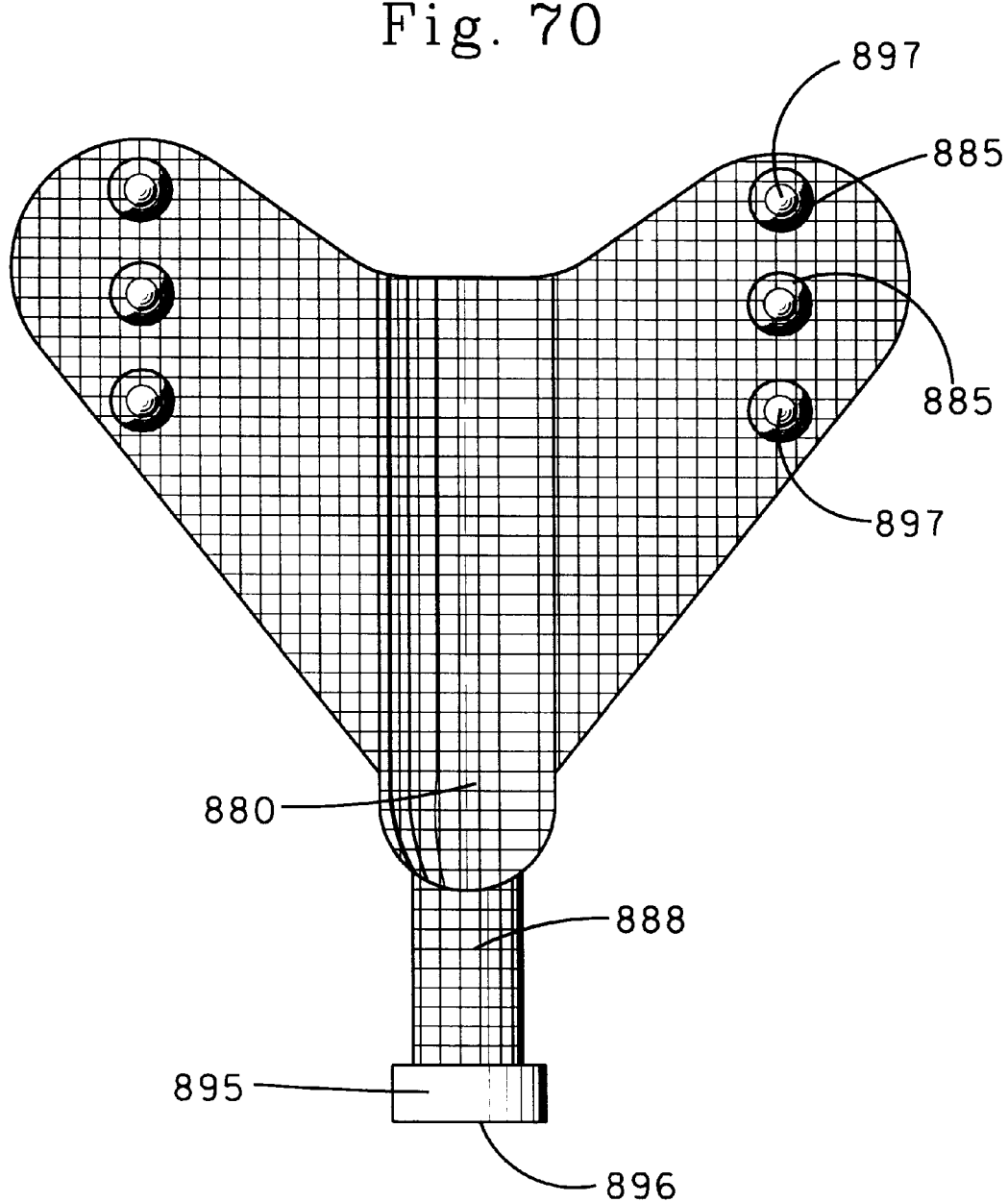
FIG. 70 is a top plan view of another embodiment of the template of the present invention.

FIG. 70 depicts yet another modification to the template of FIG. 66 and may be used with or without the balloon structure previously described. The template of FIG. 70 is identical to that of FIG. 66, with or without balloon 890, however a collar 895 is provided at the end of alignment member 888. Collar 895 has a diameter slightly greater than alignment member 888, thereby providing end wall 896 of collar 895 which is concentric to the end of alignment member 888. The entire template of FIG. 70 should be singularly molded from a highly translucent polymer through which light may be readily transmitted. A preferred polymer is polycarbonate, as it transmits light without a corresponding increase in temperature. Alternatively, the template may even be impregnated with optical fibers (i.e., fiber optics) through which light may be transmitted to the desired location.

The entire template of FIG. 70, other than the tips 897 of protrusions 885 and collar 895, are opaque. Preferably, only tips 897 and collar 895 are translucent, with the remainder of the template being completely black. This may be accomplished, for example, by applying a black coating to the template. A light source, preferably of a fiber optic variety, is attached to collar 895, and projects light through end 896 thereof. Fiber optics positioned within the template itself may facilitate transmission of light to the tips 897 of the protrusions. Because of the opacity of the template, this light is transmitted through the body and wing members of the template, and will only escape through tips 897 of protrusions 885. When the template of FIG. 70 is positioned within the vagina in the manner shown in FIG. 67, preferably using balloon 890, the light emitted from tips 897 of protrusions 885 will pass through the periurethral tissue displaced by tips 897, thereby transilluminating this region and guiding placement of the fixation device between the protrusions.

As an alternative to transmitting light through the entire template body, protrusions 885 may also be hollow with the interior thereof accessible from the underside of the wing members. A light source (preferably fiber optic) may then be directed into the interior of the protrusions, such that the light therefrom will be projected out of translucent tip 897 of the protrusion in order to transilluminate the periurethral tissue in the same manner is above. It should also be pointed out that light of any wavelength may be employed for all of the transillumination procedures described herein.

Figure 71:
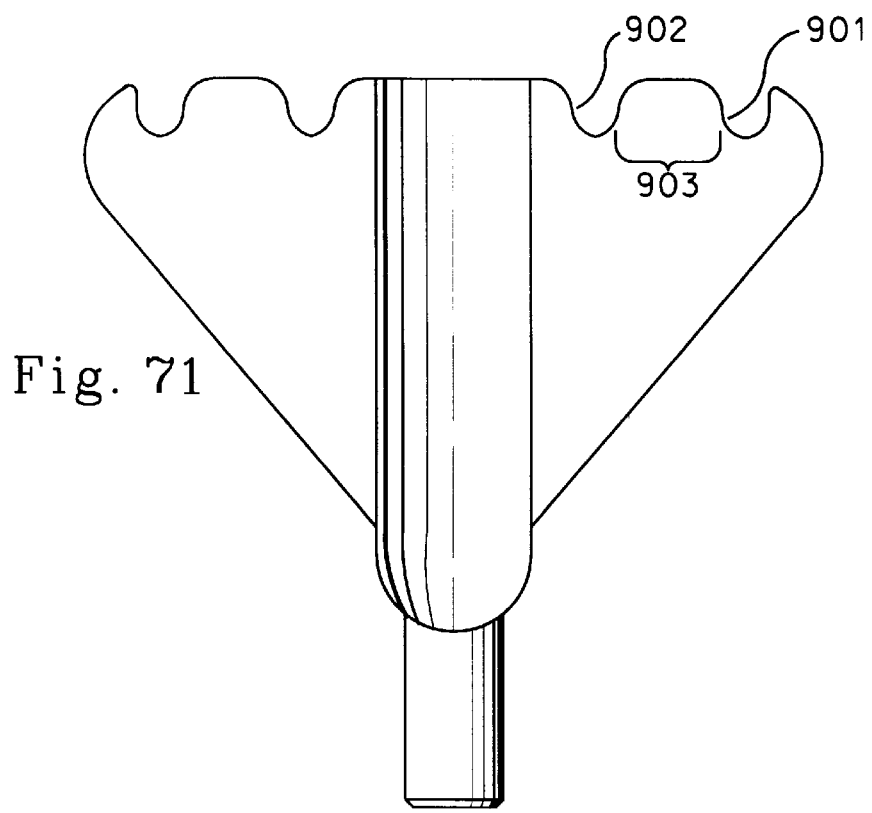
FIG. 71 is a top plan view of another embodiment of the template of the present invention.
Figure 72:
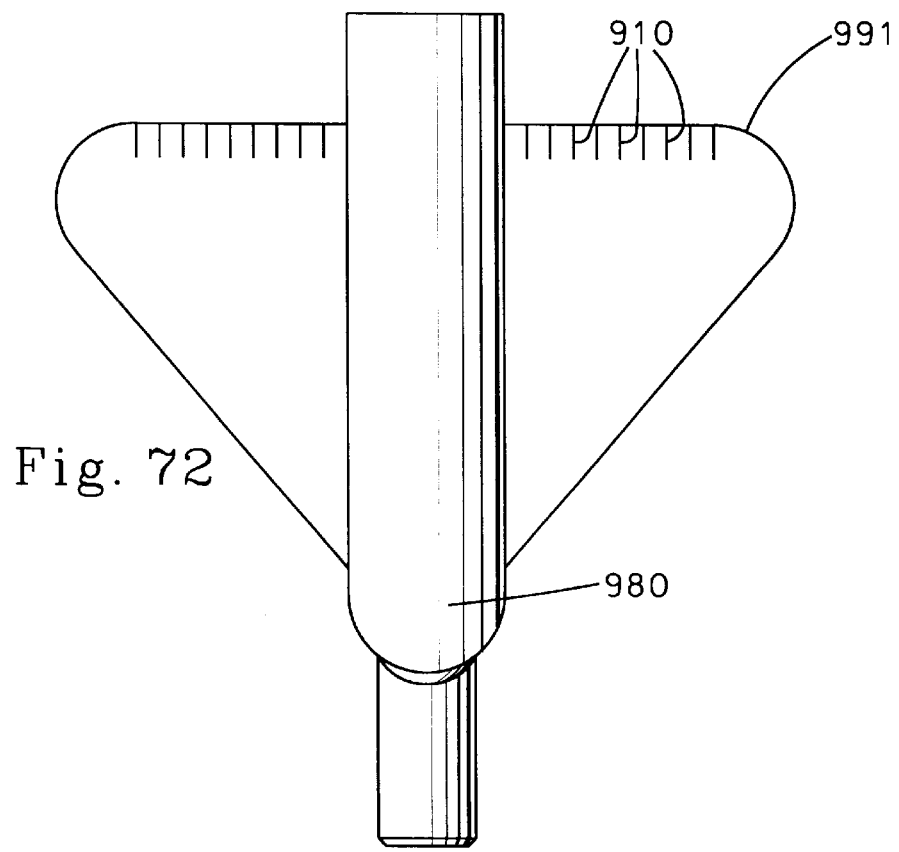
FIG. 72 is a bottom plan view of another embodiment of the template of the present invention.

Finally, FIGS. 71 and 72 depict two relatively simple alternative template designs. In the top plan view of FIG. 71, the guides are provided in the form of a pair of notches 901 and 902 on each wing member. This template can be used in a manner similar to the template of FIGS. 13–21, however the template of FIG. 71 will permit tying in the space of Retzius. The suture retriever may be passed through notches 901 and 902 in the same manner as if the notches were apertures, or alternatively a suture may be passed from the space of Retzius, through the periurethral tissue and into the vagina through notch 901, and then back into the space of Retzius through notch 902. The suture tails may then be tied in the space of Retzius, and the template removed by merely sliding the portion of the suture within the vagina off of the region 903 of the underside of the template between notches 901 and 902.

The guides on the template of FIG. 72 comprise a plurality of graduations 910 on the underside of each wing member. These graduations may comprise simple lines as shown, and may be facilitate proper is designated to facilitate proper placement of the fixation device. The graduations are provided on the underside of the wing member so that they will be visible from within the vagina. In the embodiment of FIG. 72, the wing members have also been shortened such that the distal end 991 of each wing member does not extend to the end of trough 980 as in the previously-described embodiments. In this manner, the graduations may, for example, be used to direct insertion of the suture retriever of the present invention at a predetermined location immediately adjacent distal end 991. The template of FIG. 72 will also thereby permit suture tying in the space of Retzius when desired, since the sutures will at no time pass through any portion of the template.

The foregoing description of preferred embodiments is by no means exhaustive of the variations of the present invention which are possible, and has thus been presented only for purposes of illustration and description. These modifications and variations will be apparent to those skilled in the art in light of the teachings of the foregoing description, and these modifications and variations are well within the scope of the present invention. For example, the templates of the present invention may be used in any of a variety of gynecological procedures. In addition, the dimensions for the various components of the template are merely exemplary, and modifications to these dimensions may be made in order to accommodate the preferences of various surgeons. Thus, it is intended that the scope of the present invention be defined by the claims appended hereto, and not by the specific embodiments shown in the drawings.

What I claim is:

1. A template for guiding the placement of a fixation device during a surgical procedure, said template comprising:
   (a) a body portion; and
   (b) at least one guide disposed in a predetermined spacial relationship to said body portion;
said template adapted to be aligned at least partially within the vagina of a patient such that said guide may be employed to direct the placement of a fixation device or other medical instrument through at least a portion of the tissue adjacent the vagina.

2. The template of claim 1, wherein the template is configured such that when said template is aligned within the vagina, said at least one guide may be employed to direct placement of a fixation device or other medical instrument at least a portion of the tissue adjacent the vagina in a predetermined 5 relationship to a landmark within the patient's body.

3. The template of claim 2, wherein said landmark comprises the UVJ.

4. The template of claim 2, wherein said template is configured such that a portion of the anatomical structure of a patient's vaginal region directs alignment of the template at least partially within the patient's vagina such that said at least one guide may be employed to direct placement of a fixation device or other medical instrument through at least a portion of the tissue adjacent the vagina in a predetermined relationship to a landmark within the patient's body.

5. The template of claim 1, further comprising at least one wing member, and wherein said at least one guide is provided on said wing member.

6. The template of claim 1, wherein said template further comprises an elongate member which may be inserted into a patient's urethra.

7. The template of claim 5, wherein said template further comprises an elongate member which may inserted into a patient's urethra.

8. The template of claim 6, wherein said elongate member comprises a catheter secured to said body.

9. The template of claim 7, wherein said elongate member comprises a catheter secured to said body.

10. The template of claim 1, wherein said body comprises a trough of arcuate cross-section.

11. The template of claim 2, wherein said body comprises a trough of arcuate cross-section, and wherein said wing member extends away from one side of said trough.

12. The template of claim 11, wherein said body comprises a trough of arcuate cross-section, and wherein said trough is configured such that a patient's urethra may be positioned within said trough, thereby positioning said wing member adjacent the urethra.

13. The template of claim 10, wherein said body further comprises an alignment member, and wherein said template has an elongate member secured to said alignment member, wherein said elongate member may be inserted into a patient's urethra, wherein said trough and said alignment member each have a longitudinal axis, and wherein the longitudinal axis of said alignment member is parallel to the longitudinal axis of said trough.

14. The template of claim 13, wherein the longitudinal axis of said alignment member is parallel to and above the longitudinal axis of said trough.

15. The template of claim 1, wherein said template has a pair of wing members, each of said wing members having at least one guide, and wherein said template is alignable within the vagina of a patient such that said one of said wing members is positioned adjacent either side of the urethra with said guides positioned such that they may be employed to direct the placement of a fixation device through the tissue adjacent the urethra.

16. The template of claim 15 wherein said body comprises a trough of arcuate cross-section, and wherein said wing members extend away from opposite sides of said trough.

17. The template of claim 1, wherein said at least one guide is chosen from the group consisting of: an aperture, a slot, a notch, a protrusion and a visible indicia.

18. The template of claim 5 wherein said at least one guide is chosen from the group consisting of: an aperture, a slot, a notch, a protrusion and a visible indicia.

19. The template of claim 6 wherein said at least one guide is chosen from the group consisting of: an aperture, a slot, a notch, a protrusion and a visible indicia.

20. The template of claim 17, wherein said guide comprises a light source.

21. The template of claim 20, wherein said template is configured to be alignable within the vagina of a patient such that a beam of light may be projected from said light source through a predetermined region of the periurethral tissue, thereby transilluminating said predetermined region of the periurethral tissue.

22. The template of claim 21, wherein said template further comprises at least one wing member, said wing member having a topside and an underside, said template configured to be alignable within the vagina such that the topside of said wing member will be positioned against the vaginal mucosa adjacent the urethra, and wherein a beam of light may be projected from said light source, away from the topside of said wing member, and through the periurethral tissue adjacent the topside of the wing member.

23. The template of claim 22, wherein said at least one guide further comprises a protrusion extending away from the topside of said wing member, and wherein said light source is provided on said protrusion.

24. The template of claim 20, wherein said light source comprises a translucent region through which a beam of light may be projected.

25. The template of claim 17, wherein said at least one guide comprises a protrusion, wherein said template is configured to be alignable within the vagina of a patient such that said protrusion will displace a predetermined region of the periurethral tissue of the patient.

26. The template of claim 25, wherein a plurality of said protrusions are provided, said protrusions positioned adjacent to one another such that the region between said protrusions can be visualized from within the abdominal cavity of the patient by observation of the regions of the periurethral tissue displaced by adjacent protrusions.

27. The template of claim 26, further comprising at least one wing member, and wherein said plurality of protrusions are provided on said wing member.

28. The template of claim 27, wherein said wing member has a topside and an underside, said template configured to be alignable within the vagina such that the topside of said wing member will be positioned against the vaginal mucosa adjacent the urethra, and wherein said protrusions extend away from the topside of said wing member.

29. The template of claim 17, wherein said at least one guide member comprises a slot sized so as to permit a cutting tool to be inserted therethrough in order to create an incision in the periurethral tissue of a patient during a continence procedure.

30. The template of claim 18, wherein said at least one guide member comprises a slot sized so as to permit a cutting tool to be inserted therethrough in order to create an incision in the periurethral tissue of a patient during a continence procedure.

31. The template of claim 30, wherein said slot is positioned on said wing member such that said template may be aligned within the vagina of a patient with said slot extending substantially parallel to the patient's urethra.

32. The template of claim 29, further comprising an elongate member which may be inserted into a patient's urethra, said alignment member having a longitudinal axis, and wherein said slot extends substantially parallel to the longitudinal axis of said alignment member.

33. The template of claim 30, further comprising a pair of wing members, wherein a slot is provided on each of said wing members, and wherein said wing members and said slots are configured such that when said template is aligned within the vagina of a patient, a cutting tool may be inserted through said slots in order to create an incision in the periurethral tissue adjacent either side of the patient's urethra.

34. The template of claim 17, wherein said at least one guide member comprises an aperture through which a fixation device may be passed during a urethropexy procedure.

35. The template of claim 18, wherein said at least one guide member comprises an aperture through which a fixation device may be passed during a urethropexy procedure.

36. The template of claim 34, wherein said template has at least two of said apertures.

37. The template of claim 36, wherein two of said apertures are connected to one another by a slit.

38. The template of claim 35, wherein said template has at least two of said apertures provided on said wing member, and wherein two of said apertures are connected to one another by a slit.

39. The template of claim 38, further comprising a pair of wing members, and wherein each wing member has at least two of said apertures connected to one another by a slit.

40. The template of claim 1, further comprising a support strut, said strut configured such that a fixation device may be secured about said strut during an urethropexy procedure.

41. The template of claim 40, wherein said support strut is removable, and wherein a fixation device secured about said strut during an urethropexy procedure can be released therefrom when said strut is removed from said template.

42. The template of claim 40, wherein said template further comprises at least one wing member, and wherein said support strut is positioned on said wing member.

43. The template of claim 42, wherein a pair of said guides are provided on said wing member, and wherein said guides comprise apertures.

44. The template of claim 43, wherein said apertures are connected to one another by a slit, and wherein said support strut is positioned atop at least a portion of said slit, thereby blocking communication between said apertures.

45. The template of claim 44, wherein said support strut is removable.

46. The template of claim 44, wherein said wing member has a topside and an underside, wherein said template is configured to be alignable within the vagina of a patient such that the topside of said wing member will be positioned against the vaginal mucosa adjacent the urethra, and wherein said support strut extends away from the underside of said wing member.

47. The template of claim 1, wherein at least a portion of said template is expandable.

48. The template of claim 47, wherein said template is configured such that at least the expandable portion of said template may be inserted into a patient's vagina in an at least partially unexpanded condition, and thereafter expanded so as to urge said expandable portion against the interior wall of the vagina and to urge said at least one guide against a predetermined region of the periurethral tissue.

49. The template of claim 48, wherein said expandable portion is inflatable.

50. The template of claim 49, wherein expandable portion comprises a balloon which may be inflated with a fluid.

51. The template of claim 50, wherein said guide comprises a protrusion, and wherein said protrusion is configured such that said protrusion will displace a predetermined region of the periurethral tissue of the patient when the expandable portion of said template is expanded within the vagina of a patient, and wherein the displacement will be visible within the abdominal cavity of the patient.

52. The template of claim 51, wherein said template has a plurality of said protrusions.

53. A template for guiding the placement of a fixation device during a surgical procedure to correct incontinence, said template comprising:
(a) a body portion;
(b) at least one guide disposed in a predetermined spacial relationship to said body;
said template adapted to be aligned at least partially within the vagina of a patient such that said guide may be employed to direct the placement of a fixation device through the periurethral tissue at a predetermined location.

54. The template of claim 53, wherein said template is configured such that when said template is aligned at least partially within a vagina of a patient, said guide will be positioned adjacent the periurethral tissue at a predetermined location.

55. The template of claim 53, wherein said template is configured such that alignment of the template at least partially within a vagina of a patient is directed by a portion of the anatomical structure of the patient's vaginal region.

56. The template of claim 55, wherein said template is configured such that alignment of the template at least partially within a vagina of a patient is directed by the patient's urethra.

57. The template of claim 56, wherein said template further has an elongate member which may be positioned within the urethra of a patient so as to align the template at least partially within the patient's vagina with said guide positioned adjacent the periurethral tissue at a predetermined location.

58. The template of claim 56, wherein the body of said template comprises an arcuate trough, said trough configured such that a patient's urethra and the periurethral tissue beneath the urethra may be positioned within said trough so as to align the template at least partially within the patient's vagina with said guide positioned adjacent the periurethral tissue at a predetermined location.

59. The template of claim 56, wherein said guide is chosen from the group consisting of: an aperture, a slot, a notch, a protrusion and a visible indicia.

60. The template of claim 57, wherein said template further comprises a wing member, and wherein said guide is positioned on said wing member.

61. A surgical method of connecting at least a portion of the tissue adjacent a patient's vagina relative to a structure within the patient's body, comprising:
(a) providing a vaginal template, said template having at least one guide for ensuring proper positioning of a fixation device;
(b) aligning at least a portion of said template within the vagina of a patient; and
(c) connecting a portion of the tissue adjacent a patient's vagina relative to a structure within the patient's body with a fixation device by:
connecting one portion of said fixation device relative to said structure within the patient's body; and
passing another portion of said fixation device through at least a portion of the tissue adjacent the patient's vagina, using said guide to direct placement of the fixation device through the tissue.

62. The surgical method of claim 61, wherein at least a portion of said template is aligned within the patient's vagina such that said at least one guide is positioned in a predetermined relationship to an anatomical landmark within the patient's body.

63. The surgical method of claim 61, wherein said template is configured such that alignment of said template is directed by the patient's urethra.

64. The surgical method of claim 61, wherein said fixation device is chosen from the group consisting of: a filamentatious member, and an urethral sling.

65. The surgical method of claim 64, wherein said fixation device comprises a filamentatious member, and wherein said filamentatious member is chosen from the group consisting of: a suture, a thread and a wire.

66. The surgical method of claim 61, wherein said structure within the patient's body is chosen from the group consisting of: the pubic bone, the periosteum of the pubic bone, the pubic symphysis, Cooper's ligament, and the rectus fascia.

67. The surgical method of claim 61, wherein said fixation device is connected relative to said structure by suturing, and wherein said structure is chosen from the group consisting of: the periosteum of the pubic bone, the pubic symphysis, Cooper's ligament, and the rectus fascia.

68. The surgical method of claim 61, wherein said fixation device is connected relative to the pubic bone by connecting said fixation device to an anchor secured to the pubic bone.

69. The surgical method of claim 61, wherein a portion of said fixation device is placed through the periurethral tissue without entering the patient's vagina.

70. The surgical method of claim 61, wherein said template comprises a body portion, and said at least one guide is disposed in a predetermined spacial relationship to said body portion.

71. The surgical method of claim 70, wherein said at least one guide is chosen from the group consisting of: an aperture, a slot, a notch, and a visible indicia.

72. The surgical method of claim 71, wherein said at least one guide comprises an aperture, and wherein said fixation device is passed through the periurethral tissue at a predetermined location defined by said aperture, and thereafter through said aperture into the patient's vagina.

73. The surgical method of claim 72, wherein said at least one guide comprises a protrusion, wherein said template is aligned at least partially within the patient's vagina so that said protrusion displaces a portion of the periurethral tissue, said displacement visible from within the patient's abdominal cavity, and wherein said fixation device is passed through the periurethral tissue from within the abdominal cavity using said tissue displacement to direct placement of the fixation device.

74. The method of claim 73, wherein at least a portion of said template is expandable, and further comprising the step of expanding said expandable portion of said template after said template has been aligned within the vagina, wherein said expansion urges said protrusion against the periurethral tissue in order to provide said displacement.

75. The method of claim 61, wherein at least a portion of said template is expandable, and further comprising the step of expanding said expandable portion of said template after said template has been aligned within the vagina.

76. The surgical method of claim 73, wherein said at least one guide comprises a slot, and further comprising the steps of inserting cutting device into said slot and creating an incision in a portion of the tissue adjacent the patient's vagina using said slot to guide said cutting device, and wherein said fixation device is passed through the periurethral tissue through said incision.

77. The surgical method of claim 76, wherein said slot is positioned adjacent the periurethral tissue at a predetermined location when said template is aligned within the patient's vagina, and wherein said cutting device creates an incision in the periurethral tissue which extends into the space of Retzius, and has a length substantially corresponding to the length of said slot.

78. A method for directing placement of a fixation device through at least a portion of a patient's periurethral tissue during a surgical procedure to correct incontinence, comprising:
    (a) providing a vaginal template, said template having at least one guide for ensuring proper positioning of said fixation device;
    (b) aligning at least a portion of said template within the vagina of a patient; and
    (c) passing a portion of said fixation device through at least a portion of the patient's periurethral tissue, using said guide to direct placement of the fixation device therethrough.

79. The method of claim 78, wherein an anatomical structure of the patient's body directs alignment of at least a portion of said template within the vagina, such that said guide is located in a predetermined relationship to an anatomical landmark within the patient's body.

80. The method of claim 78, wherein said template aligned at least partially within the patient's vagina by inserting a portion of said template into the patient's urethra.

81. The method of claim 80, wherein said template has a catheter, and said catheter is inserted into the patient's urethra.

* * * * *

UNITED STATES PATENT AND TRADEMARK OFFICE
CERTIFICATE OF CORRECTION

PATENT NO. : 5,997,554
DATED : December 7, 1999
INVENTOR(S) : Ronald J. Thompson It is certified that error appears in the above-identified patent and that said Letters Patent is hereby corrected as shown below:

Claim 2, column 50, line 35, after "medical instrument", insert --through--.

Claim 2, column 50, line 37, delete "5".

Signed and Sealed this

Twenty-sixth Day of September, 2000

Attest:

Q. TODD DICKINSON

*Attesting Officer*    *Director of Patents and Trademarks*